United States Patent [19]
Grell et al.

[11] Patent Number: 6,043,254
[45] Date of Patent: Mar. 28, 2000

[54] INDOLINONES HAVING KINASE-INHIBITING ACTIVITY

[75] Inventors: Wolfgang Grell, Biberach; Helmut Wittneben, Maselheim; Jacobus Constantinus Antonius van Meel, Mittelbiberach; Norbert Redemann, Biberach; Rainer Walter, Biberach; Armin Heckel, Biberach; Frank Himmelsbach, Mittelbiberach, all of Germany; Robert Haigh, Hants, United Kingdom

[73] Assignee: Boehringer Ingelheim Pharma KG, Ingelheim, Germany

[21] Appl. No.: 09/277,063

[22] Filed: Mar. 26, 1999

Related U.S. Application Data

[60] Provisional application No. 60/086,733, May 26, 1998.

[30] Foreign Application Priority Data

Apr. 3, 1998 [DE] Germany .................. 198 15 020

[51] Int. Cl.[7] .................. A61K 31/404; A61K 31/4725; C07D 403/12; C07D 401/12
[52] U.S. Cl. .................. 514/310; 514/397; 514/414; 546/143; 548/312.1; 548/465
[58] Field of Search .................. 548/312.1, 465; 546/143; 514/310, 397, 414

[56] References Cited

U.S. PATENT DOCUMENTS 4,861,880  8/1989  Howard, Jr. et al. .................. 544/144

FOREIGN PATENT DOCUMENTS

WO95 01349  1/1995  WIPO .

Primary Examiner—Laura L. Stockton
Attorney, Agent, or Firm—Robert P. Raymond; Alan Stempel; Mary-Ellen M. Devlin

[57] ABSTRACT

The present invention relates to indolinones of general formula

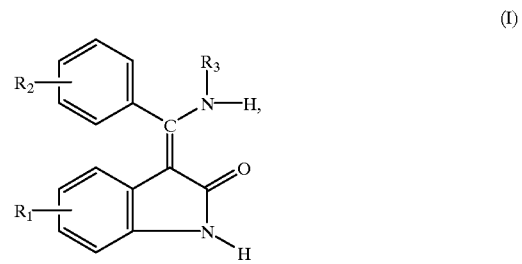

(I)

wherein $R_1$ to $R_3$ are defined in claim 1, the isomers and the salts thereof, particularly the physiologically acceptable salts thereof which have valuable pharmacological properties, particularly an inhibiting effect on various kinases and cycline/CDK complexes and on the proliferation of various tumour cells, pharmaceutical compositions containing these compounds, their use and processes for preparing them.

7 Claims, No Drawings

INDOLINONES HAVING KINASE-INHIBITING ACTIVITY

RELATED APPLICATIONS

The benefit of prior provisional application Ser. No. 60/086,733, filed on May 26, 1998, is hereby claimed.

TECHNICAL FIELD OF THE INVENTION

The invention relates to novel indolinones having kinase-inhibiting activity, the use of these compounds in the treatment of various disease conditions, pharmaceutical compositions comprising these compounds and processes for preparing them.

BACKGROUND OF THE INVENTION

The cell division cycle is one of the most fundamental biological processes, which ensures the controlled production of cells with specialised functions. The progression through the eukaryotic cell cycle is controlled by the sequential formation, activation and inactivation of a whole series of protein-serine/threonine kinases, so-called cycline-dependent kinases (CDKs; cycline-dependent kinases) (cf. M. Peter et al. in Cell 79, 181–184 (1994) and G. F. Draetta in Cell Biology 6, 842–846 (1994)). Each CDK obviously phosphorylates specific substrates and coordinates the changes which occur during a specific transition status of the cell cycle. Because of the central role of the CDKs, vigorous attempts have been made to clarify and understand their regulation. In the mean time, some mechanisms have been identified. Thus, essential subunits are only accessible during the corresponding period of the cell cycle because of the synthesis and breakdown control of cycline. Moreover, some CDK/cycline complexes are inhibited by the binding of small protein inhibitors (cycline-dependent kinase inhibitors), whose presence is also strictly controlled. Furthermore, the CDK activities are translationally regulated by reversible phosphorylation of their catalytic subunits (cf. C. Hutchinson and D. M. Glover (Editors) in Cell Cycle Control, IRL Press, London, 1994).

The primary regulator of the CDK activity is the associated cycline subunit. Cyclines, which were originally defined as proteins, the concentrations of which oscillate during the cell cycle, are now—more accurately—defined as a family of structurally related proteins which bind and activate CDK-catalytic subunits. For example, CDK1 interacts with cycline B and with cycline A; CDK2 with cycline E and cycline A; CDK4 and CDK6 with D-cyclines; and CDK7 with cycline H. The cycline function is primarily controlled by changes in the cycline concentrations which increase characteristically when the cell is in a certain state: cycline E during the G1/S phase; cycline A during the S phase; cycline B during the G2/M phase. D-cyclines and cycline H are exceptions in this respect as their concentrations are relatively constant during the entire cell cycle.

The D-cyclines and cycline E and cycline A are primarily responsible for the progression through the G1 to the S phase of the cell cycle. Growth hormones, steroid hormones, the activation of ras, and other mitogenic stimuli induce an increase in the concentration of D-cyclines and/or cycline E and thereby initiate the progression of the cell through the G1 to the S phase. A substrate for cycline D/CDK4 or cycline D/CDK6 is the retinoblastoma gene product (pRB). The retinoblastoma gene in turn is a tumour suppressor gene which controls the cell proliferation. pRB—in the hypophosphorylated form—is normally bound to the transcription factor $E_2F$, which is inactive in this complex. Hyerphosphorylation of pRB by CDKs releases $E_2F$ and induces transcription. A key role in cell growth is played by the cycline D/CDK4 or/CDK6 complex. There are increasingly indications that D-cyclines (D1 and D2) are obviously highly involved in the genesis of tumours (cf. L. H. Hartwell et al. in Science 266, 1821–1828 (1994)). The molecular mechanisms which underlie the proto-oncogenic properties of cycline D1 include chromosomal rearrangements (in parathyroid adenoma and B-cell lymphoma) and amplification of the chromosomal band 11q13, which has been reported for various types of cancer (including breast, head, neck and liver tumours) (cf. C. Gillett et al. in Cancer Research 54, 1812–1817 (1994) and T. Callender et al. in Cancer 74, 152–158 (1994)). It is assumed that the overall result of these genetic changes is an ectopic or abnormally heightened expression of the cycline D1 protein, which may possibly contribute to excessive cell divisions and unregulated tumour growth.

Another major mechanism of CDK regulation involves a family of different proteins, so-called cycline-dependent kinase inhibitors (CKIs) which bind and inhibit cycline/CDK complexes (cf. G. Peters in Nature 371, 204–205 (1994)). The chief (mammalian) CKIs fall into two categories: (1): p21 (CIP1/WAF1/-CAP20/SD1), p27 (KIP1) and p57 (KIP2) are related proteins with a preference for cycline/CDK2 and cycline/CDK4 complexes; (2) $p16^{INK4}$, $p15^{INK4B}$, $p18^{INK4C}$ and $p19^{INK4D}$ are closely related CKIs with a specificity for CDK4 and/or CDK6. p21 primarily regulates transcription. p21 transcription is induced by the tumour-suppressor gene p53, a transcriptional regulator which mediates the stopping of the cell cycle after DNA damage or in senescence. Basal concentrations of p21 may possibly constitute a threshold which has to be crossed before complexes can become active. Transcriptional control may possibly also be important for $p15^{INK4B}$, the expression of which is greatly increased when treated with the negative growth factor TGFβ. An additional effect of TGFβ is obviously the release of p27, which is established in a heat-sensitive compartment. p27 is probably also involved in the effects of positive growth factors. For example, interleukin-2 stimulation appears to induce a fall in the concentration of p27 and as a result the proliferation of T-cells.

Very recent studies have frequently shown an allelic loss at chromosome 9 in a number of human carcinomas (e.g. melanoma, head and neck squamous cell cancer, lung cancer, pancreatic adeno-Ca, breast cancer and nasopharyngeal-Ca) (cf. A. Kamb et al. in Science 264, 436–440 (1994); C. J. Hussussian et al. in Nature Genetics 8, 15–21 (1994); C. Caldas et al. in Cancer Nature Genetics 8, 27–32 (1994); T. Mori et al. in Cancer Research 54, 3396–3397 (1994) and A. Okamato et al. in Proc. Natl. Acad. Sci. USA 91, 11045–11049 (1994)). The loss of chromosome 9p21–22 is of particular interest. In this region, where a tumour suppressor gene is presumed to be, there is a gene bearing the name CDKN2 (MTS 1, Multiple Tumour Suppressor Gene 1), which codes a p16 protein. As already mentioned above, the p16 protein binds to CDK4 and CDK6 and thus inhibits their interaction with D-cyclines. Damage or mutations in the p16 gene may possibly influence the relative balance of functional p16 and cycline D, leading to unregulated CDK activity and abnormal cell growth. The very recent observations that p16 damage, inactivation by gene silencing and/or mutations very frequently occur in many tumour cells, indicate that p16 plays a key role in suppressing the development of various human carcinomas (cf. G. I. Shapiro et al. in Cancer Research 55, 6200–6209 (1995)).

Deregulated CDK activity may also be the consequence of: (a) mutation or excessive expression of the kinase; (b) induced expression, overexpression or delayed breakdown of cyclines; (c) functional inactivation of CKIs by gene silencing, damage or mutation; or (d) a combination of these phenomena. The result of these deviations is a deregulated cell cycle with deregulated cell division, which causes various illnesses or contributes to their progress.

DESCRIPTION OF THE INVENTION

It has now been found that the new substituted indolinones of general formula

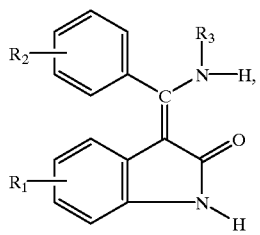

(I)

the isomers thereof, the salts thereof, particularly their physiologically acceptable salts, have valuable pharmacological properties, particularly an inhibiting effect on various kinases, particularly on complexes of CDKs (CDK1, CDK2, CDK3, CDK4, CDK6, CDK7, CDK8 and CDK9) with their specific cyclines (A, B1, B2, C, D1, D2, D3, E, F, G1, G2, H, I and K) and on viral cycline (cf. L. Mengtao et al. in J. Virology 71(3), 1984–1991 (1997)).

The present invention thus relates to the compounds of the above general formula I, the isomers thereof, the salts thereof, particularly the physiologically acceptable salts thereof, pharmaceutical compositions containing these compounds, their use and processes for preparing them.

In the above general formula I $R_1$ denotes a hydrogen, fluorine, chlorine, bromine or iodine atom, a nitro, amino, $C_{1-4}$-alkanoylamino, ($C_{1-5}$-alkoxy)carbonylamino or benzyloxycarbonylamino group, $R_2$ denotes a hydrogen, fluorine, chlorine, bromine or iodine atom, a $C_{1-5}$-alkyl, trifluoromethyl, cyano, aminocarbonyl, nitro or amino group, a $C_{1-5}$-alkyl group, which is substituted by an amino, phthalimido, $C_{1-5}$-alkylamino, $C_{3-7}$-cycloalkylamino, $C_{3-4}$-alkenylamino, benzylamino, di-($C_{1-5}$-alkyl)-amino, $C_{2-6}$-alkyleneimino, di-($C_{3-4}$-alkenyl)-amino, N-($C_{1-5}$-alkyl)-N-($C_{3-4}$-alkenyl)-amino, N-($C_{1-5}$-alkyl)-N-benzylamino, $C_{1-4}$-alkanoylamino, ($C_{1-5}$-alkoxy)carbonylamino, benzyloxycarbonylamino, N-($C_{1-4}$-alkanoyl)-N-($C_{1-5}$-alkyl)-amino, α-oxo-$C_{3-6}$-alkyleneimino, N-(($C_{1-5}$-alkoxy)carbonyl)-N-($C_{1-5}$-alkyl)-amino, N-benzyloxycarbonyl-N-($C_{1-5}$-alkyl)-amino, N-($C_{1-4}$-alkanoyl)-N-($C_{2-4}$-alkenyl)-amino, N-(($C_{1-5}$-alkoxy)carbonyl)-N-($C_{2-4}$-alkenyl)-amino, N-benzyloxycarbonyl-N-($C_{2-4}$-alkenyl)-amino, N-($C_{1-4}$-alkanoyl)-N-benzylamino, N-(($C_{1-5}$-alkoxy)carbonyl)-N-benzylamino, N-benzyloxycarbonyl-N-benzylamino, ($C_{1-5}$-alkoxy)carbonyl, benzyloxycarbonyl, carboxy, cyano, amidinocarbonyl or imidazolyl group, a $C_{2-5}$-alkenyl group, which is substituted by a phthalimido, $C_{1-4}$-alkanoylamino, ($C_{1-5}$-alkoxy)carbonylamino, benzyloxycarbonylamino, N-($C_{1-4}$-alkanoyl)-N-($C_{1-5}$-alkyl)-amino, α-oxo-$C_{3-6}$-alkyleneimino, N-(($C_{1-5}$-alkoxy)carbonyl)-N-($C_{1-5}$-alkyl)-amino, N-benzyloxycarbonyl-N-($C_{1-5}$-alkyl)-amino, N-($C_{1-4}$-alkanoyl)-N-($C_{2-4}$-alkenyl)-amino, N-(($C_{1-5}$-alkoxy)carbonyl)-N-($C_{2-4}$-alkenyl)-amino, N-benzyloxycarbonyl-N-($C_{2-4}$-alkenyl)-amino, N-($C_{1-4}$-alkanoyl)-N-benzylamino, N-(($C_{1-5}$-alkoxy)carbonyl)-N-benzylamino, N-benzyloxycarbonyl-N-benzylamino, ($C_{1-5}$-alkoxy)carbonyl, benzyloxycarbonyl, carboxy, cyano or aminocarbonyl group, or an allyl group which is substituted in the 3-position by an amino, $C_{1-5}$-alkylamino, $C_{3-7}$-cycloalkylamino, $C_{3-4}$-alkenylamino, benzylamino, di-($C_{1-5}$-alkyl)-amino, $C_{2-6}$-alkyleneimino, di-($C_{3-4}$-alkenyl)-amino, N-($C_{1-5}$-alkyl)-N-($C_{3-4}$-alkenyl)-amino or N-($C_{1-5}$-alkyl)-N-benzylamino group, and $R_3$ denotes a group of the formulae

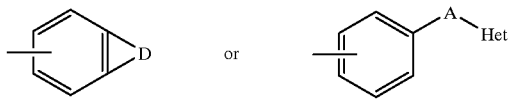

wherein

A denotes a bond, a $C_{1-4}$-alkylene, $C_{1-4}$-alkylidene, $C_{2-4}$-alkenylene or $C_{2-4}$-alkenylidene group, whilst a hydrogen atom which is bound to the carbon atom of the binding site in the group Het, together with a hydrogen atom of the group A in the α-position, may also be replaced by another carbon-carbon bond, D denotes a —CH=CH—$NR_a$—, —CH=N—$NR_a$—, —N=CH—$NR_a$—, —$NR_a$—CO—$NR_b$—, —$CH_2$—CO—$NR_a$—, —CO—$NR_c$—CO—, —$CH_2$—$NR_a$—$CH_2$—, —$CH_2$—$CH_2$—$NR_a$—, —CH=CH—CH=N, —$CH_2$—$CH_2$—$CH_2$—$NR_d$—, —CH=CH—N=CH, —$CH_2$—$CH_2$—$NR_d$—$CH_2$—, —$CH_2$—$CH_2$—CO—NH, —CH=CH—CO—NH, —$NR_a$—CO—CH=N or —($R_a CR_b$)—CO—$NR_a$—CO bridge, whilst $R_a$ and $R_b$, which may be identical or different, each denote a hydrogen atom or a methyl group, $R_c$ denotes a hydrogen atom, a ($C_{1-5}$-alkoxy)carbonyl-$C_{1-5}$-alkyl or benzyloxycarbonyl-$C_{1-5}$-alkyl group and $R_d$ denotes a hydrogen atom, a $C_{1-5}$-alkyl, $C_{1-4}$-alkanoyl, ($C_{1-5}$-alkoxy)carbonyl or benzyloxycarbonyl group, and Het denotes a 5-membered heteroaromatic ring which contains a nitrogen atom or a nitrogen atom and an oxygen, sulphur or nitrogen atom, whilst the abovementioned ring may also be substituted by a $C_{1-5}$-alkyl, $C_{5-7}$-cycloalkyl, phenyl, phenyl-$C_{1-3}$-alkyl, amino, $C_{1-4}$-alkanoylamino, ($C_{1-5}$-alkoxy) carbonylamino or benzyloxycarbonylamino group and also by a further $C_{1-5}$-alkyl group, a 5-membered dihydrogenated heteroaromatic ring which contains a nitrogen atom or a nitrogen atom and an oxygen, sulphur or nitrogen atom, whilst the abovementioned ring may also be substituted by one or two $C_{1-5}$-alkyl groups and may contain a carbonyl group and additionally may be substituted at a cyclic nitrogen atom by a ($C_{1-5}$-alkoxy)carbonyl or benzyloxycarbonyl group, a 5-membered tetrahydrogenated heteroaromatic ring, which contains a nitrogen atom, whilst the abovementioned ring may additionally be substituted by one or two $C_{1-5}$-alkyl groups, by a hydroxy, carboxy, ($C_{1-5}$-alkoxy)carbonyl or aminocarbonyl group and may also contain one or two carbonyl groups, a 5-membered tetrahydrogenated heteroaromatic ring which contains a nitrogen atom and an oxygen, sulphur or nitrogen atom, whilst the abovementioned ring may additionally be substituted by one or two $C_{1-5}$-alkyl groups and may contain one or two carbonyl groups, a tetrazolyl or imidazo[1,2-a]pyrimidin-2-yl group.

Preferred compounds of the above general formula I are those wherein $R_1$ denotes a hydrogen, fluorine, chlorine or bromine atom, a nitro, amino, $C_{1-4}$-alkanoylamino, ($C_{1-5}$-alkoxy)carbonylamino or benzyloxycarbonylamino group, $R_2$ denotes a hydrogen, fluorine, chlorine or bromine atom, a methyl, trifluoromethyl, cyano, aminocarbonyl, nitro or amino group, a $C_{1-2}$-alkyl group, which is substituted by an amino, phthalimido, $C_{1-2}$-alkylamino, di-($C_{1-2}$-alkyl)-amino, $C_{2-6}$-alkyleneamino, $C_{1-2}$-alkanoylamino, ($C_{1-5}$-alkoxy)carbonylamino, benzyloxycarbonylamino, N-($C_{1-2}$-alkanoyl)-N-($C_{1-2}$-alkyl)-amino, N-(($C_{1-5}$-alkoxy)carbonyl)-N-($C_{1-2}$-alkyl)-amino, α-oxo-$C_{3-6}$-alkyleneimino, N-benzyloxycarbonyl-N-($C_{1-2}$-alkyl)-amino, ($C_{1-5}$-alkoxy)carbonyl, benzyloxycarbonyl, carboxy, cyano, aminocarbonyl or imidazolyl group, or an allyl group which is substituted in the 3 position by a $C_{2-6}$-alkylene or α-oxo-$C_{3-6}$-alkyleneimino group, $R_3$ denotes a group of the formulae

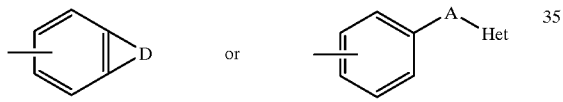

wherein D and Het are as hereinbefore defined and A denotes a bond, a $C_{1-3}$-alkylene, $C_{1-3}$-alkylidene, $C_{2-3}$-alkenylene or $C_{2-3}$-alkenylidene group, whilst a hydrogen atom which is bound to the carbon atom of the binding site in the group Het, together with a hydrogen atom of the group A in the α-position, may also be replaced by another carbon-carbon bond, the isomers and the salts thereof.

Particularly preferred compounds of the above general formula I are those wherein $R_1$ denotes a hydrogen atom or a nitro group, $R_2$ denotes a hydrogen or chlorine atom, a methyl, trifluoromethyl, cyano, aminomethyl, aminoethyl or phthalimido group, a methyl or ethyl group each of which is substituted by a methylamino, dimethylamino, ethylamino, diethylamino, pyrrolidino, piperidino, α-oxo-pyrrolidino, α-oxo-piperidino, acetylamino, methoxycarbonylamino, ethoxycarbonylamino, benzyloxycarbonylamino, N-acetyl-N-methyl amino, N-methoxycarbonyl-N-methyl-amino, N-ethoxycarbonyl-N-methyl-amino, N-benzyloxycarbonyl-N-methyl-aminomethyl, 2-(N-benzyloxy-carbonyl-N-methyl-amino)-ethyl or imidazolyl group, $R_3$ denotes a 1-methyl-2-oxo-2,3-dihydro-1H-benzimidazol-5-yl, 1,2,3,4-tetrahydro-isoquinolin-6-yl, 2-acetyl-1,2,3,4-tetrahydro-isoquinolin-6-yl, 2-acetyl-1,2,3,4-tetrahydro-isoquinolin-7-yl, 2-ethyl-1,2,3,4-tetrahydro-isoquinolin-6-yl, 2-ethyl-1,2,3,4-tetrahydro-isoquinolin-7-yl, 4-(imidazol-2-yl)-phenyl, 4-(1-methyl-imidazol-2-yl)-phenyl, 4-(imidazol-4-yl)-phenyl, 4-(1-methyl-imidazol-4-yl)-phenyl, 4-(1-methyl-imidazol-5-yl)-phenyl, 4-(5-methyl-imidazol-4-yl)-phenyl, 4-(4-methyl-imidazol-5-yl)-phenyl, 4-(2-methyl-imidazol-4-yl)-phenyl, 4-(2-ethyl-imidazol-4-yl)-phenyl, 4-(2-acetylamino-imidazol-4-yl)-phenyl, 4-(2-acetylamino-5-methyl-imidazol-4-yl)-phenyl, imidazo[1,2-a]pyrimidin-2-yl, 4-[(2,4-dioxo-imidazolidin-5-yl)methyl]-phenyl, 4-[(2,4-dioxo-imidazolidin-5-ylidene)methyl]-phenyl, 4-[(imidazol-4-yl)methyl]-phenyl, 4-[(imidazol-5-yl)methyl]-phenyl, 4-[(1-pyrrolidinyl)methyl]-phenyl, 4-[2-(imidazol-4(5)-yl)ethyl]-phenyl, 4-[2-(imidazol-4-yl)ethenyl]-phenyl or 4-[2-(imidazol-5-yl)ethenyl]-phenyl group, the isomers and the salts thereof.

Most particularly preferred compounds of the above general formula I are those wherein $R_1$ denotes a hydrogen atom or in the 5-position a nitro group, $R_2$ denotes a hydrogen atom, a methyl or trifluoromethyl group, $R_3$ denotes a 4-(1-methyl-imidazol-2-yl)-phenyl, 4-(imidazol-4-yl)-phenyl, 4-(imidazol-5-yl)-phenyl, 4-(1-methyl-imidazol-4-yl)-phenyl, 4-(1-methyl-imidazol-5-yl)-phenyl, 4-(2-methyl-imidazol-4-yl)-phenyl, 4-(2-acetylamino-imidazol-4-yl)-phenyl, 4-[(2,4-dioxo-imidazolidin-5-ylidene)methyl]-phenyl, 4-[(1-pyrrolidinyl)-methyl]-phenyl, 4-[2-(imidazol-4-yl)ethenyl]-phenyl or 1,2,3,4-tetrahydro-isoquinolin-6-yl group, the isomers and the salts thereof.

The following are mentioned as examples of particularly preferred compounds:

(a) 3-{(Z)-1-[4-(1H-imidazol-4-yl)anilino]-1-phenylmethylidene}-2-indolinone, (b) 3-{(Z)-1-[4-(1H-imidazol-4-yl)anilino]-1-phenylmethylidene}-5-nitro-2-indolinone, (c) 3-{(Z)-1-[4-(1H-imidazol-4-yl)anilino]-1-(4-trifluoromethyl-phenyl)methylidene}-5-nitro-2-indolinone, (d) 3-{(Z)-1-[4-(1H-imidazol-4-yl)anilino]-1-(4-methyl-phenyl)methylidene}-5-indolinone, (e) 3-{(Z)-1-[4-((2,4-dioxo-imidazolidin-5-yl)methyl)anilino]-1-phenylmethylidene}-5-nitro-2-indolinone, (f) 3-{(Z)-1-[4-(2-methyl-1H-imidazol-4-yl)anilino]-1-phenylmethylidene}-5-nitro-2-indolinone, (g) 3-{(Z)-1-[4-((pyrrolidin-1-yl)methyl)anilino]-1-phenylmethylidene}-5-nitro-2-indolinone and (h) 3-{(Z)-1-[(1,2,3,4-tetrahydro-isoquinolin-6-yl)amino]-1-phenylmethylidene}-5-nitro-2-indolinone and the salts thereof.

According to the invention the new compounds are obtained for example by the following methods known in principle from the literature:

a. reacting a compound of general formula

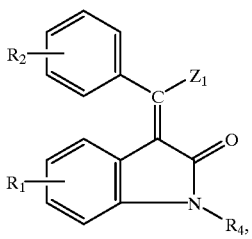

(II)

wherein $R_1$ and $R_2$ are as hereinbefore defined, $R_4$ denotes a hydrogen atom or a protecting group for the nitrogen atom of the lactam group and $Z_1$ denotes a halogen atom, a hydroxy, alkoxy or aralkoxy group, e.g. a chlorine or bromine atom, a methoxy, ethoxy or benzyloxy group, with an amine of general formula $$H_2N—R_3 \quad (III),$$

wherein $R_3$ is as hereinbefore defined, and subsequently, if necessary, cleaving any protecting group used for the nitrogen atom of the lactam group.

A suitable protecting group for the nitrogen atom of the lactam group might be for example an acetyl, benzoyl, ethoxycarbonyl, tert.butyloxycarbonyl or benzyloxycarbonyl group.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 25 and 175° C., whilst any protecting group used can be cleaved simultaneously by transamidation.

If $Z_1$ in a compound of general formula II denotes a halogen atom, the reaction is preferably carried out in the presence of an inert base at temperatures between 25 and 120° C.

If $Z_1$ in a compound of general formula II denotes a hydroxy, alkoxy or aralkoxy group, the reaction is preferably carried out at temperatures between 80 and 150° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with a primary or secondary organic base such as methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

b. In order to prepare a compound of general formula I wherein $R_2$ represents one of the alkenyl or allyl groups mentioned for $R_2$ hereinbefore:

reacting a halophenyl compound of general formula

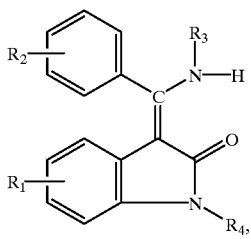

(IV)

wherein $R_1$, $R_3$ and $R_4$ are as hereinbefore defined and $Z_2$ denotes a chlorine, bromine or iodine atom, with an alkene of general formula $$R_2'—H \quad (V),$$

wherein $R_2'$ represents one of the substituted alkenyl groups mentioned for $R_2$ hereinbefore, in the presence of a suitable catalyst containing a noble metal and subsequently, if necessary, cleaving any protecting group used for the nitrogen atom of the lactam group.

Suitable noble metal catalysts are preferably palladium-containing catalysts such as palladium-diacetate or palladium dichloride, particularly the complexes thereof with triphenylphosphine or tri-(o-toluene)-phosphine, optionally in the presence of activators such as tetraphenylphosphonium chloride or bromide and N,N-dimethylglycine.

The Heck reaction is conveniently carried out under a protective gas, e.g. under nitrogen or argon, optionally in a pressure vessel and expediently in a solvent such as acetonitrile, dimethylformamide or N-methyl-pyrrolidin-2-one at temperatures between 20 and 180° C., preferably at temperatures between 80 and 150° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide, potassium hydroxide or sodium acetate at temperatures between 0 and 100° C., preferably at temperatures between 10 and 50° C., or advantageously by transamidation with a primary or secondary organic base such as methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

c. In order to prepare a compound of general formula I, wherein A denotes a $C_{2-4}$-alkenylene group:

reacting a halophenyl compound of general formula

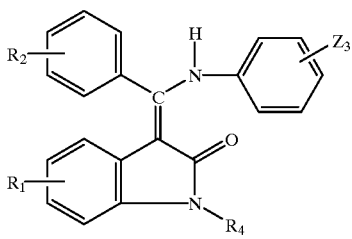

(VI)

wherein $R_1$, $R_2$ and $R_4$ are as hereinbefore defined and $Z_3$ denotes a chlorine, bromine or iodine atom, with an alkene of general formula H—A'—Het  (VII), wherein Het is as hereinbefore defined and A' denotes a $C_{2-4}$-alkenylene group, in the presence of a suitable catalyst containing a noble metal and subsequently, if desired, cleaving any protecting group used for the nitrogen atom of the lactam group.

Suitable noble metal catalysts are preferably palladium-containing catalysts such as palladium diacetate or palladium dichloride, particularly the complexes thereof with triphenylphosphine or tri-(o-toluene)-phosphine, optionally in the presence of activators such as tetraphenylphosphonium chloride or bromide and N,N-dimethylglycine.

The Heck reaction is conveniently carried out under a protective gas, e.g. under nitrogen or argon, optionally in a pressure vessel and expediently in a solvent such as acetonitrile, dimethylformamide or N-methyl-pyrrolidin-2-one at temperatures between 20 and 180° C., preferably at temperatures between 80 and 150° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide, potassium hydroxide or sodium acetate at temperatures between 0 and 100° C., preferably at temperatures between 10 and 50° C., or advantageously by transamidation with a primary or secondary organic base such as methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

d. In order to prepare a compound of general formula I wherein A denotes a bond or a $C_{1-4}$-alkylene group and Het denotes one of the optionally mono or disubstituted (4,5-dihydro-imidazol-2-yl) groups mentioned for Het hereinbefore:

reacting an iminoether-phenyl compound of general formula

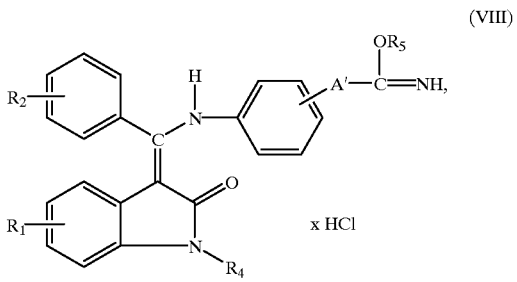

(VIII)

x HCl wherein $R_1$, $R_2$ and $R_4$ are as hereinbefore defined,

A' denotes a bond or a $C_{1-4}$-alkylene group and $R_5$ denotes an alkyl group, e.g. a methyl or ethyl group, with an ethylenediamine, which may be substituted by a $C_{1-5}$-alkyl group at one of the nitrogen or carbon atoms or at one of the nitrogen atoms and at one of the carbon atoms and subsequently, if necessary, cleaving any protecting group used for the nitrogen atom of a lactam group.

The reaction is expediently carried out in a solvent such as diethylether, methanol or ethanol, but preferably in an excess of the ethylenediamine used at temperatures between 0 and 100° C., preferably at temperatures between 10 and 50° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with a primary or secondary organic base such as methylamine, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

If according to the invention a compound of general formula I is obtained wherein $R_3$ denotes an (imidazo[1,2-a]pyrimidin-2-yl)phenyl group, this may be converted by hydrazinolysis into a corresponding (2-amino-imidazol-4 (5)-yl)phenyl compound, or if a compound of general formula I is obtained wherein $R_2$ contains a phthalimido group, this can be converted by hydrazinolysis into a corresponding amino compound, or if a compound of general formula I is obtained wherein $R_2$ denotes a cyano, cyanoalkyl or cyanoalkenyl group, this can be converted by reduction, preferably by catalytic hydrogenation, into a corresponding aminomethyl or aminoalkyl compound, or if a compound of general formula I is obtained wherein $R_2$ denotes a cyano, cyanoalkyl or cyanoalkenyl group, this can be converted by hydration into a corresponding aminocarbonyl, aminocarbonylalkyl or aminocarbonylalkenyl-compound, or if a compound of general formula I is obtained wherein $R_2$ contains an alkenylene group, this can be converted by reduction, preferably by catalytic hydrogenation, into a corresponding alkylene compound, or if a compound of general formula I is obtained wherein $R_3$ contains an alkenylene group, this can be converted by reduction, preferably by catalytic hydrogenation, into a corresponding alkylene compound, or if a compound of general formula I is obtained wherein $R_3$ denotes an (amino-imidazolyl)phenyl group which is substituted by an alkanoyl or benzyloxycarbonyl group, as mentioned for $R_3$ hereinbefore, this can be converted by hydrolysis or hydrogenolysis into a corresponding unsubstituted compound, or if a compound of general formula I is obtained wherein $R_3$ denotes one of the unsubstituted (amino-imidazolyl) phenyl groups mentioned for $R_3$, this can be converted by acylation into a corresponding acyl compound, or if a compound of general formula I is obtained wherein $R_2$ denotes one of the groups mentioned $R_2$ hereinbefore which contain an amino, alkylamino, alkenylamino or benzylamino group, this can be converted by acylation into a corresponding acyl compound, or if a compound of general formula I is obtained wherein $R_1$ denotes a nitro group, this can be converted by reduction, preferably by catalytic hydrogenation, into a corresponding amino compound, or if a compound of general formula I is obtained wherein $R_1$ denotes an amino group, this can be converted by acylation into the corresponding acyl compound, or if a compound of general formula I is obtained wherein A denotes an alkenylene, alkylidene or alkenylidene group, this can be converted by catalytic hydrogenation into a corresponding alkylene compound, or if a compound of general formula I is obtained wherein $R_3$ denotes a phthalimido group substituted by a ($C_{1-5}$-alkoxy)carbonyl-$C_{1-5}$-alkyl or benzyloxycarbonyl-$C_{1-5}$-alkyl group, this can be converted by acidolysis or hydrogenolysis into a corresponding carboxy compound, or if a compound of general formula I is obtained wherein $R_2$ contains an alkoxycarbonyl or benzyloxycarbonyl group, this can be converted by hydrolysis or hydrogenolysis into a corresponding carboxy compound, or if a compound of general formula I is obtained wherein $R_2$ denotes an acylated aminoalkyl group, this can be converted by hydrolysis or hydrogenolysis into a corresponding aminoalkyl compound, or if a compound of general formula I is obtained wherein $R_1$ or/and $R_2$ denote a halogen atom, this can be converted by catalytic hydrogenation into a corresponding dehalogenated compound, or if a compound of general formula I is obtained wherein $R_3$ denotes a 2-Boc, 2-Z or 2-benzyl-1,2,3,4-tetrahydroisoquinolinyl group, this can be converted by hydrolysis or hydrogenolysis into a corresponding 1,2,3,4-tetrahydroisoquinolinyl compound, or if a compound of general formula I is obtained wherein $R_3$ denotes a 1,2,3,4-tetrahydro-isoquinolyl group, this can be converted by acylation into a corresponding 2-acyl-1,2,3,4-tetrahydro-isoquinolyl compound, or if a compound of general formula I is obtained wherein Het denotes one of the groups mentioned for Het hereinbefore which is substituted at a cyclic nitrogen atom by a ($C_{1-5}$-alkoxy)carbonyl or benzyloxycarbonyl group, this can be converted by acidolysis or hydrogenolysis into a corresponding NH compound.

The subsequent hydrazinolysis is preferably carried out in a solvent such as methanol, ethanol, isopropanol, toluene/water or dioxane, but most advantageously in hydrazine hydrate as solvent, at temperatures between 20 and 120° C., preferably at the boiling temperature of the solvent used.

The subsequent reduction of an alkenyl, nitro, cyano, cyanoalkyl or cyanoalkenyl compound is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably from 3 to 5 bar.

The subsequent hydration is preferably carried out using concentrated sulphuric acid or polyphosphoric acid at temperatures between 0 and 50° C., but preferably at temperatures between 0 and 25° C.

The subsequent hydrolysis is preferably carried out in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent hydrogenolysis is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, but preferably 3 to 5 bar.

The subsequent acylation is preferably carried out in a solvent such as methylene chloride, diethylether, tetrahydrofuran, toluene, dioxane, acetonitrile, dimethylsulphoxide or dimethylformamide optionally in the presence of an inorganic or tertiary organic base, preferably at temperatures between 20° C. and the boiling temperature of the solvent used. The acylation with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine expediently at temperatures between 0 and 150° C., preferably at temperatures between 0 and 100° C., and the acylation with a corresponding reactive compound such as the anhydride, ester, imidazolide or halide thereof is optionally carried out in the presence of a tertiary organic base such as triethylamine, N-ethyl-diisopropylamine or N-methyl-morpholine at temperatures between 0 and 150° C., preferably at temperatures between 50 and 100° C.

The subsequent acidolysis is preferably carried out in an aqueous solvent, e.g. in water, isopropanol/water, tetrahydrofuran/water or dioxane/water, in the presence of an acid such as trifluoroacetic acid, hydrochloric acid or sulphuric acid between 0 and 100° C., preferably at temperatures between 10 and 50° C.

The subsequent dehalogenation is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as glacial acetic acid or of a base such as sodium bicarbonate or triethylamine at temperatures between 0 and 50° C., but preferably at ambient temperature, and at a hydrogen pressure of 1 to 7 bar, but preferably from 3 to 5 bar.

In the reactions described hereinbefore, any reactive groups present such as carboxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl. methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+) or (−)-menthol and an optically active acyl group in amides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae I to VIII used as starting materials are known from the literature in some cases or may be obtained by methods known from the literature or are described in the Examples.

As already mentioned, the new compounds of general formula I have valuable pharmacological properties, particularly inhibitory effects on various kinases and cycline/CDK-complexes, on the proliferation of cultivated human tumour cells and, when administered orally, on the growth of tumours in nude mice infected with human tumour cells.

For example, the new compounds were tested for their biological properties in the following tests:

Test 1

Inhibition of cycline/CDK Enzyme in vitro Activity

High Five™ insect cells (BTI-TN-5B1-4) which had been infected with a high titre of recombinant baculovirus were used to produce active human cycline/CDK holoenzymes. By using a baculovirus vector which contained two promoters (polyhedrin enhancer promoter, P10 enhancer promoter), GST-tagged cyclines (e.g. cycline D1 or cycline D3) with the corresponding $His_6$-tagged CDK subunit (e.g. for CDK4 or CDK6) were expressed in the same cell. The active holoenzyme was isolated by affinity chromatography on glutathione sepharose. Recombinant GST-tagged pRB (aa 379–928) was produced in E. coli and purified by affinity chromatography on glutathione sepharose.

The substrates used for the kinase assays depended on the specific kinases. Iistone H1 (Sigma) was used as the substrate for cycline E/CDK2, cycline A/CDK2, cycline B/CDK1 and for v-cycline/CDK6. GST-tagged pRB (aa 379–928) was used as substrate for cycline D1/CDK4, cycline D3/CDK4, cycline D1/CDK6 and for cycline D3/CDK6.

Lysates of the insect cells infected with recombinant baculovirus or recombinant kinases (obtained from the lysates by purification) were incubated together with radiolabelled ATP in the presence of a suitable substrate with various concentrations of the inhibitor in a 1% DMSO solution (dimethyl sulphoxide) for 45 minutes at 30° C. The substrate proteins with associated radioactivity were precipitated with 5% TCA (trichloroacetic acid) in water-repellent PVDF multi-well microtitre plates (Millipore) or with 0.5% phosphoric acid solution on Whatman P81 filters. After the addition of scintillation liquid the radioactivity was measured in a Wallace 1450 Microbeta Liquid Scintillation Counter. For each concentration of the substance double measurements were carried out; $IC_{50}$ values were calculated for the enzyme inhibition.

Test 2

Inhibition of the Proliferation of Cultivated Human Tumour Cells

Cells of the Leimyosarcoma tumour cell line SK-UT-1B (obtained from the American Type Culture Collection (ATCC)) were cultivated in Minimum Essential Medium with non-essential amino acids (Gibco), supplemented with sodium pyruvate (1 mmol), glutamine (2 mmol) and 10% foetal calf serum (Gibco) and harvested during the log-growth phase. Then the SK-UT-1B cells were added to Cytostar® multi-well plates (Amersham) at a density of 4000 cells per well and incubated overnight in an incubator. Various concentrations of the compounds (dissolved in DMSO; final concentration: <1%) were added to the cells. After 48 hours' incubation $^{14}$C-thymidine (Amersham) was added to each well and incubation was continued for a further 24 hours. The quantity of $^{14}$C-thymidine incorporated into the tumour cells in the presence of the inhibitor and representing the number of cells in the S phase was measured in a Wallace 1450 Microbeta Liquid Scintillation Counter. $IC_{50}$ values for the inhibition of proliferation (=inhibition of incorporated $^{14}$C-thymidine) were calculated, correcting for the background radiation. All the measurements were done twice.

Test 3

In vivo Effects on Tumour-bearing Nude Mice $10^6$ cells [SK-UT-1B, or non-small cell lung tumour NCI-H460 (obtained from ATCC)] in a volume of 0.1 ml were injected subcutaneously into male and/or female nude mice (NMRI nu/nu; 25–35 g; N=10–20); alternatively, small fragments of SK-UT-1B or NCI-H460 cell clumps were implanted subcutaneously. One to three weeks after the injection or implantation a kinase inhibitor was administered daily by oral route for a period of 2 to 4 weeks (by oesophageal tube). The size of the tumour was measured three times a week using a digital sliding gauge. The effect of a kinase inhibitor on the tumour growth was determined as a percentage inhibition compared with a control group treated with placebo.

The following Tables 1 and 2 contain the results of tests 1 and 2:

TABLE 1

(test 1)

| Compound (Example No.) | Inhibition of cycline D1/CDK4 $IC_{50}$ [µM] |
|---|---|
| 14.1 | 0.15 |
| 18.2 | 1.4 |
| 14.2 | 0.0066 |
| 4.9 | 0.055 |
| 2.5 | 1.0 |

TABLE 2

(test 2)

| Compound (Example No.) | Inhibiting the proliferation of SKUT-1B cells: $IC_{50}$ [µM] |
|---|---|
| 3.12 | 0.40 |
| 3.18 | 0.22 |
| 8.3 | 1.3 |
| 4.11 | 0.53 |
| 2.5 | 0.34 |

The following results were obtained in test no. 3 (in vivo): Administration (100 mg/kg p.o. of the compound of Example 2.5 once a day for two weeks) to male nude mice (n=9) yielded a significant reduction in the tumour size of around 65% (p<0.05).

In view of their biological properties, the new compounds of general formula I, their isomers and physiologically acceptable salts are suitable for the treatment of diseases characterised by excessive or abnormal cell proliferation.

Such diseases include (with no claim to completeness): viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also useful for protecting proliferating cells (e.g. hair, intestinal, blood and progenitor cells) against DNA damage caused by radiation, UV treatment and/or cytostatic treatment.

The new compounds may be used for the short-term or long-term treatment of the abovementioned diseases, optionally in conjunction with other state-of-the-art compounds such as other cytostatics.

The dosage required to achieve such an effect is appropriately 0.1 to 30 mg/kg, preferably 0.3 to 10 mg/kg by intravenous route, and 0.1 to 100 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories, or as solutions for injections or infusions.

The Examples which follow are intended to illustrate the invention. In the Examples the following abbreviations are used:

| | |
|---|---|
| Boc = | tert.butyloxycarbonyl |
| Bzl = | benzyl |
| $CH_2Cl_2$ = | methylene chloride |
| DBU = | 1,8-diazabicyclo[5.4.0]undec-7-ene |
| DC = | thin layer chromatogram |
| DMF = | dimethylformamide |
| DMSO = | dimethylsulphoxide |
| EtOAc = | ethylacetate |
| EtOH = | ethanol |
| HOBT = | N-hydroxy-1H-benzotriazole |
| Hünig's base = | N-ethyl-N,N-diisopropyl-amine |
| MeOH = | methanol |
| MS = | mass spectrum |
| TBTU = | O-(benzotriazol-1-yl)-N,N,N',N'-tetramethyl uronium-tetrafluoroborate |
| THF = | tetranydrofuran |
| $T_i$ = | internal temperature |
| Z = | benzyloxycarbonyl |
| (Z); (E) = | configuration |

PREPARATION OF THE STARTING COMPOUNDS

EXAMPLE A 1-acetyl-2-indolinone

Prepared by refluxing 2-indolinone with 1 equivalent of acetic anhydride in a bath at 170° C. for 3 hours.

Yield: 96% of theory; Melting point: 129–130° C.

EXAMPLE B 1-acetyl-3-{1-ethoxy-1-phenylmethylidene}-2-indolinone

Prepared by refluxing 3 equivalents of 1-acetyl-2-indolinone with 6 equivalents of triethyl orthobenzoate and acetic anhydride in a bath at 160° C. for 22 hours. After evaporation in vacuo the residue is mixed with petroleum ether. After standing overnight the product precipitated is filtered off and dried at 60° C.

Yield: about 67% of theory, the product contains about 25 to 34% of 1-acetyl-2-indolinone. Melting point: 123–129° C. (with an amount of 34% of 1-acetyl-2-indolinone). An insoluble fraction is isolated from the above mixture by combining with ethylacetate, extracting with dilute aqueous sodium carbonate solution and with water and by filtering, this fraction being the pure product. Melting point: 187–189° C.; $C_{19}H_{17}NO_3$; Calc.: C, 74.25; H, 5.57; N, 4.56; Found: 73.95; 5.57; 4.53.

EXAMPLE C

3-{1-ethoxy-1-phenylmethylidene}-2-indolinone

The mixture obtained in Example B consisting of 66% of 1-acetyl-3-{1-ethoxy-1-phenylmethylidene}-2-indolinone and 34% of 1-acetyl-2-indolinone is suspended in ethanol (8 ml/g), 2 equivalents of 4N sodium hydroxide solution are added and the mixture is stirred at ambient temperature for 1.5 hours. After the addition of water (25 ml/g) the precipitate formed is filtered off, washed with water and a little ether and dried at 80° C.

Yield: 80% of theory (based on the amount of 1-acetyl-3-{1-ethoxy-1-phenylmethylidene}-2-indolinone used);

Melting point: 168–169° C.; $C_{17}H_{15}NO_2$; Calc.: C, 76.96; H, 5.70; N, 5.28; Found: 76.69; 5.62; 5.23.

EXAMPLE D 1-acetyl-5-nitro-2-indolinone

Prepared by reacting 1-acetyl-2-indolinone in concentrated sulphuric acid (5.7 ml/g) at −10° C. with 1.1 equivalents of ammonium nitrate which is added in batches with stirring. After the addition has ended the mixture is stirred for a further 15 minutes, poured onto ice water, the precipitate is filtered off, washed with water and dissolved in ethylacetate. The organic phase is extracted with water, dried, filtered and evaporated down in vacuo. The evaporation residue is stirred with petroleum ether.

Yield: 93% of theory; Melting point: 154–156° C.; $C_{10}H_8N_2O_4$; Calc.: C, 54.55; H, 3.66; N, 12.72; Found: 54.36; 3.67; 13.00.

EXAMPLE E 1-acetyl-3-{1-ethoxy-1-phenylmethylidenel-5-nitro-2-indolinone

Prepared by refluxing 3 equivalents of 1-acetyl-5-nitro-2-indolinone with triethyl orthobenzoate and 8 equivalents of acetic anhydride in a bath at 100° C. for 2.5 hours. The mixture is cooled in an ice bath, petroleum ether is added and the resulting mixture is stirred for 1 hour. The solid substance is filtered, washed with petroleum ether and ether and dried at 60° C.

Yield: 77% of theory; Melting point: 235–238° C.; $C_{19}H_{16}N_2O_5$; Calc.: C, 64.77; H, 4.58; N, 7.95; Found: 64.60; 4.59; 7.99.

EXAMPLE F

3-{1-ethoxy-1-phenylmethylidene}-5-nitro-2-indolinone 1.5 equivalents of 1N sodium hydroxide solution are added dropwise to a stirred mixture of 1-acetyl-3-{1-ethoxy-1-phenylmethylidene}-5-nitro-2-indolinone in methylene chloride (11 ml/g) and EtOH (8.5 ml/g) whilst cooling with ice so that the internal temperature does not exceed 14 to 17° C. Then stirring is continued for 0.5 hours at ambient temperature and the methylene chloride is eliminated by evaporation in vacuo at a bath temperature of 30° C. Water is added (11 ml/g) and the mixture is thoroughly stirred. The precipitate is filtered, washed with water, isopropanol and lastly with ether and dried at 100° C.

Yield: 86% of theory; Melting point: 239–240° C.; $C_{17}H_{14}N_2O_4$; Calc.: C, 65.80; H, 4.55; N, 9.03; Found: 65.45; 4.43 8.81; Calc.: molar peak $M^+$=310; Found: molar peak $M^+$=310.

PREPARATION OF THE END PRODUCTS

EXAMPLE 1

3-{(Z)-1-[(Indol-5-yl)amino]-1-phenylmethylidene}-2-indolinone 0.307 g (1 mmol) of 1-acetyl-3-{1-ethoxy-1-phenylmethylidene}-2-indolinone and 0.400 mg (3 mmol) of 5-amino-indole are refluxed in 10 ml toluene for 1 hour. The mixture is evaporated down in vacuo and the evaporation residue is distributed between EtOAc and water. A viscous oil is obtained from the organic phase after drying, filtering and evaporation in vacuo, and this oil is purified by column chromatography on silica gel with the eluant EtOac/petroleum ether (1:1).

Yield: 0.11 g (31% of theory); Melting point: 263–265° C.; $C_{23}H_{17}N_3O$; Calc.: C, 78.61; H, 4.88; N, 11.96; Found: 78.28; 4.91; 11.76; Calc.: molar peak $M^+=351$; Found: molar peak $M^+=351$.

The following compound was obtained analogously to Example 1:

1.1 3-{(Z)-1-[(1-methyl-benzimidazol-5-yl)amino]-1-phenylmethylidene}-2-indolinone×2 $H_2O$ Prepared by heating 1-acetyl-3-{1-ethoxy-1-phenylmethylidene}-2-indolinone and 2 equivalents of 5-amino-1-methyl-benzimidazole, melting point 158–160° C. in DMF for 1.5 hours at 120° C., subsequently precipitating with water and digesting in MEOH.

Yield: 60% of theory; Melting point: 307–308° C.; $C_{23}H_{18}N_4O\times 2\ H_2O$; Calc.: C, 68.64; H, 5.51; N, 13.92; Found: 68.65; 5.51; 13.85; Calc.: molar peak $M^+=366$; Found: molar peak $M^+=366$.

EXAMPLE 2

3-{(Z)-1-[(2-Indazol-5-yl)amino]-1-phenylmethylidene}-2-indolinone 0.307 g (1 mmol) of 1-acetyl-3-{1-ethoxy-1-phenylmethylidene}-2-indolinone and 0.400 mg (3 mmol) of 5-amino-indazole are heated in 5 ml DMF for 2 hours at 120° C. The mixture is diluted with water and extracted with EtOac. The organic phase is extracted three times with water, dried, filtered and evaporated down in vacuo. The oily evaporation residue is dissolved in MeOH. 2 ml of 1N sodium hydroxide solution are added whilst cooling with ice and the mixture is stirred for 1 hour at ambient temperature. It is evaporated in vacuo almost to dryness, water is added, the solid substance is filtered off, washed with water and digested with MeOH. It is purified by column chromatography on silica gel with the eluant EtOac.

Yield: 0.15 g (42% of theory); Melting point: 287–289° C.; $C_{22}H_{16}N_4O$; Calc.: C, 74.98; H, 4.58; N, 15.90; Found: 74.58; 4.75; 15.55; Calc.: molar peak $M^+=352$; Found: molar peak $M^+=352$.

The following compounds were obtained analogously to Example 2:

2.1 3-{(Z)-1-[(2-Indazol-6-yl)amino]-1-phenylmethylidene}-2-indolinone×0.75 $H_2O$ Prepared from 1-acetyl-3-{1-ethoxy-1-phenylmethylidene}-2-indolinone and 3 equivalents of 6-amino-indazole in DMF followed by treatment with 1N sodium hydroxide solution in MeOH.

Yield: 42% of theory; Melting point: 307–308° C.; $C_{22}H_{16}N_4O\times 0.75\ H_2O$; Calc.: C, 72.21; H, 4.82; N, 15.31; Found: 72.29; 4.47; 15.62; Calc.: molar peak $M^+=352$; Found: molar peak $M^+=352$.

2.2 3-{(Z)-1-[(2-oxo-indolin-5-yl)amino]-1-phenylmethylidene}-2-indolinone×0.2 $H_2O$ Prepared from 1-acetyl-3-{1-ethoxy-1-phenylmethylidene}-2-indolinone and 3 equivalents of 5-amino-2-indolinone, melting point 194–195° C., in DMF followed by treatment with 1N sodium hydroxide solution in MeOH.

Yield: 54% of theory; Melting point: 288–290° C.; $C_{23}H_{17}N_3O_2\times 0.2\ H_2O$ Calc.: C, 74.45; H, 4.73; N, 11.33; Found: 74.46; 4.67; 11.30; Calc.: molar peak $M^+=367$; Found: molar peak $M^+=367$.

2.3 3-{(Z)-1-[(1,2,3,4-tetrahydro-quinolin-6-yl)amino]-1-phenylmethylidene}-2-indolinone×0.5 $H_2O$ Prepared from 1-acetyl-3-{1-ethoxy-1-phenylmethylidene}-2-indolinone and 3 equivalents of 6-amino-1,2,3,4-tetrahydro-quinoline [prepared by hydrogenation of 6-amino-quinoline] in DMF followed by treatment with 1N sodium hydroxide solution in MeOH.

Yield: 54% of theory; Melting point: 229–230° C.; $C_{24}H_{21}N_3O\times 0.5\ H_2O$; Calc.: C, 76.57; H, 5.89; N, 11.16; Found: 76.73; 5.69; 10.96; Calc.: molar peak $M^+=367$; Found:: molar peak $M^+=367$.

2.4 3-{(Z)-1-[4-(1H-imidazol-4-yl)anilino]-1-phenylmethylidene}-2-indolinone Prepared from 1-acetyl-3-(1-ethoxy-1-phenylmethylidene}-2-indolinone and 1.5 equivalents of 4-(1H-imidazol-4-yl)-aniline in DMF followed by treatment with 1N sodium hydroxide solution in MeOH.

Yield: 68% of theory; Melting point: 280–285° C.; $C_{24}H_{18}N_4O$; Calc.: C, 76.17; H, 4.79; N, 14.80; Found: 75.83; 4.83; 14.62; Calc.: molar peak $M^+=378$; Found: molar peak $M^+=378$.

2.5 3-{(Z)-1-8 4-(1H-imidazol-4-yl)anilino]-1-phenylmethylidene}-5-nitro-2-indolinone×$H_2O$ Prepared from 1-acetyl-3-{1-ethoxy-1-phenylmethylidene-5-nitro-2-indolinone and 1.5 equivalents of 4-(1H-imidazol-4-yl)-aniline in DMF followed by treatment with 1N sodium hydroxide solution in MeOH.

Yield: 59% of theory; Melting point: 308–311° C.; $C_{24}H_{17}N_5O_2\times H_2O$; Calc.: C, 65.30; H, 4.34; N, 15.86; Found: 65.40; 4.29; 15.77; Calc.: molar peak $M^+=423$; Found: molar peak $M^+=423$.

EXAMPLE 3

3-{(Z)-1-[(benzimidazol-5-yl)amino]-1-phenylmethylidene}-2-indolinone×0.5 $H_2O$ 0.307 g (1 mmol) of 1-acetyl-3-{1-ethoxy-1-phenylmethylidene}-2-indolinone and 0.400 mg (3 mmol) of 5-amino-benzimidazole, melting point 169–170° C., are heated in 5 ml DMF for 1.5 hours at 120° C. The mixture is diluted with water and extracted with EtOac. The organic phase is extracted three times with water, dried, filtered and evaporated down in vacuo. To the oily evaporation residue are added 20 ml MeOH and 2 ml of 1N sodium hydroxide solution and the mixture is stirred for 1.5 hours at ambient temperature, during which time a solution is formed. This is evaporated down in vacuo and the evaporation residue is shaken with water/methylene chloride. The undissolved fraction is filtered off, washed with water, digested with EtOac and dried at 80° C.

Yield: 0.19 g (54% of theory); Melting point: 287–289° C.; $C_{22}H_{16}N_4O\times 0.5\ H_2O$; Calc.: C, 73.10; H, 4.74; N, 15.50; Found: 73.43; 4.63; 15.02; Calc.: molar peak $M^+=352$. Found: molar peak $M^+=352$.

The following compounds were obtained analogously to Example 3:

3.1 3-{(Z)-1-[(1-methyl-2-oxo-2,3-dihydro-1H-benzimidazol-5-yl)amino]-1-phenylmethylidene}-2-indolinone Prepared from 1-acetyl-3-{1-ethoxy-1-phenylmethylidene}-2-indolinone and 3 equivalents of crude 5-amino-1-methyl-2-oxo-2,3-dihydro-1H-benzimidazole in DMF followed by treatment with 1N sodium hydroxide solution in MeOH.

Yield: 63% of theory; Melting point: >340° C.; $C_{23}H_{18}N_4O_2$; Calc.: C, 72.24; H, 4.74; N, 14.65; Found: 71.90; 4.76; 14.44; Calc.: molar peak $M^+=382$; Found: molar peak $M^+=382$.

3.2 3-{(Z)-1-[(1-methyl-benzimidazol-6-yl)amino]-1-phenylmethylidene}-2-indolinone Prepared from 1-acetyl-3-{1-ethoxy-1-phenylmethylidene}-2-indolinone and 2 equivalents of 6-amino-1-methyl-benzimidazole, melting point 163–165° C., in DMF followed by treatment with 1N sodium hydroxide solution in MeOH.

Yield: 54% of theory; Melting point: 298–300° C.; $C_{23}H_{18}N_4O$; Calc.: C, 75.39; H, 4.95; N, 15.29; Found: 75.16; 5.00; 15.18; Calc.: molar peak $M^+=366$; Found: molar peak $M^+=366$.

3.3 3-{(Z)-1-[(1-methyl-benzimidazol-6-yl)amino]-1-phenylmethylidene}-5-nitro-2-indolinone×0.4 $H_2O$ Prepared from 1-acetyl-3-{1-ethoxy-1-phenylmethylidene}-5-nitro-2-indolinone and 1.1 equivalents of 6-amino-1-methyl-benzimidazole, melting point 163–165° C., in DMF followed by treatment with 1N sodium hydroxide solution in MeOH.

Yield: 83% of theory; Melting point: 321° C.; $C_{23}H_{17}N_5O_3 \times 0.4 H_2O$; Calc.: C, 65.98; H, 4.28; N, 16.73; Found: 66.29; 4.36; 16.40; Calc.: molar peak $M^+=411$; Found: molar peak $M^+=411$.

3.4 3-{(Z)-1-[(Quinolin-6-yl)amino]-1-phenylmethylidene}-2-indolinone

Prepared from 1-acetyl-3-{1-ethoxy-1-phenylmethylidene}-2-indolinone and 3 equivalents of 6-amino-quinoline in DMF followed by treatment with 1N sodium hydroxide solution in MeOH.

Yield: 50% of theory; Melting point: 271–272° C.; $C_{24}H_{17}N_3O$; Calc.: C, 79.32; H, 4.72; N, 11.56; Found: 78.98; 4.66; 11.68; Calc.: molar peak $M^+=363$; Found: molar peak $M^+=363$.

3.5 3-{(Z)-1-[(2-oxo-1,2,3,4-tetrahydro-quinoline-6-yl)amino]-1-phenylmethylidene}-2-indolinone×0.2 $H_2O$ Prepared from 1-acetyl-3-{1-ethoxy-1-phenylmethylidene}-2-indolinone, 2.5 equivalents of 6-amino-carbostyryl×HCl, melting point >300° C. and 5 equivalents of N-ethyl-diisopropylamine in DMF followed by treatment with 1N sodium hydroxide solution in MeOH.

Yield: 98% of theory; Melting point: 324–325° C.; $C_{24}H_{19}N_3O_2 \times 0.2 H_2O$; Calc.: C, 74.86; H, 5.08; N, 10.91; Found: 74.79; 5.04; 10.93; Calc.: molar peak $M^+=381$; Found: molar peak $M^+=381$.

3.6 3-{(Z)-1-[(2-oxo-1,2,3,4-tetrahydro-quinolin-6-yl)amino]-1-phenylmethylidene}-5-nitro-2-indolinone Prepared from 1-acetyl-3-{1-ethoxy-1-phenylmethylidene}-2-indolinone, 1.3 equivalents of 6-amino-carbostyryl×HCl, melting point >300° C., and 2.5 equivalents of N-ethyl-diisopropylamine in DMF followed by treatment with 1N sodium hydroxide solution in MeOH.

Yield: 85% of theory; Melting point: 310–313° C.; $C_{24}H_{18}N_4O_4$; Calc.: C, 67.60; H, 4.25; N, 13.14; Found: 67.20; 4.35; 12.98; Calc.: molar peak $M^+=426$; Found: molar peak $M^+=426$.

3.7 3-{(Z)-1-[(2-oxo-1,2-dihydro-quinoxalin-7-yl)amino]-1-phenylmethylidene}-2-indolinone×0.5 $H_2O$ Prepared from 1-acetyl-3-{1-ethoxy-1-phenylmethylidene}-2-indolinone and 2.3 equivalents of 7-amino-2-oxo-1,2-dihydro-quinaxolin, melting point >300° C., in DMF followed by treatment with 1N sodium hydroxide solution in MeOH.

Yield: 59% of theory; Melting point: 328–331° C.; $C_{23}H_{16}N_4O_2 \times 0.5 H_2O$; Calc.: C, 70.93; H, 4.40; N, 14.39; Found: 70.91; 4.48; 14.35; Calc.: molar peak $M^+=380$; Found: molar peak $M^+=380$.

3.8 3-{(Z)-1-[(isoquinolin-5-yl)amino]-1-phenylmethylidene}-2-indolinone×0.2 $H_2O$ Prepared from 1-acetyl-3-{1-ethoxy-1-phenylmethylidene}-2-indolinone and 3 equivalents of 5-amino-isoquinoline in toluene followed by treatment with 1N sodium hydroxide solution in MeOH.

Yield: 30% of theory; Melting point: 249–250° C.; $C_{24}H_{17}N_3O \times 0.2 H_2O$; Calc.: C, 78.53; H, 4.78; N, 11.45; Found: 78.75; 4.74; 11.06; Calc.: molar peak $M^+=363$; Found: molar peak $M^+=363$.

3.9 3-{(Z)-1-[(2-Boc-1,2,3,4-tetrahydro-isoquinolin-5-yl)amino]-1-phenylmethylidene}-2-indolinone×0.2 $H_2O$ Prepared from 1-acetyl-3-{1-ethoxy-1-phenylmethylidene}-2-indolinone and 2 equivalents of oily 5-amino-2-Boc-1,2,3,4-tetrahydro-isoquinoline [prepared from 5-amino-1,2,3,4-tetrahydro-quinoline-acetate, melting point 143–145° C.] in DMF followed by treatment with 1N sodium hydroxide solution in MeOH.

Yield: 39% of theory; Melting point: 229–230° C.; $C_{29}H_{29}N_3O_3 \times 0.2 H_2O$; Calc.: C, 73.85; H, 6.28; N, 8.91; Found: 73.79; 6.38; 8.64; Calc.: molar peak $M^+=467$; Found: molar peak $M^+=467$.

3.10 3-{(Z)-1-[4-(1H-imidazol-2-yl)anilino]-1-phenylmethylidene}-2-indolinone×3 $H_2O$ Prepared from 1-acetyl-3-{1-ethoxy-1-phenylmethylidene}-2-indolinone and 2 equivalents of oily 4-(1H-imidazol-2-yl)-aniline [freshly prepared from the corresponding nitro compound, melting point 310° C.] in DMF followed by treatment with 1N sodium hydroxide solution in MeOH.

Yield: 29% of theory; Melting point: 320° C.; $C_{24}H_{18}N_4O \times 3 H_2O$; Calc.: C, 66.65; H, 5.59; N, 12.95; Found: 66.39; 5.24; 12.72; Calc.: molar peak $M^+=378$; Found: molar peak $M^+=378$.

3.11 3-{(Z)-1-[4-(1-methyl-1H-imidazol-2-yl)anilino]-1-phenylmethylidene}-2-indolinone×0.3 $H_2O$ Prepared from 1-acetyl-3-{1-ethoxy-1-phenylmethylidene}-2-indolinone and 3.2 equivalents of 4-(1-methyl-1H-imidazol-2-yl)-aniline, melting point 166–168° C. in DMF followed by treatment with 1N sodium hydroxide solution in MeOH.

Yield: 86% of theory; Melting point: 284–286° C.; $C_{25}H_{20}N_4O \times 0.3\ H_2O$; Calc.: C, 75.46; H, 5.22; N, 14.08; Found: 75.45; 5.13; 13.98; Calc.: molar peak $M^+$=392; Found: molar peak $M^+$=392.

3.12 3-{(Z)-1-[4-(1-methyl-1H-imidazol-2-yl)anilino]-1-phenylmethylidene}-5-nitro-2-indolinone×H₂O Prepared from 1-acetyl-3-{1-ethoxy-1-phenylmethylidene}-5-nitro-2-indolinone and 1.5 equivalents of 4-(1-methyl-1H-imidazol-2-yl)-aniline, melting point 166–168° C., in DMF followed by treatment with 1N sodium hydroxide solution in MeOH.

Yield: 85% of theory; Melting point: 333–334° C.; $C_{25}H_{19}N_5O_2 \times H_2O$; Calc.: C, 65.93; H, 4.65; N, 15.38; Found: 66.35; 4.66; 15.25; Calc.: molar peak $M^+$=437; Found: molar peak $M^+$=437.

3.13 3-{(Z)-1-[4-(1H-imidazol-2-yl)anilino]-1-phenylmethylidene}-5-nitro-2-indolinone×H₂O Prepared from 1-acetyl-3-{1-ethoxy-1-phenylmethylidene}-5-nitro-2-indolinone and 1.5 equivalents of oily 4-(1H-imidazol-2-yl)-aniline [freshly prepared from the corresponding nitro compound, melting point 310° C.] in DMF followed by treatment with 1N sodium hydroxide solution in MeOH.

Yield: 87% of theory; Melting point: 195–198° C.; $C_{24}H_{17}N_5O_3 \times H_2O$; Calc.: C, 65.29; H, 4.34; N, 15.87; Found: 65.15; 4.53; 15.46; Calc.: molar peak $M^+$=423; Found: molar peak $M^+$=423.

3.14 3-{(Z)-1-[3-(1H-imidazol-2-yl)anilino]-1-phenylmethylidene}-2-indolinone×H₂O Prepared from 1-acetyl-3-{1-ethoxy-1-phenylmethylidene}-2-indolinone and 2 equivalents of crude 3-(1H-imidazol-2-yl)-aniline [freshly prepared from the corresponding nitro compound, melting point 198° C.] in DMF followed by treatment with 1N sodium hydroxide solution in MeOH.

Yield: 40% of theory; Melting point: 288° C.; $C_{24}H_{18}N_4O \times H_2O$; Calc.: C, 72.71; H, 5.08; N, 14.13; Found: 72.64; 5.00; 13.82; Calc.: molar peak $M^+$=378; Found: molar peak $M^+$=378.

3.15 3-{(Z)-1-[3-(1H-imidazol-2-yl)anilino]-1-phenylmethylidene}-5-nitro-2-indolinone×0.5 H₂O Prepared from 1-acetyl-3-{1-ethoxy-1-phenylmethylidene}-5-nitro-2-indolinone and 2 equivalents of crude 3-(1H-imidazol-2-yl)-aniline [freshly prepared from the corresponding nitro compound, melting point 198° C.] in DMF followed by treatment with 1N sodium hydroxide solution in MeOH.

Yield: 50% of theory; Melting point: 327–329° C.; $C_{24}H_{17}N_5O_3 \times 0.5\ H_2O$; Calc.: C, 66.65; H, 4.19; N, 16.20; Found: 67.01; 4.26; 16.20; Calc.: molar peak $M^+$=423; Found: molar peak $M^+$=423.

3.16 3-{(Z)-1-[3-(1-methyl-1H-imidazol-2-yl)anilino]-1-phenylmethylidene}-2-indolinone×0.3 H₂O Prepared from 1-acetyl-3-{1-ethoxy-1-phenylmethylidene}-2-indolinone and 2 equivalents of crude 3-(1-methyl-1H-imidazol-2-yl)-aniline [freshly prepared from the corresponding nitro compound] in DMF followed by treatment with 1N sodium hydroxide solution in MeOH.

Yield: 88% of theory; Melting point: 299–300° C.; $C_{25}H_{20}N_4O \times 0.3\ H_2O$; Calc.: C, 75.46; H, 5.22; N, 14.08; Found: 75.61; 5.24; 14.15; Calc.: molar peak $M^+$=392; Found: molar peak $M^+$=392.

3.17 3-{(Z)-1-[3-(1-methyl-1H-imidazol-2-yl)anilino]-1-phenylethylidene}-5-nitro-2-indolinone×0.3 H₂O Prepared from 1-acetyl-3-{1-ethoxy-1-phenylmethylidene}-5-nitro-2-indolinone and 2 equivalents of crude 3-(1-methyl-1H-imidazol-2-yl)-aniline [freshly prepared from the corresponding nitro compound] in DMF followed by treatment with 1N sodium hydroxide solution in MeOH.

Yield: 81% of theory; Melting point: 287–289° C.; $C_{25}H_{19}N_5O_3 \times 0.3\ H_2O$; Calc.: C, 67.80; H, 4.44; N, 15.82; Found: 67.80; 4.46; 15.56; Calc.: molar peak $M^+$=437; Found: molar peak $M^+$=437.

3.18 3-{(Z)-1-[4-((pyrrolidin-1-yl)methyl)anilino]-1-phenylmethylidene}-5-nitro-2-indolinone Prepared from 1-acetyl-3-{1-ethoxy-1-phenylmethylidene}-5-nitro-2-indolinone and 2 equivalents of 4-(1-pyrrolidinyl-methyl)-aniline, melting point 45–50° C. in DMF followed by treatment with 1N sodium hydroxide solution in MeOH.

Yield: 54% of theory; Melting point: 227° C.; $C_{26}H_{24}N_4O_3$; Calc.: C, 70.89; H, 5.49; N, 12.72; Found: 70.64; 5.61; 12.67; Calc.: molar peak $M^+$=440; Found: molar peak $M^+$=440.

3.19 Mixture of 3-{(Z)-1-[(2-ethyl-1,2,3,4-tetrahydro-isoquinolin-6-yl)amino]-1-phenylmethylidene}-5-nitro-2-indolinone and 3-{(Z)-1-[(2-ethyl-1,2,3,4-tetrahydro-isoquinolin-7-yl)amino]-1-phenylmethylidene}-5-2-indolinone×0.3 H₂O Prepared from 1-acetyl-3-{1-ethoxy-1-phenylmethylidene}-5-nitro-2-indolinone, 1.5 equivalents of a mixture of 6- and 7-amino-2-ethyl-1,2,3,4-tetrahydro-isoquinoline×2 HCl, melting point 145–150° C., and 3 equivalents of N-ethyl-diisopropylamine in DMF followed by treatment with 1N sodium hydroxide solution in MeOH.

Yield: 32% of theory; Melting point: 234–236° C.; $C_{26}H_{24}N_4O_3 \times 0.3\ H_2O$; Calc.: C, 70.02; H, 5.56; N, 12.57; Found: 69.84; 5.30; 12.73; Calc.: molar peak $M^+$=440; Found: molar peak $M^+$=440.

3.20 Mixture of 3-{(Z)-1-[(2-ethyl-1,2,3,4-tetrahydro-isoquinolin-6-yl)amino]-1-phenylmethylidene}-2-indolinone and 3-{(Z)-1-[(2-ethyl-1,2,3,4-tetrahydro-isoquinolin-7-yl)amino]-1-phenylmethylidene}-2-indolinone×0.4 H₂O Prepared from 1-acetyl-3-{1-ethoxy-1-phenylmethylidene}-2-indolinone, 1.5 equivalents of a mixture of 6- and 7-amino-2-ethyl-1,2,3,4-tetrahydro-isoquinoline×2 HCl, melting point 145–150° C., and 3 equivalents of N-ethyl-diisopropylamine in DMF followed by treatment with 1N sodium hydroxide solution in MeOH.

Yield: 48% of theory; Melting point: 222–223° C.; $C_{26}H_{25}N_3O \times 0.4\ H_2O$; Calc.: C, 77.55; H, 6.46; N, 10.43; Found: 77.70; 6.32; 10.29; Calc.: molar peak $M^+$=395; Found: molar peak $M^+$=395.

EXAMPLE 4

3-{(Z)-1-[(2-ethoxycarbonylmethyl-1,3-dioxo-isoindolin-5-yl)amino]-1-phenylmethylidene}-2-indolinone×0.5 H₂O 0.80 g (3 mmol) of 3-{1-ethoxy-1-phenylmethylidene}-2-indolinone and 0.87 g (3.5 mmol) of 5-amino-N- ethoxycarbonylmethyl-phthalimide, melting point 172–173° C., are heated in 10 ml of DMF for two hours at 120° C., at 140° C. and at 150° C. The mixture is poured onto ice water and extracted with EtOac. The organic phase is washed with water, dried, filtered and evaporated down in vacuo. The semisolid evaporation residue is gently heated in 15 ml of EtOH, whilst crystallisation takes place. The crystals are filtered and dried at 80° C.

Yield: 0.39 g (28% of theory); Melting point: 263–266° C.; $C_{27}H_{21}N_3O_5 \times 0.5 H_2O$; Calc.: C, 68.06; H, 4.65; N, 8.82; Found: 68.14; 4.62; 9.13; Calc.: molar peak $M^+=467$; Found: molar peak $M^+=467$.

The following compounds were obtained analogously to Example 4:

4.1 3-{(Z)-1-[(2-(3-ethoxycarbonyl-propyl)-1,3-dioxo-isoindolin-5-yl)amino]-1-phenylmethylidene}-2-indolinone Prepared from 3-{1-ethoxy-1-phenylmethylidene}-2-indolinone and 1.2 equivalents of 5-amino-N-(3-ethoxycarbonyl-propyl)-phthalimide, melting point 78–80° C., in DMF by heating to 140° C. for 8 hours and crystallisation from EtOH.

Yield: 26% of theory; Melting point: 195–197° C.; $C_{29}H_{25}N_3O_4$; Calc.: C, 70.29; H, 5.08; N, 8.48; Found: 69.98; 5.09; 8.70; Calc.: molar peak $M^+=495$; Found: molar peak $M^+=495$.

4.2 3-{(Z)-1-[4-(2-amino-5-methyl-1H-imidazol-4-yl)anilino]-1-phenylmethylidene}-5-nitro-2-indolinone×1.5 $H_2O$ Prepared from 3-{1-ethoxy-1-phenylmethylidene}-5-nitro-2-indolinone and 1.3 equivalents of 4-(2-amino-5-methyl-1H-imidazol-4-yl)aniline [released from 4-(2-amino-5-methyl-1H-imidazol-4-yl)aniline×$H_2SO_4$×0.7 $H_2O$, melting point 312–315° C.] in DMF by heating to 100° C. for 2 hours and purification by column chromatography on silica gel with the eluant methylene chloride/MeOH/conc. ammonia (10:2:0.01).

Yield: 8.5% of theory; Melting point: 250° C.; $C_{25}H_{20}N_6O_3 \times 1.5 H_2O$; Calc.: C, 62.62; H, 4.83; N, 17.53; Found: 63.05; 4.70; 17.17; Calc.: molar peak $M^+=452$; Found: molar peak $M^+=452$.

4.3 3-{(Z)-1-[(2-acetyl-1,2,3,4-tetrahydro-isoquinolin-7-yl)amino]-1-phenylmethylidene}-2-indolinone×0.2 $H_2O$ Prepared from 3-{1-ethoxy-1-phenylmethylidene}-2-indolinone and 1.05 equivalents of an oily mixture of 2-acetyl-6-amino-1,2,3,4-tetrahydro-isoquinoline and 2-acetyl-7-amino-1,2,3,4-tetrahydro-isoquinoline in DMF by heating to 120° C. for 7 hours, pouring into water, extracting with EtOac and crystallisation from EtOH.

Yield: 24% of theory; Melting point: 252–253° C.; DC-$R_f$=0.29 [silica gel; methylene chloride/MeOH/conc. ammonia (9:1:0.1)]; $C_{26}H_{23}N_3O_2 \times 0.2 H_2O$; Calc.: C, 75.59; H, 5.71; N, 10.17; Found: 75.79; 5.58; 10.18; Calc.: molar peak $M^+=409$; Found: molar peak $M^+=409$.

4.4 Mixture of 3-{(Z)-1-[(2-acetyl-1,2,3,4-tetrahydro-isoquinolin-6-yl)amino]-1-phenylmethylidene}-5-nitro-2-indolinone (about 40%) and 3-{(Z)-1-[(2-acetyl-1,2,3,4-tetrahydro-isoquinolin-7-yl)amino]-1-phenylmethylidene}-5-nitro-2-indolinone (about 60%)

Prepared from 3-{-ethoxy-1-phenylmethylidene}-5-nitro-2-indolinone and 1.15 equivalents of an oily mixture of 2-acetyl-6-amino-1,2,3,4-tetrahydro-isoquinoline and 2-acetyl-7-amino-1,2,3,4-tetrahydro-isoquinoline in DMF by heating to 100° C. for 2.5 hours, pouring into water, extracting with EtOac and stirring the evaporation residue with EtOH.

Yield: 80% of theory; Melting point: 271–274° C.; DC-$R_f$=0.34 and 0.29 [silica gel; methylene chloride/MeOH/conc. ammonia (9:1:0.1)]; $C_{26}H_{22}N_4O_4$; Calc.: C, 68.69; H, 4.88; N, 12.32; Found: 68.38; 5.07; 12.21.

4.5 3-{(Z)-1-[4-(2-amino-1H-thiazol-4-yl)anilino]-1-phenylmethylidene}-5-nitro-2-indolinone×0.8 thiourea (a) 2-amino-4-(4-amino-phenyl)-thiazole Prepared by 2 hours' hydrogenation of 2-amino-4-(4-nitro-phenyl)-thiazole (melting point: 287–291° C.; prepared from ω-bromo-4-nitro-acetophenone and thiourea) in DMF on palladium/charcoal (10%) at 20° C.

Yield (crude): 100% of theory; Melting point: 120° C.

(b) 3-{(Z)-1-[4-(2-amino-1H-thiazole-4-yl)anilino]-1-phenylmethylidene}-5-nitro-2-indolinone×0.8 thiourea Prepared from 3-{1-ethoxy-1-phenylmethylidene}-5-nitro-2-indolinone and 2 equivalents of the aniline derivative obtained in (a) in DMF by heating to 110° C. for 1 hour, pouring into water and washing the precipitate with MeOH and ether.

Yield: 87% of theory; Melting point: 270° C.; $C_{24}H_{17}N_5O_3S \times 0.8\ H_2N-CS-NH_2$; Calc.: C, 57.68; H, 3.94; N, 17.91; Found: 57.24; 3.72; 17.82; Calc.: molar peak $M^+=455$; Found: molar peak $M^+=455$.

4.6 3-{(Z)-1-[4-((imidazol-1-yl)methyl)anilino]-1-phenylmethylidene}-5-nitro-2-indolinone Prepared from 3-{1-ethoxy-1-phenylmethylidene}-5-nitro-2-indolinone and 1.5 equivalents of 4-(imidazol-1-yl)methyl-aniline (melting point: 128–130° C.) in DMF (120° C., 1 hour), pouring into water and washing the precipitate with MeOH and ether. Yield: 90% of theory;

Melting point: 355° C.; $C_{25}H_{19}N_5O_3$; Calc.: C, 68.64; H, 4.38; N, 16.01; Found: 68.35; 4.51; 15.92; Calc.: molar peak $M^+=437$; Found: molar peak $M^+=437$.

4.7 Mixture of 3-{(Z)-1-[4-((2-oxo-pyrrolidin-1-yl)methyl)anilino]-1-phenylmethylidene}5-nitro-2-indolinone×0.5 $H_2O$ (~80%) and 3-{(Z)-1-[3-((2-oxo-pyrrolidin-1-yl)methyl)anilino]-1-phenylmethylidene}-5-nitro-2-indolinone×0.5 $H_2O$ (~20%)

(a) Mixture of N-(4-nitro-benzyl)-2-pyrrolidinone (~80%) and (b) N-(3-nitro-benzyl)-2-pyrrolidinone (~20%)

Prepared analogously to Example D by reacting N-benzyl-2-pyrrolidinone with ammonium nitrate in concentrated sulphuric acid and subsequent crystallisation from petroleum ether/ether.

Yield: 68% of theory; Melting point: 55–75° C.

(b) Mixture of 4-(2-oxo-pyrrolidin-1-yl)methyl-aniline (~80%) and 3-(2-oxo-pyrrolidin-1-yl)methyl-aniline (~20%)

Prepared by hydrogenation of the mixture of the nitro compounds obtained in (a) on rhodium/charcoal (5%) in EtOH/methylene chloride (1:1) (20° C., 3.5 bar, 3 hours).

Yield: 71% of theory; Melting point: 110–115° C.

(c) Mixture of 3-{(Z)-1-[4-((2-oxo-pyrrolidin-1-yl)methyl)anilino]-1-phenylmethylidene}-5-nitro-2-indolinone×0.5 $H_2O$ (~80%) and (Z)-1-[3-((2-oxo-pyrrolidin-1-yl)methyl)anilino]-1-phenylmethylidene}-5-nitro-2-indolinone×0.5 $H_2O$ (~20%)

Prepared from 3-{1-ethoxy-1-phenylmethylidene}-5-nitro-2-indolinone and 1.5 equivalents of the mixture of the aniline compounds obtained in (b) in DMF (110° C., for 2 hours), with the addition of water and washing the precipitate with isopropanol and ether.

Yield: 85% of theory; Melting point: 300–303° C.; $C_{26}H_{22}N_4O_4 \times 0.5\ H_2O$; Calc.: C, 67.37; H, 5.00; N, 12.09; Found: 67.23; 5.06; N, 12.49; Calc.: molar peak $M^+=454$; Found: molar peak $M^+=454$.

4.8 3-{(Z)-1-[(2-Boc-1,2,3,4-tetrahydro-isoquinolin-6-yl)amino-1-phenylmethylidene}-5-nitro-2-indolinone Prepared from 3-{1-ethoxy-1-phenylmethylidene}-5-nitro-2-indolinone and 1.1 equivalents of an oily mixture of 2-Boc-6-amino-1,2,3,4-tetrahydro-isoquinoline [prepared from 6-amino-isoquinoline, melting point 218–220° C., by catalytic hydrogenation to obtain 6-amino-1,2,3,4-tetrahydro-isoquinoline (melting point: 69–71° C.) and subsequent reaction with 0.9 equivalents of di-tert.butyl pyrocarbonate (=(Boc)$_2$O)] in DMF by heating to 100° C. for 3.5 hours, pouring into water, filtering and washing the precipitate with water and EtOH.

Yield: 82% of theory; Melting point: 258–259° C.; $C_{29}H_{28}N_4O_5$; Calc.: C, 67.96; H, 5.51; N, 10.93; Found: 68.07; 5.46; N, 10.96; Calc.: molar peak $M^+=512$; Found: molar peak $M^+=512$.

4.9 3-{(Z)-1-[4-(2-(pyrrolidin-1-yl)ethyl)anilino]-1-phenylmethylidene}-5-nitro-2-indolin×0.5 $H_2O$ Prepared from 3-(1-ethoxy-1-phenylmethylidene)-5-nitro-2-indolinone and 2 equivalents of 4-(2-(1-pyrrolidinyl)ethyl-aniline [oil; prepared from 2-[4-nitro-phenyl) ethylbromide, melting point 68–70° C., by reaction with pyrrolidine and subsequent catalytic hydrogenation of the oily 1-[2-(4-nitrophenyl)ethyl]-pyrrolidine] in DMF (for 2 hours, 100° C.), pouring into water, filtering the precipitate and washing with water, EtOH and ether.

Yield: 80% of theory; Melting point: 227–230° C.; $C_{27}H_{26}N_4O_3 \times 0.5\ H_2O$; Calc.: C, 69.96; H, 5.87; N, 12.09; Found: 70.18; 5.90; N, 12.55; Calc.: molar peak $M^+=454$; Found: molar peak $M^+=454$.

4.10 3-{(Z)-1-[(2-methyl-4,4-dimethyl-1,3-dioxo-1,2,3,4-tetrahydro-isoquinolin-7-yl)amino]-1-phenylmethylidene}-5-nitro-2-indolinone Prepared from 3-(1-ethoxy-1-phenylmethylidene)-5-nitro-2-indolinone and 1.5 equivalents of 2-methyl-7-amino-4,4-dimethyl-1,3-dioxo-1,2,3,4-tetrahydro-isoquinoline, melting point 169–171° C., in DMF by heating to 120° C. for 1 hour, pouring into water, filtering and washing the precipitate with MeOH and ether.

Yield: 76% of theory; Melting point: 306–310° C.; $C_{27}H_{22}N_4O_5$; Calc.: C,67.21; 114.60; N, 11.61; Found: 66.83; 4.62; N, 11.51; Calc.: molar peak $M^+=482$; Found: molar peak $M^+=482$.

4.11-3{(Z)-1-[4-((2,5-dioxo-pyrrolidin-1-yl)methyl) anilino]-1-phenylmethylidene}-5-nitro-2-indolinone Prepared from 3-(1-ethoxy-1-phenylmethylidene)-2-indolinone and 1.3 equivalents of crude 4-(2,5-dioxo-pyrrolidin-1-yl)methyl)aniline [oil; freshly prepared from the corresponding nitro compound] in DMF (120° C.; 1.5 hours), pouring into water, filtering and washing the precipitate with MeOH and ether.

Yield: 79% of theory; Melting point: 260–265° C.; $C_{26}H_{20}N_4O_5$; Calc.: C, 66.66; H, 4.30; N, 14.96; Found: 66.27; 4.37; N, 11.80; Calc.: molar peak $M^+=468$; Found: molar peak $M^+=468$.

4.12 3-{(Z)-1-[4-((1-methyl-2,4-dioxo-imidazolidin-5-(E/Z)-ylidene)methyl)anilino]-1-phenylmethylidene}-5-nitro-2-indolinone×$H_2O$ Prepared from 3-(1-ethoxy-1-phenylmethylidene)-5-nitro-2-indolinone and 3 equivalents of crude (E/Z)-4-amino-benzylidene-(1-methyl-hydantoin [freshly prepared from the corresponding nitro compound (melting point: 210–220° C.; E/Z mixture) by catalytic hydrogenation on Raney nickel in EtOH/Cl$_2$Cl$_2$ (1:1)] in DMF (120° C., for 1.5 hours), pouring into water, filtering and washing the precipitate with MeOH and ether.

Yield: 53% of theory; Melting point: 390° C.; DC-R$_f$= 0.58 and 0.52 (silica gel; EtOac); $C_{26}H_{19}N_5O_5 \times H_2O$; Calc.: C, 62.52; H, 4.24; N, 14.02; Found: 62.22; 4.25; N, 13.66; Calc.: molar peak $M^+=481$; Found: molar peak $M^+=481$.

4.13 3-{(Z)-1-[4-(1,2,4-triazol-1-yl)methyl)anilino]-1-phenylmethylidene}-5-nitro-2-indolinone Prepared from 3-(1-ethoxy-1-phenylmethylidene)-5-nitro-2-indolinone and 3 equivalents of crude 4-[(1,2,4-triazol-1-yl)methyl]-aniline [freshly prepared from the corresponding nitro compound (melting point: 100–103° C.) by catalytic hydrogenation on Raney nickel in EtOH] in DMF (120° C., for 2 hours), pouring into water, filtering and washing the precipitate with isopropanol and ether.

Yield: 84% of theory; Melting point: 289–294° C.; $C_{24}H_{18}N_6O_3$; Calc.: molar peak $M^+=438$; Found: molar peak $M^+=438$.

4.14 3-{(Z)-1-[4-(2-Butyl-1H-imidazol-4-yl) anilino]-1-phenyl-methylidene}-5-indolinone Prepared from 4-(2-butyl-1H-imidazol-4-yl)aniline and 3-(1-ethoxy-1-phenylmethylidene)-5-nitro-2-indolinone in DMF. Yield: 58% of theory;

melting point: 175–180° C.; $C_{28}H_{25}N_5O_3$; Calc.: molar peak $M^+=479$; Found: molar peak $M^+=479$; $C_{28}H_{25}N_5O_3 \times 0.3\ H_2O$ (484.94) Calc.: C, 69.34; H, 5.32; N, 14.44; Found: 69.60; 5.52; 13.94.

4.15 3-{(Z)-1-[4-(2-Pentyl-1H-imidazol-4-yl) anilino]-1-phenyl-methylidene)-5-nitro-2-indolinone Prepared from 4-(2-pentyl-1H-imidazol-4-yl)aniline and 3-(1-ethoxy-1-phenylmethylidene)-5-nitro-2-indolinone in DMF. Yield: 50% of theory;

melting point: 170–175° C.; $C_{29}H_{27}N_5O_3$ (493.57); Calc.: molar peak $M^+=493$; Found: molar peak $M^+=493$; $C_{29}H_{27}N_5O_3 \times 0.3\ H_2O$ (498.96); Calc.: C, 69.80; H, 5.58; N, 14.04; Found: 69.75; 5.98; 13.80.

4.16 3-{(Z)-1-[4-(2-Cyclohexyl-1H-imidazol-4-yl) anilino]-1-phenylmethylidene}-5-nitro-2-indolinone Prepared from 4-(2-cyclohexyl-1H-imidazol-4-yl)aniline and 3-(1-ethoxy-1-phenylmethylidene)-5-nitro-2-indolinone in DMF.

Yield: 90% of theory; Melting point: 290–295° C.; $C_{30}H_{27}N_5O_3$ (505.58); Calc.: molar peak $(M+H)^+=506$; Found: molar peak $(M+H)^+=506$; $C_{29}H_{27}N_5O_3 \times 1.0$ DMF (578.7); Calc.: C, 68.50; H, 5.92; N, 14.52; Found: 68.50; 4.29; 14.52.

4.17 3-{(Z) 1-[4-(2-Phenyl-1H-imidazol-4-yl) anilino]-1-phenyl-methylidene}-5-nitro-2-indolinone Prepared from 4-(2-phenyl-1H-imidazol-4-yl)aniline and 3-(1-ethoxy-1-phenylmethylidene)-5-nitro-2-indolinone in DMF.

Yield: 98% of theory; Melting point: 230–235° C.; $C_{30}H_{21}N_5O_3$ (499.53); Calc.: molar peak M$^+$=499; Found: molar peak M$^+$=499; $C_{30}H_{21}N_5O_3 \times 1.0$ $H_2O$ (517.53); Calc.: C, 69.62; H, 4.48; N, 13.53; Found: 69.26; 4.85; 14.43.

4.18 3-{(Z)-1-[4-(2-Phenylmethyl-1H-imidazol-4-yl)anilino]-1-phenylmethylidene}-5-nitro-2-indolinone Prepared from 4-(2-phenylmethyl-1H-imidazol-4-yl)aniline and 3-(1-ethoxy-1-phenylmethylidene)-5-nitro-2-indolinone in DMF.

Yield: 38% of theory; Melting point: 200–205° C.; $C_{31}H_{23}N_5O_3$ (513.56); Calc.: molar peak (M+H)$^+$=514; Found: molar peak (M+H)$^+$=514; DC-R$_f$=0.6 (silica gel; methylene chloride/methanol 10:1).

4.19 3-{(Z)-1-[4-(2,5-Dihydro-pyrrol-1-yl-methyl)anilino]1-phenylmethylidene}-5-nitro-2-indolinone Prepared from 4-(2,5-dihydro-pyrrol-1-ylmethyl)aniline and 3-(1-ethoxy-1-phenylmethylidene)-5-nitro-2-indolinone in DMF.

Yield: 41% of theory; melting point: 205–207° C.; $C_{26}H_{22}N_4O_3$ (438.49); Calc.: molar peak M$^+$=438; Found: molar peak M$^+$=438; Calc.: C, 71.22; H, 5.06; N, 12.78; Found: 70.62; 5.26; 12.52.

4.20 3-{(Z)-1-[4-(3-hydroxypyrrolidin-1-yl-methyl)anilino]-1-phenylmethylidene}-5-nitro-2-indolinone Prepared from 4-(3-hydroxypyrrolidin-1-yl-methyl)aniline and 3-(1-ethoxy-1-phenylmethylidene)-5-nitro-2-indolinone in DMF.

Yield: 34% of theory; Melting point: 120–125° C.; $C_{26}H_{24}N_4O_4$ (456.51); Calc.: molar peak M$^+$=456; Found: molar peak M$^+$=456; $C_{26}H_{24}N_4O_4 \times H_2O$ (474.52); Calc.: C, 65.81; H, 5.52; N, 11.81; Found: 66.16; 5.61; 11.59.

4.21 3-{(Z)-1-[4-(2-Methoxycarbonyl-pyrrolidin-1-yl-methyl)anilino]-1-phenylmethylidene}-5-nitro-2-indolinone Prepared from 4-(2-methoxycarbonyl-pyrrolidin-1-ylmethyl)-aniline and 3-(1-ethoxy-1-phenylmethylidene)-5-nitro-2-indolinone in DMF.

Yield: 49% of theory; Melting point: 189–191° C.; $C_{28}H_{26}N_4O_5$ (498.54); Calc.: molar peak M$^+$=498; Found: molar peak M$^+$=498; Calc.: C, 67.46; H, 5.26; N, 11.24; Found: 67.39; 5.35; 11.13.

4.22 3-{Z)-1-[4-((2-Hydroxycarbonyl)-pyrrolidin-1-yl-methyl)-anilino]-1-phenylmethylidene}-5-nitro-2-indolinone A solution of 299 mg (0.60 mmol) of 4-[(2-methoxycarbonyl)-pyrrolidin-1-ylmethyl]-aniline and 1.2 ml of 1N sodium hydroxide solution is stirred in 10 ml of methanol for 13 hours at 60° C. Then the solvent is eliminated in vacuo. The residue is taken up in water and washed once with ethyl acetate. Then 1.2 ml of 1N hydrochloric acid are added and the resulting mixture is stirred for 2 hours at ambient temperature. The precipitate is suction filtered and dried in vacuo.

Yield: 72% of theory; Melting point: 265–266° C.; $C_{27}H_{24}N_4O_5$ (484.52); Calc.: molar peak (M+Na)$^+$=507; Found: molar peak (M+Na)$^+$=507; $C_{27}H_{24}N_4O_5 \times H_2O$ (502.53); Calc.: C,64.53; H, 5.21; N, 11.15; Found: 64.23; 5.53; 11.15.

EXAMPLE 5

3-{(Z)-1-[3-(1H-imidazol-4-yl)anilino]-1-phenylmethylidene}-2-indolinone×0.5 $H_2O$ 1.02 g of 60% 1-acetyl-3-{1-ethoxy-1-phenylmethylidene}-2-indolinone (2.2 mmol), 0.70 g (3.0 mmol) of (1H-imidazol-4-yl)-aniline×2 HCl (melting point: 296° C.) and 0.91 ml (6.5 mmol) of triethylamine are heated in 8 ml of DMF for 2 hours at 100° C. After cooling to ambient temperature 1.0 ml (10 mmol) of piperidine are added and the mixture is stirred overnight. It is poured onto water. The precipitate formed is purified by column chromatography on silica gel with the eluant methylene chloride/MeOH (20:1).

Yield: 0.67 g (89% of theory); Melting point: 215–218° C. (from ether); $C_{24}H_{18}N_4O \times 0.5$ $H_2O$; Calc.: C, 74.40; H, 4.94; N, 14.46; Found: 74.18; H, 5.35; 14.02; Calc.: molar peak M$^+$=378; Found: molar peak M$^+$=378.

The following compounds were obtained analogously to Example 5:

5.1 3-{(Z)-1-[2-(1H-imidazol-4-yl)anilino]-1-phenylmethylidene}-5-nitro-2-indolinone×0.3 $H_2O$ Prepared from 1-acetyl-3-{1-ethoxy-1-phenylmethylidene}-5-nitro-2-indolinone and 1.5 equivalents of 2-(1H-imidazol-4-yl)-aniline (oil) in DMF (for 2 hours at 100° C.), subsequent treatment with piperidine and purification by column chromatography on $Al_2O_3$ (activity stage II—II) with the eluant methylene chloride/EtOH (20:1).

Yield: 24.6% of theory; Melting point: 240–245° C.; $C_{24}H_{17}N_5O_3 \times 0.3$ $H_2O$; Calc.: C, 67.21; H, 4.14; N, 16.33; Found: 67.26; 4.33; 15.92; Calc.: molar peak M$^+$=423; Found: molar peak M$^+$=423.

5.2 3-{(Z)-1-[4-(2-amino-1H-imidazol-4-yl)anilino]-1-phenylmethylidene}-5-nitro-2-indolinone×0.7 $H_2O \times 0.7$ EtOH.

Prepared from 1-acetyl-3-{1-ethoxy-1-phenylmethylidene}-5-nitro-2-indolinone and 1.0 equivalent of crude 4-(2-amino-1H-imidazol-4-yl)-aniline [freshly prepared from 2-amino-4-(4-nitro-phenyl)-1H-imidazole] in DMF (for 2 hours at 100° C.), subsequent treatment with piperidine and purification by column chromatography on $Al_2O_3$ (activity stage II—II).

Yield: 29.3% of theory; Melting point: 220–225° C.; $C_{24}H_{18}N_6O_3 \times 0.7$ $H_2O \times 0.7$ EtOH; Calc.: C, 63.12; H, 4.92; N, 17.39; Found: 63.19; 4.96; 17.03; Calc.: molar peak M$^+$=438; Found: molar peak M$^+$=438.

5.3 Mixture of 3-{(Z)-1-[4-((1-Boc-imidazolin-2-yl)methyl)anilino]-1-phenylmethylidene}-5-nitro-2-indolinone (75%) and 3-{(Z)-1-[3-((1-Boc-imidazolin-2-yl)methyl)anilino]-1-phenylmethylidene}-5-nitro-2-indolinone (25%)

Prepared from 1-acetyl-3-(1-ethoxy-1-phenylmethylidene)-5-nitro-2-indolinone and 1.5 equivalents of a crude mixture of 4-[(1-Boc-imidazolin-2-yl)methyl]aniline and 3-[(1-Boc-imidazolin-2-yl)methyl]aniline [prepared from 2-benzyl-imidazoline x hydrochloride by reacting with ammonium nitrate in concentrated sulphuric acid, acylation of the resulting (70:30) mixture of 2-(4-nitrobenzyl)- and 2-(3-nitro-benzyl)-imidazoline with di-tert.butyl pyrocarbonate and subsequent catalytic hydrogenation] in DMF (120° C., 1 hour), treatment with piperidine and finally purification by column chromatography on silica gel with toluene/EtOac/EtOH (4:2:1) as eluant.

Yield: 56% of theory; Melting point: 200° C.; $C_{30}H_{29}N_5O_5$; Calc.: C, 66.02; H, 5.54; N, 13.27; Found: 66.44; 5.38; 12.91; Calc.: molar peak $M^+$=539; Found: molar peak $M^+$=539.

EXAMPLE 6

3-{(Z)-1-[4-((2,4-dioxo-imidazolidin-5-yl)methyl) anilino]-1-phenylmethylidene}-5-nitro-2-indolinone×0.3 $H_2O$ (I) and 3-{(Z)-1-[4-((2,4-dioxo-imidazolidin-5-ylidene)methyl)anilino]-1-phenylmethylidene}-5-nitro-2-indolinone×$H_2O$ (II)

(a) 4-amino-benzylidene-hydantoin (A) and 4-amino-benzyl-hydantoin (B)

Crude 4-nitro-benzylidene-hydantoin, melting point 310° C. (prepared by refluxing 4-nitro-benzaldehyde with hydantoin at 155° C. for 8 hours in glacial acetic acid in the presence of sodium acetate) is hydrogenated in DMF on palladium/charcoal (10%) at 20° C. and 3.5 bar. After evaporation in vacuo and digesting with $CH_2Cl_2$/MeOH (7:1) a product is obtained, melting point 185–190° C., which according to DC (silica gel; $CH_2Cl_2$/MeOH (5:1)) and MS consists of (A) ($R_f$=0.60; $M^+$=203), a great deal of (B) ($R_f$=0.52; $M^+$=205) and an unknown third substance (C) ($R_f$=0.39).

(b) (I) and (II)

0.70 g (2 mmol) of 1-acetyl-3-{1-ethoxy-1-phenylmethylidene}-5-nitro-2-indolinone and 0.61 g (~3 mmol) of the product obtained in (a), melting point 185–190° C., are heated in 6 ml of DMF for 1 hour at 120° C. After cooling to 20° C., 1 ml of piperidine are added and the mixture is stirred for 1 hour. Water and solid sodium chloride are added, the precipitate is filtered off and purified by column chromatography on silica gel with the eluant $CH_2Cl_2$/MeOH (10:1).

First (I) is eluted ($R_f$=0.68):

3-{(Z)-1-[4-((2,4-dioxo-imidazolidin-5-yl)methyl) anilino]-1-phenylmethylidene}-5-nitro-2-indolinone×0.3 $H_2O$ (I)

Yield: 0.105 g (11.2% of theory); Melting point: 310–315° C.; $C_{25}H_{19}N_5O_5$×0.3 $H_2O$; Calc.: C, 63.23; H, 4.16; N, 14.75; Found: 63.18; 4.26; 14.72; Calc.: molar peak $M^+$=469; Found: molar peak $M^+$=469.

Then (II) is eluted ($R_f$=0.55):

3-{(Z)-1-[4-((2,4-dioxo-imidazolidin-5-ylidene) methyl)anilino]-1-phenylmethylidene}-5-nitro-2-indolinone×$H_2O$ (II)

Yield: 0.045 g (4.8% of theory); Melting point: 280–285° C.; $C_{25}H_{17}N_5O_5$×$H_2O$; Calc.: C, 61.85; H, 3.94; N, 14.43; Found: 61.56; 4.16; 14.32; Calc.: molar peak $M^+$=467; Found: molar peak $M^+$=467.

EXAMPLE 7

3-{(Z)-1-[4-((2,4-dioxo-imidazolidin-5-ylidene) methyl)anilino]-1-phenylmethylidene}-5-nitro-2-indolinone×0.2 $H_2O$ (a) 4-amino-benzylidene-hydantoin (A)

To 3 g (12.9 mmol) of crude 4-nitro-benzylidene-hydantoin, melting point 300° C. (prepared as described in Example 6 under (a)) in 50 ml 80% acetic acid are added 3 g of iron powder at 100°. After 30 minutes the mixture is filtered over kieselguhr and the filtrate is evaporated down in vacuo. The evaporation residue is divided between EtOac and dilute aqueous ammonia solution; before the separation of the phases the mixture is filtered once more through kieselguhr. The organic phase is washed with water, dried, filtered and evaporated down in vacuo. The yellow foam obtained (0.80 g; 30.6% of theory) predominantly contains 4-amino-benzylidene-hydantoin (A) ($R_f$=0.55), but no 4-amino-benzyl-hydantoin (B) ($R_f$=0.48), according to DC (silica gel; toluene/EtOac/EtOH (4:2:1)).

(b) 3-{(Z)-1-[4-((2,4-dioxo-imidazolidin-5-ylidene)methyl) anilino]-1-phenylmethylidene}-5-nitro-2-indolinone×0.2 $H_2O$ 0.92 g (2.6 mmol) of 1-acetyl-3-{1-ethoxy-1-phenylmethylidene}-5-nitro-2-indolinone and 0.80 g (3.9 mmol) of the 4-amino-benzylidene-hydantoin obtained in (a) are heated in 8 ml of DMF for 2 hours at 120° C. After cooling to 20° C. 1 ml of piperidine are added and the mixture is stirred for 1 hour. The yellow precipitate formed is filtered off, washed with MeOH and ether and dried at 80° C.

Yield: 0.54 g (44.3% of theory); Melting point: 370° C.; DC-$R_f$=0.52 (silica gel; methylene chloride/methanol (10:1)); $C_{25}H_{17}N_5O_5$×0.2 $H_2O$; Calc.: C, 63.69; H, 3.72; N, 14.86; Found: 63.70; 4.05; 14.69; Calc.: molar peak $M^+$=467; Found: molar peak $M^+$=467.

The following was obtained analogously to Example 7:

3-{(Z)-1-[3-((2,4-dioxo-imidazolidin-5-ylidene)-methyl)-anilino]-1-phenylmethylidene}-5-nitro-2-indolinone×0.25 $H_2O$ (a) 3-amino-benzylidene-hydantoin (A)

2.3 g (10 mmol) of crude 3-nitro-benzylidene-hydantoin, melting point 280–284° C., (prepared as described in Example 6 in (a)) are hydrogenated in 60 ml of DMF and 40 ml EtOH on 2 g of Raney nickel for 36 hours at 20° C. and 3.5 bar. It is filtered over kieselguhr and the filtrate is evaporated down in vacuo. The evaporation residue is crystallised with ether.

Yield: 1.5 g (74% of theory); Melting point: 225–230° C.

(b) 3-{(Z)-1-[3-((2,4-dioxo-imidazolidin-5-ylidene)methyl) anilino]-1-phenylmethylidene}-5-nitro-2-indolinone×0.25 $H_2O$ Prepared from 3-(1-ethoxy-1-phenylmethylidene}-5-nitro-2-indolinone and 1 equivalent of the 3-amino-benzylidene-hydantoin obtained in (a)in DMF (1 hour, 120° C.). After cooling in the ice bath water is added, the precipitate is filtered off and washed with water, MeOH and ether.

Yield: 80% of theory; Melting point: 361° C.; $C_{25}H_{17}N_5O_5$×0.25 $H_2O$; Calc.: C, 63.62; H, 3.74; N, 14.84; Found: 63.62; 3.78; 14.86; Calc.: molar peak $M^+$=467; Found: molar peak $M^+$=467.

EXAMPLE 8

3-{(Z)-1-[4-(1-methyl-1H-imidazol-4-yl)anilino]-1-phenylmethylidene}-2-indolinone×$H_2O$ (a) 4-(4-nitro-phenyl)-imidazole Prepared by nitrogenating 4-phenyl-imidazole in concentrated sulphuric acid with ammonium nitrate analogously to Example D (64% of theory; melting point: 220° C.) or by heating ω-bromo-acetophenone in formamide (160° C., 2.5 hours) (53% of theory; melting point: 220–222° C.).

(b) 1-methyl-4-(4-nitro-phenyl)-imidazole

Prepared by reacting 4-(4-nitro-phenyl)-imidazole in DMSO with potassium-tert.butoxide at 0° C. and then with methyliodide at 20–25° C.

Yield: 76% of theory; Melting point: 176–178° C.

(c) 4-(4-amino-phenyl)-1-methyl-imidazole

Prepared by hydrogenation of 1-methyl-4-(4-nitro-phenyl)-imidazole in MeOH on palladium/charcoal (10%) at 20° C. and 3.5 bar.

Yield: 93% of theory; Melting point: 167–170° C.

(d) 3-{(Z)-1-[4-(1-methyl-1H-imidazole-4-yl)anilino]-1-phenylmethylidene}-2-indolinone×H$_2$O Prepared by reacting 1-acetyl-3-{1-ethoxy-1-phenylmethylidene}-2-indolinone with 1.5 equivalents of 4-(4-amino-phenyl)-1-methyl-imidazole in DMF (120° C., for 2 hours), subsequent treatment with 3 equivalents of 1N sodium hydroxide solution in MeOH (20° C., 1 hour) and precipitation with water.

Yield: 81% of theory; Melting point: 275–278° C.; $C_{25}H_{20}N_4O \times H_2O$; Calc.: C, 73.15; H, 5.40; N, 13.65; Found: 73.55; 5.42; 13.75; Calc.: molar peak $M^+$=392; Found: molar peak $M^+$=392.

The following compounds were obtained analogously to Example 8:

8.1 3-{(Z)-1-[4-(1-methyl-1H-imidazole-4-yl) anilino]-1-phenylmethylidene}-5-nitro-2-indolinone×0.5 H$_2$O Prepared by reacting 1-acetyl-3-{1-ethoxy-1-phenylmethylidene}-5-nitro-2-indolinone with 1.5 equivalents of 4-(4-amino-phenyl)-1-methyl-imidazole in DMF followed by treatment with sodium hydroxide solution in MeOH.

Yield: 92% of theory; Melting point: 302–305° C.; $C_{25}H_{19}N_5O_3 \times 0.5 H_2O$; Calc.: C, 67.26; H, 4.52; N, 15.69; Found: 67.41; 4.47; 15.78; Calc.: molar peak $M^+$=437; Found: molar peak $M^+$=437.

8.2 3-{(Z)-1-[4-(imidazo[1,2-a]pyrimidin-2-yl) anilino]-1-phenylmethylidene}-5-nitro-2-indolinone×H$_2$O Prepared by reacting 1-acetyl-3-{1-ethoxy-1-phenylmethylidene}-5-nitro-2-indolinone with 1.3 equivalents of 4-(imidazo[1,2-a]pyrimidin-2-yl)-aniline×HBr (melting point: 240–250° C.) and 1.7 equivalents of triethylamine in DMF followed by treatment with sodium hydroxide solution in MeOH.

Yield: 91% of theory; Melting point: 350–354° C.; $C_{27}H_{18}N_6O_3 \times H_2O$; Calc.: C 65.85; H, 4.09; N, 17.06; Found: 66.08; 3.81; 17.06; Calc.: molar peak $M^+$=474; Found: molar peak $M^+$=474.

8.3 3-{(Z)-1-[4-(imidazo[1,2-a]pyrimidin-2-yl) anilino]-1-phenylmethylidene}-2-indolinone×0.5 H$_2$O Prepared by reacting 1-acetyl-3-{1-ethoxy-1-phenylmethylidene}-2-indolinone with 1.3 equivalents of 4-(imidazo[1,2-a]pyrimidin-2-yl)-aniline×HBr (melting point: 245–250° C.) and 1.7 equivalents of triethylamine in DMF followed by treatment with sodium hydroxide solution in MeOH.

Yield: 58% of theory; Melting point: 300–302° C.; $C_{27}H_{19}N_5O \times 0.5 H_2O$; Calc.: C, 73.96; H, 4.60; N, 15.97; Found: 74.27; 4.64; 15.72; Calc.: molar peak $M^+$=429; Found: molar peak $M^+$=429.

EXAMPLE 9

3-{(Z)-1-[4-(5-methyl-1H-imidazole-4-yl)anilino]-1-phenylmethylidene}-2-indolinone×0.25 H$_2$O (a) 5-methyl-4-(4-nitro-phenyl)-imidazole Prepared by nitrogenation of 5-methyl-4-phenyl-imidazole (melting point: 185–188° C.) in concentrated sulphuric acid with ammonium nitrate analogously to Example D.

Yield: 78% of theory; Melting point: 206–210° C.

(b) 4-(4-amino-phenyl)-5-methyl-imidazole

Prepared by hydrogenation of 5-methyl-4-(4-nitro-phenyl)-imidazole in MeOH on palladium/charcoal (10%) at 20° C. and 3.5 bar.

Yield (crude): 100% of theory; Melting point: 195–198° C.

(c) 3-{(Z)-1-[4-(5-methyl-1H-imidazole-4-yl)anilino]-1-phenylmethylidene}-2-indolinone×0.25 H$_2$O Prepared by reacting 1-acetyl-3-{1-ethoxy-1-phenylmethylidene}-2-indolinone with 1.5 equivalents of 4-(4-amino-phenyl)-5-methyl-imidazole in DMF (100° C., for 2 hours), subsequent treatment with 6.7 equivalents of piperidine (20° C., 0.5 hours) and precipitation with water.

Yield: 77% of theory; Melting point: 300–305° C.; $C_{25}H_{20}N_4O \times 0.25 H_2O$; Calc.: C, 75.64; H, 5.20; N, 14.11; Found: 75.81; 5.27; 14.04; Calc.: molar peak $M^+$=392; Found: molar peak $M^+$=392.

The following compounds were obtained analogously to Example 9:

9.1 3-{(Z)-1-[4-(5-methyl-1H-imidazole-4-yl) anilino]-1-phenylmethylidene}-5-nitro-2-indolinone×0.5 H$_2$O Prepared by reacting 1-acetyl-3-{1-ethoxy-1-phenylmethylidene}-5-nitro-2-indolinone with 1.5 equivalents of 4-(4-amino-phenyl)-5-methyl-imidazole in DMF followed by treatment with 6.7 equivalents of piperidine.

Yield: 88% of theory; Melting point: 340–345° C.; $C_{25}H_{19}N_5O_3 \times 0.5 H_2O$; Calc.: C, 67.25; H, 4.52; N, 15.69; Found: 67.29; 4.46; 15.81; Calc.: molar peak $M^+$=437; Found: molar peak $M^+$=437.

9.2 3-{(Z)-1-[4-(2-methyl-1H-imidazole-4-yl) anilino]-1-phenylmethylidene}-5-nitro-2-indolinone×H$_2$O;

(a) 2-methyl-4-(4-nitro-phenyl)-imidazole

Prepared by nitrogenation of 2-methyl-4-phenyl-imidazole (melting point: 154–156° C.)) in concentrated sulphuric acid with ammonium nitrate analogously to Example D.

Yield: 34% of theory; Melting point: 216–219° C.

(b) 4-(4-amino-phenyl)-2-methyl-imidazole

Prepared by hydrogenation of 2-methyl-4-(4-nitro-phenyl)-imidazole in MeOH on palladium/charcoal (10%) at 20° C. and 3.5 bar.

Yield (crude, foam): 100% of theory;

(c) 3-{(Z)-1-[4-(2-methyl-1H-imidazole-4-yl)anilino]-1-phenylmethylidene}-5-nitro-2-indolinone×H$_2$O Prepared by reacting 1-acetyl-3-{1-ethoxy-1-phenylmethylidene}-5-nitro-2-indolinone with 1.5 equivalents of 4-(4-amino-phenyl)-2-methyl-imidazole in DMF (100° C., 0.5 hours), subsequent treatment with 6.7 equivalents of piperidine (20° C., 0.5 hours) and precipitation with water.

Yield: 75% of theory; Melting point: 338–340° C.; $C_{25}H_{19}N_5O_3 \times H_2O$; Calc.: C, 65.93; H, 4.65; N, 15.38; Found: 66.19; 4.68; 15.26; Calc.: molar peak $M^+$=437; Found: molar peak $M^+$=437.

9.3 3-{(Z)-1-[4-(1-methyl-1H-imidazole-5-yl)anilino]-1-phenylmethylidene}-5-nitro-2-indolinone×0.4 H$_2$O (a) 1-methyl-5-(4-nitro-phenyl-imidazole Prepared by heating 3.8 g (20 mmol) of 4-(4-nitrophenyl)-imidazole (melting point: 220–222° C.), 2.5 ml (25 mmol) of acetic anhydride and 1.9 ml (30 mmol) of methyliodide in 50 ml acetonitrile in a glass bulb (80° C., 24 hours). The mixture is evaporated down in vacuo, EtOac and 1N hydrochloric acid are added to the evaporation residue, then made alkaline with dilute aqueous ammonia and the phases are separated. The organic phase is washed with water, dried and evaporated down in vacuo. The evaporation residue (3.4 g) is purified by column chromatography on silica gel eluting with CH$_2$Cl$_2$/MeOH (10:1), 1-methyl-4-phenyl-imidazole ($R_f$=0.75) being eluted first, then the desired 1-methyl-5-phenyl-imidazole ($R_f$=0.57) followed by a large amount of 4-(4-nitro-phenyl)-imidazole ($R_f$=0.42).

Yield: 0.40 g (9.8% of theory); Melting point: 167–170° C.

(b) 5-(4-amino-phenyl)-1-methyl-imidazole

Prepared by hydrogenation of 1-methyl-5-(4-nitrophenyl)-imidazole in MeOH on palladium/charcoal (10%) at 20° C. and 3.5 bar.

Yield (crude): 90% of theory; Melting point: 130° C.

(c) 3-{(Z)-1-[4-(1-methyl-1H-imidazole-5-yl)anilino]-1-phenylmethylidene}-5-nitro-2-indolinone×0.4 H$_2$O Prepared by reacting 1-acetyl-3-{1-ethoxy-1-phenylmethylidene}-5-nitro-2-indolinone with 1.3 equivalents of 4-(4-amino-phenyl)-2-methyl-imidazole in DMF (120° C. 1 hour), subsequent treatment with 4.2 equivalents of piperidine (20° C., 1 hour) and precipitation with water.

Yield: 95% of theory; Melting point: 365–368° C.; C$_{25}$H$_{19}$N$_5$O$_3$×0.4 H$_2$O; Calc.: C, 67.53; H, 4.49; N, 15.75; Found: 67.65; 4.65; 16.00; Calc.: molar peak M$^+$=437; Found: molar peak M$^+$=437.

9.4 3-{(Z)-1-[4-(2-acetylamino-1H-imidazole-4-yl)anilino]-1-phenylmethylidene}-5-nitro-2-indolinone×1.5 H$_2$O (a) 2-acetylamino-4-(4-nitro-phenyl)-imidazole Prepared by reacting ω-bromo-4-nitro-acetophenone with 3 equivalents of 1-acetyl-guanidine in DMF (ambient temperature, 5 days) and final purification by column chromatography on silica gel eluting with CH$_2$Cl$_2$/MeOH (20:1).

Yield: 35% of theory (foam).

(b) 2-acetylamino-4-(4-amino-phenyl)-imidazole

Prepared by catalytic hydrogenation of the nitro compound obtained in (a) in MeOH/CH$_2$Cl$_2$ (1:1) on palladium/charcoal (10%) at ambient temperature and 3.5 bar for 2 hours.

Yield (crude): 100% of theory (foam).

(c) 3-{(Z)-1-[4-(2-acetylamino-1H-imidazole-4-yl)anilino]-1-phenylmethylidene}-5-nitro-2--indolinone×1.5 H$_2$O Prepared by reacting 1-acetyl-3-{1-ethoxy-1-phenylmethylidene}-5-nitro-2-indolinone with 2 equivalents of crude 2-acetylamino-4-(4-amino-phenyl)-imidazole in DMF (120° C., for 2 hours), subsequent treatment with 3.8 equivalents of piperidine (20° C., 1 hour) and precipitation with water.

Yield: 56% of theory; Melting point: 275° C.; C$_{26}$H$_{20}$N$_6$O$_6$×1.5 H$_2$O; Calc.: C, 61.53; H, 4.57; N, 16.56; Found: 61.41; 4.70; 17.10; Calc.: molar peak M$^+$=480; Found: molar peak M$^+$=480.

9.5 3-{(Z)-1-[4-(2-acetylamino-5-methyl-1H-imidazole-4-yl)anilino]-1-phenylmethylidene}-5-nitro-2-indolinone×H$_2$O×0.1 DMF (a) 2-acetylamino-5-methyl-4-phenyl-imidazole Prepared by reacting 2-bromo-propiophenone with 3 equivalents of 1-acetyl-guanidine in DMF (ambient temperature, 3 days).

Yield: 49% of theory; Melting point: 188–191° C.

(b) 2-acetylamino-5-methyl-4-(4-nitro-phenyl)-imidazole

Prepared analogously to Example D by reacting 2-acetylamino-5-methyl-4-phenyl-imidazole with ammonium nitrate in concentrated sulphuric acid.

Yield: 87% of theory; Melting point: 265–270° C.

(c) 2-acetylamino-5-methyl-4-(4-amino-phenyl)-imidazole

Prepared by catalytic hydrogenation of the nitro compound obtained in (b) in MeOH/CH$_2$Cl$_2$ (1:1) on palladium/charcoal (10%) at ambient temperature and 3.5 bar for 2 hours.

Yield: 92% of theory; Melting point: 230–235° C.

(d) 3-{(Z)-1-[4-(2-acetylamino-5-methyl-1H-imidazole-4-yl)anilino]-1-phenylmethylidene}-5-nitro-2-indolinone×H$_2$O×0.1 DMF Prepared by reacting 1-acetyl-3-{1-ethoxy-1-phenylmethylidene}-5-nitro-2-indolinone with 1.5 equivalents of 2-acetylamino-5-methyl-4-(4-amino-phenyl)-imidazole in DMF (100° C., 1 hour), subsequent treatment with 5 equivalents of piperidine (20° C., 0.5 hours) and precipitation with water.

Yield: 69% of theory; Melting point: 300–305° C.; C$_{27}$H$_{22}$N$_6$O$_4$×H$_2$O×0.1 DMF; Calc.: C, 63.01; H, 4.72; N, 16.44; Found: 63.21; 4.66; 16.97; Calc.: molar peak M$^+$=494; Found: molar peak M$^+$=494.

9.6 3-{(Z)-1-[3-(1H-imidazol-4-yl)anilino]-1-phenylmethylidene}-5-nitro-2-indolinone (a) 4-(3-nitro-phenyl)-imidazole Prepared by heating α-bromo-3-nitro-acetophenone in formamide (160° C., 2.5 hours).

Yield: 86% of theory; Melting point: 210–212° C. (Lit. melting point: 224° C.).

(b) 4-(3-amino-phenvyl-imidazole×2 HCl

Prepared by catalytic hydrogenation of the nitro compound obtained in (a) in MeOH on palladium/charcoal (10%) at ambient temperature and 3.5 bar for 2 hours and subsequent addition of ethanolic hydrochloric acid.

Yield: 85% of theory; Melting point: 296° C.

(c) 3-{(Z)-1-[3-(1H-imidazol-4-yl)anilino]-1-phenylmethylidene}-5-nitro-2-indolinone Prepared by reacting 1-acetyl-3-{1-ethoxy-1-phenylmethylidene}-5-nitro-2-indolinone with 1.5 equivalents of 4-(3-amino-phenyl)-imidazole×2 HCl and 3.25 equivalents of triethylamine in DMF (100° C., for 1.5 hours), subsequent treatment with 5 equivalents of piperidine (20° C., 1 hour) and precipitation with water.

Yield: 95% of theory; Melting point: 365° C.; C$_{24}$H$_{17}$N$_5$O$_3$; Calc.: C, 68.08; H, 4.05; N, 16.54; Found: 67.68; 4.3β; 16.25; Calc.: molar peak M$^+$=423; Found: molar peak M$^+$=423.

9.7 3-{(Z)-1-[4-(1H-tetrazol-5-yl)anilino-1-phenylmethylidene}-5-nitro-2-indolinone (a) 5-(4-amino-phenyl)-1H-tetrazole Prepared by catalytic hydrogenation of 5-(4-nitrophenyl)-1H-tetrazol in MeOH on platinum dioxide (ambient temperature, 3.5 bar, 40 minutes).

Yield: 87% of theory; Melting point: 264–268° C.

(b) 3-{(Z)-1-[4-(1H-tetrazol-5-yl)anilino]-1-phenylmethylidene}-5-nitro-2-indolinone Prepared by reacting 1-acetyl-3-{1-ethoxy-1-phenylmethylidene}-5-nitro-2-indolinone with 1.3 equivalents of 5-(4-amino-phenyl)-1H-tetrazole in DMF (125° C., for 2 hours), subsequent treatment with 6.7 equivalents of piperidine (20° C., 1 hour) and precipitation with water.

Yield: 40% of theory; Melting point: >400° C.; $C_{22}H_{15}N_7O_3$; Calc.: molar peak $M^+=425$; Found: molar peak $M^+=425$.

9.8 3-{(Z)-1-[4-((imidazol-4-yl)methyl)anilino]-1-phenylmethylidene}-5-nitro-2-indolinone (a) 1-triphenylmethyl-4-[(1-hydroxy-1-phenyl)methyl]-1H-imidazole Prepared by reacting 4-formyl-1-triphenylmethyl-1H-imidazole (melting point: 202–205° C.; prepared by oxidation of the corresponding 4-hydroxymethyl compound with manganese dioxide in dioxane) with phenylmagnesium bromide in dry THF.

Yield: 94% of theory; Melting point: 187–191° C.

(b) 4-benzyl-1H-imidazole

Prepared according to Arch. Pharm. 1975, 308, 755–759 by catalytic hydrogenation of the compound obtained in (a) in MeOH on palladium/charcoal (10%) (50° C., 3.5 bar, 7 hours).

Yield: 44% of theory; Melting point: 82–84° C. (Lit. melting point: 85–86° C.).

(c) 4-(4-nitro-benzyl)-1H-imidazole

Prepared according to Arch. Pharm. 1975, 308, 755–759 by reacting 4-benzyl-1H-imidazole in fuming 100% nitric acid at −10 to −5° C. (30 minutes).

Yield: 63% of theory; Melting point: 162–164° C. (Lit. Melting point: 161–162° C.).

(d) 4-(4-amino-benzyl)-1H-imidazole

Prepared by catalytic hydrogenation of 4-(4-nitrobenzyl)-1H-imidazole in EtOH on palladium/charcoal (10%) (20° C., 3.5 bar, 45 minutes).

Yield: 95% of theory; Melting point: 98–100° C.

(e) 3-{(Z)-1-[4-((imidazol-4-yl)methyl)anilino]-1-phenylmethylidene}-5-nitro-2-indolinone Prepared by reacting 1-acetyl-3-{1-ethoxy-1-phenylmethylidene}-5-nitro-2-indolinone with 1.45 equivalents of 4-(4-amino-benzyl)-1H-imidazole in DMF (100° C., for 2 hours), subsequent treatment with 5 equivalents of piperidine (20° C., 1 hour) and precipitation with water.

Yield: 91% of theory; Melting point: 322–325° C.; $C_{25}H_{19}N_5O_3$; Calc.: C, 68.64; H, 4.38; N, 16.01; Found: 68.30; 4.38; 15.83; Calc.: molar peak $M^+=437$; Found: molar peak $M^+=437$.

9.9 3-{(Z)-1-[4-(2-(imidazol-4-yl)ethyl)anilino]-1-phenylmethylidene}-5-nitro-2-indolinone×0.5 $H_2O$ (a) 4-[2-(4-nitro-phenyl)-ethenyl]-1-triphenylmethyl-1-H-imidazole Prepared by reacting 4-nitro-benzaldehyde with 1.2 equivalents of (1-triphenylmethyl-1H-imidazol-4-yl)methyl-triphenylphosphonium-chloride (melting point: 240–245° C.) and 2 equivalents of DBU in THF/EtOH (1:1) (20° C., for 2 hours) and precipitation with water. Yield of an (E)-isomer (with a trace of the rather more polar (Z) isomer): 50% of theory; Melting point: 280–285° C. A mixture of the (E/Z) isomers (~3:4) was obtained from the mother liquor of the (E)-isomer by column chromatography on silica gel with $CH_2Cl_2$ as eluant:

Yield: 43% of theory (foam).

(b) 4-[2-(4-nitro-phenyl)-(E/Z)-ethenyl]-1-H-imidazole

Prepared by refluxing the mixture of the (E/Z) isomers (~¾) obtained in (a) in 1N hydrochloric acid (4 hours) and column chromatography on silica gel with $CH_2Cl_2$/MeOH (10:1) as eluant.

Yield of (E/Z) isomers (~3:4) mixture: 96% of theory (foam).

(c) 4-[2-(4-amino-phenyl)-ethyl]-1-H-imidazole

Prepared by catalytic hydrogenation of the mixture of the (E/Z) isomers (~3/4) obtained in (b) in EtOH on palladium/charcoal (10%) (20° C., 3.5 bar, 1 hour).

Yield: 98% of theory; Melting point: 165–167° C.

(d) 3-{(Z)-1-[4-(2-(imidazol-4-yl)ethyl)anilino]-1-phenylmethylidene}-5-nitro-2-indolinone×0.5 $H_2O$ Prepared by reacting 1-acetyl-3-{1-ethoxy-1-phenylmethylidene}-5-nitro-2-indolinone with 1.3 equivalents of 4-[2-(4-amino-phenyl)-ethyl]-1-H-imidazole in DMF (120° C., 0.5 hours) subsequent treatment with 4.2 equivalents of piperidine (20° C., 1 hour) and precipitation with water.

Yield: 72% of theory; Melting point: 305–307° C.; $C_{26}H_{21}N_5O_3 \times 0.5\ H_2O$; Calc.: C, 67.82; H, 4.82; N, 15.21; Found: 68.07; 4.75; 14.74; Calc.: molar peak $M^+=451$; Found: molar peak $M^+=451$.

9.10 3-{(Z)-1-[4-(2-(imidazol-4-yl)-(E)-ethenyl)anilino]-1-phenylmethylidene}-5-nitro-2-indolinone×0.5 $H_2O$ (a) 4-[2-(4-nitro-phenyl)-(E)-ethenyl]-1-H-imidazole Prepared by refluxing the 4-[2-(4-nitro-phenyl)-(E)-ethenyl]-1-triphenylmethyl-1-H-imidazole (melting point: 280–285° C.) obtained in Example 9.9 (a) in 1N hydrochloric acid (4 hours) and column chromatography on silica gel with $CH_2Cl_2$/MeOH (10:1) as eluant.

Yield: 97% of theory; Melting point: 185–188° C.

(b) 4-[2-(4-amino-phenyl)-(E)-ethenyl]-1-H-imidazole

Prepared by treating the nitro compound obtained in (a) in 80% acetic acid with iron powder at 70° C.

Yield: 71% of theory; Melting point: 228–230° C.

(c) 3-{(Z)-1-[4-(2-(imidazol-4-yl)-(E)-ethenyl)anilino]-1-phenylmethylidene}-5-nitro-2-indolinone×0.5 $H_2O$ Prepared by reacting 1-acetyl-3-{1-ethoxy-1-phenylmethylidene}-5-nitro-2-indolinone with 1.5 equivalents of 4-[2-(4-amino-phenyl)-(E)-ethenyl]-1-H-imidazole in DMF (110° C., for 1.5 hours), subsequent treatment with 3 equivalents of piperidine (20° C., 0.5 hours) and precipitation with water.

Yield: 89% of theory; Melting point: 338–342° C.; $C_{26}H_{19}N_5O_3 \times 0.5\ H_2O$; Calc.: C, 68.11; H, 4.40; N, 15.28; Found: 68.15; 4.27; 15.21; Calc.: molar peak $M^+=449$; Found: molar peak $M^+=449$.

9.11 3-{(Z)-1-4-((2,4-dioxo-thiazolidin-5-ylidene)methyl)anilino]-1-phenylmethylidene}-5-nitro-2-indolinone×0.5 $H_2O$ (a) 5-(4-amino-benzylidene)-thiazolidin-2,4-dione Prepared by catalytic hydrogenation of 5-(4-nitro-benzylidene)-thiazolidin-2,4-dione [melting point: 265–270° C.; obtained by heating 4-nitro-benzaldehyde and 2 equivalents of thiazolidin-2,4-dione in the presence of piperidine in toluene using a water separator] in glacial acetic acid on palladium/charcoal (10%) (50° C., 3.5 bar, 0.5 hours).

Yield: 62% of theory; Melting point: 256–260° C.

(b) 3-{(Z)-1-[4-((2,4-dioxo-thiazolidin-5-ylidene)methyl)anilino]-1-phenylmethylidene}-5-nitro-2-indolinone×0.5 $H_2O$ Prepared by reacting 1-acetyl-3-{1-ethoxy-1-phenylmethylidene}-5-nitro-2-indolinone with 1.5 equivalents of 5-(4-amino-benzylidene)-thiazolidin-2,4-dione in DMF (120° C., for 2 hours), subsequent treatment with 6 equivalents of piperidine (20° C., 0.5 hours), evaporation in vacuo and trituration with EtOH.

Yield: 27% of theory; Melting point: 328–333° C.; $C_{25}H_{16}N_4O_5S \times 0.5\ H_2O$; Calc.: C, 60.84; H, 3.47; N, 11.35; Found: 60.46; 2.83; 11.23; Calc.: molar peak $M^+=484$; Found: molar peak $M^+=484$.

9.12 3-{(Z)-1-[4-((2,4-dioxo-thiazolidin-5-yl)methyl)anilino]-1-phenylmethylidene}-5-nitro-2-indolinone (a) 5-(4-amino-benzyl)-thiazolidin-2,4-dione Prepared by catalytic hydrogenation of 5-(4-amino-benzylidene)-thiazolidin-2,4-dione in glacial acetic acid on palladium/charcoal (10%) (50° C., 3.5 bar, 6 hours).

Yield: 42% of theory; Melting point: 135–140° C.

(b) 3-{(Z)-1-[4-((2,4-dioxo-thiazolidin-5-yl)methyl)anilino]-1-phenylmethylidene}-5-nitro-2-indolinone Prepared by reacting 1-acetyl-3-{1-ethoxy-1-phenylmethylidene}-5-nitro-2-indolinone with 1.2 equivalents of 5-(4-amino-benzyl)-thiazolidin-2,4-dione in DMF (120° C., 1 hour), subsequent treatment with 6.7 equivalents of piperidine (20° C., 1 hour), evaporation in vacuo and trituration with EtOH/water (1:1).

Yield: 96% of theory; Melting point: 265–270° C.; $C_{25}H_{18}N_4O_5S$; Calc.: C, 61.72; H 3.73; N, 11.52; Found: 61.83; 3.90; 11.28; Calc.: molar peak $M^+=486$; Found: molar peak $M^+=486$.

9.13 3-{(Z)-1-[4-(2-ethyl-1H-imidazol-4-yl)anilino]-1-phenyl-methylidene}-5-nitro-2-indolinone×0.6 $H_2O$ Prepared by reacting 3-{1-ethoxy-1-phenyl-methylidene}-5-nitro-2-indolinone with 1.3 equivalents of 4-(4-amino-phenyl)-2-ethyl-imidazole in DMF (120° C., 1,5 hours) and precipitation with water.

Yield: 81% of theory; Melting point: 254–256° C.; $C_{26}H_{21}N_5O_3 \times 0.6 \times H_2O$; Calc.: C, 67.55; H, 4.84; N, 15.15; Found: 67.49; 5.07; 15.23; Calc.: molar peak $M^+=451$; Found: molar peak $M^+=451$.

9.14 3-{(Z)-1-[4-(2-n-Propyl-1H-imidazol-4-yl)anilino]-1-phenyl-methylidene}-5-nitro-2-indolinone×$H_2O$ Prepared by reacting 3-{1-ethoxy-1-phenyl-methylidene}-5-nitro-2-indolinone with 1.3 equivalents of 4-(4-amino-phenyl)-2-n-propyl-imidazole in DMF (120° C., 1 hour) and precipitation with water.

Yield: 67% of theory; Melting point: 180° C.; $C_{27}H_{23}N_5O_3 \times H_2O$; Calc.: C, 67.07; H, 5.21; N, 14.48; Found: 67.08; 5.33; 14.48; Calc.: molar peak $M^+=465$; Found: molar peak $M^+=465$.

9.15 3-{(Z)-1-[4-(2-isopropyl-1H-imidazol-4-yl)anilino]-1-phenyl-methylidene}-5-nitro-2-indolinone×$H_2O$ Prepared by reacting 3-{1-ethoxy-1-phenyl-methylidene}-5-nitro-2-indolinone with 1.3 equivalents of 4-(4-amino-phenyl)-2-isopropyl-imidazole in DMF (120° C., 1 hour) and precipitation with water.

Yield: 75% of theory; Melting point: 202–202° C. $C_{27}H_{23}N_5O_2 \times H_2O$; Calc.: C, 67.07; H, 5.21; N, 14.48; Found: 67.20; 5.29; 14.45; Calc.: molar peak $M^+=465$; Found: molar peak $M^+=465$.

EXAMPLE 10

3-{(Z)-1-[4-(1H-imidazol-4-yl)anilino]-1-(4-trifluoromethyl-phenyl)methylidene}-5-nitro-2-indolinone (a) 1-acetyl-3-[1-hydroxy-1-(4-trifluoromethyl-phenyl)-methylidene}-5-nitro-2-indolinone Prepared by reacting 1-acetyl-5-nitro-2-indolinone with one equivalent of 4-trifluoromethyl-benzoic acid in dry DMF in the presence of 1 equivalent each of TBTU and HOBT and 5 equivalents of Hüinig's base (20° C., 4 hours), stirring into dilute hydrochloric acid, filtering the precipitate, dissolving the precipitate in EtOac, drying the organic phase and evaporation in vacuo and purifying the evaporation residue by column chromatography on silica gel with $CH_2Cl_2$/MeOH (10:1) as eluant.

Yield: 86% of theory; Melting point: 177° C.; Enol reaction (with $FeCl_3$ solution in EtOH): positive.

(b) 3-[1-bromo-1-(4-trifluoromethyl-phenyl)methylidene}-5-nitro-2-indolinone

Prepared by reacting the compound obtained in (a) with 1.2 equivalents of triphenylphosphine and 1.1 equivalents of tetrabromo-methane in $CH_2Cl_2$ (for 1 hour at 0° C., overnight at ambient temperature), the addition of 2 equivalents of piperidine and stirring at ambient temperature for 1.5 hours, and evaporation in vacuo and purification of the evaporation residue by column chromatography on silica gel with cyclohexane/EtOac (1:1) as eluant.

Yield: 5.6% of theory; Melting point: 222–225° C.; $C_{16}H_8BrF_3N_2O_3$; Calc.: molar peak $M^+=412/414$ (1 Br); Found: molar peak $M^+=412/414$ (1 Br).

(c) 3-{(Z)-1-[4-(1H-imidazol-4-yl)anilino]-1-(4-trifluoromethyl-phenyl)methylidene}-5-nitro-2-indolinone Prepared by reacting the bromine compound obtained in (b) with 2 equivalents of 4-(1H-imidazol-4-yl)aniline×2 HCl (melting point: 350° C.) and 3.9 equivalents of triethylamine in toluene/DMF (2:1) for 2 hours at 40° C., pouring into dilute ammonia and purification of the precipitate obtained by column chromatography on silica gel with $CH_2Cl_2$/MeOH/conc. ammonia (10:1:0.1) as eluant.

Yield: 17.4% of theory; Melting point: 358° C.; $C_{25}H_{16}F_3N_5O_3$; Calc.: molar peak $M^+=491$; Found: molar peak $M^+=491$.

The following compound was obtained analogously to Example 10:

10.1 3-{(Z)-1-[4-(1H-imidazol-4-yl)anilino]-1-(3-cyano-phenyl)methylidene}-2-indolinone (a) 1-acetyl-3-[1-hydroxy-1-(3-cyano-phenyl)methylidene]-2-indolinone Prepared from 1-acetyl-2-indolinone and 3-cyano-benzoic acid in dry DMF in the presence of TBTU, HOBT and Hüinig's base (35° C., for 2 hours) and final purification by column chromatography on silica gel with $CH_2Cl_2$/MeOH (10:1) as eluant.

Yield: 62% of theory; Melting point: 173–175° C.; Enol reaction (with $FeCl_3$ solution in EtOH): positive.

(b) 3-[1-bromo-1-(3-cyano-phenyl)methylidene]-2-indolinone

Prepared by reacting the compound obtained in (a) with triphenylphosphine and tetrabromomethane in $CH_2Cl_2$ and final purification by column chromatography on silica gel with cyclohexane/EtOac (1:1) as eluant.

Yield: 14% of theory; Melting point: 218° C.; $C_{16}H_9BrN_2O$; Calc.: molar peak $M^+=324/326$ (1 Br); Found: molar peak $M^+=324/326$ (1 Br).

(c) 3-{(Z)-1-[4-(1H-imidazol-4-yl)anilino]-1-(3-cyano-phenyl)-methylidene}-2-indolinone Prepared by reacting the bromine compound obtained in (b) with 4 equivalents of 4-(1H-imidazol-4-yl)anilinex2 HCl (melting point: 350° C.) and 6 equivalents of triethylamine in toluene/DMF (3:2) (60° C., 4 hours), pouring into dilute ammonia, separation of the organic phase and purification thereof by column chromatography on silica gel with $CH_2Cl_2$/MeOH/conc. ammonia (10:1:0.15) as eluant.

Yield: 3.3% of theory; Melting point: 76° C.; DC-$R_f$=0.43 [silica gel; $CH_2Cl_2$/MeOH/conc. ammonia (100:10:1)]; $C_{25}H_{17}N_5O$; Calc.: molar peak $M^+$=403; Found: molar peak $M^+$=403.

EXAMPLE 11

3-{(Z)-1-[4-(1H-imidazol-4-yl)anilino]-1-(4-methyl-phenyl)methylidene}-5-nitro-2-indolinone (a) 1-acetyl-3-[1-hydroxy-1-(4-methyl-phenyl)methylidene]-5-nitro-2-indolinone Prepared analogously to Example 10(a) from 1-acetyl-5-nitro-2-indolinone and 4-methyl-benzoic acid in dry DMF in the presence of TBTU, HOBT and Hünig's base (20° C., overnight) and final purification by column chromatography on silica gel with $CH_2Cl_2$ as eluant.

Yield: 53% of theory; Melting point: 175° C.; Enol reaction (with $FeCl_3$ solution in EtOH): positive.

(b) 1-acetyl-3-[1-chlor-1-(4-methyl-phenyl)methylidene]-5-nitro-2-indolinone 3.55 g (10.5 mmol) of 1-acetyl-3-[1-hydroxy-1-(4-methyl-phenyl)methylidene}-5-nitro-2-indolinone and 2.40 g (11.5 mmol) of $PCl_5$ are heated in 60 ml toluene for 2 hours at 80° C. The mixture is evaporated down in vacuo, fresh toluene is added to the evaporation residue, it is evaporated down again and this procedure is repeated once more. The evaporation residue is dissolved in a little toluene with heating. During slow cooling an isomer, probably the (Z) isomer, crystallised out. A mixture of the (Z) and (E) isomers was also obtained from the mother liquor by column chromatography on silica gel with $CH_2Cl_2$.

(Z)-isomer: Yield: 46% of theory; Melting point: 201–202° C.; DC-$R_f$=0.54 [silica gel; $CH_2Cl_2$/toluene (5:2)]; $C_{18}H_{13}ClN_2O_4$; Calc.: molar peak $M^+$=356/358 (1 Cl); Found: molar peak $M^+$=356/358 (1 Cl).

mixture of (Z/E) isomers: Yield: 37% of theory; Melting point: 168–170° C.; DC-$R_f$=0.54 and 0.49 [silica gel; $CH_2Cl_2$/toluene (5:2)]; Both DC spots indicate the molar peak $M^+$=356/358 (1 Cl).

(c) 3-{(Z)-1-[4-(1H-imidazol-4-yl)anilino]-1-(4-methyl-phenyl)methylidene]-5-nitro-2-indolinone Prepared by reacting the (Z) isomer obtained in (b) (melting point: 201–202° C.) with 1.1 equivalent of 4-(1H-imidazol-4-yl)anilinex2 HCl (melting point: 350° C.) and 3.3 equivalents of $NaHCO_3$ in DMF (50° C., 1 hour), pouring into dilute ammonia, extraction with EtOAc, separation of the organic phase and purification thereof by column chromatography on silica gel with $CH_2Cl_2$/MeOH/conc. ammonia (10:1:0.1) as eluant.

Yield: 4.6% of theory; Melting point: 297° C.; $C_{25}H_{19}N_5O_3$; Calc.: molar peak $(M+H)^+$=438; Found: molar peak $(M+H)^+$=438.

The following compounds were obtained analogously to Example 11:

11.1 3-{(Z)-1-[4-(1H-imidazol-4-yl)anilino]-1-(4-bromo-phenyl)methylidene}-2-indolinone (a) 1-acetyl-3-[1-hydroxy-1-(4-brom-phenyl)methylidene]-2-indolinone Prepared analogously to Example 10(a) from 1-acetyl-2-indolinone and 4-bromo-benzoic acid in dry DMF in the presence of TBTU, HOBT and Hünig's base (20° C., overnight) and final purification by column chromatography on silica gel with $CH_2Cl_2$/MeOH (20:1) as eluant.

Yield: 81% of theory; Melting point: 140–142° C.; Enol reaction (with $FeCl_3$ solution in EtOH): positive.

(b) 1-acetyl-3-[1-chloro-1-(4-bromo-phenyl)methylidene]-2-indolinone 1-acetyl-3-[1-hydroxy-1-(4-bromo-phenyl)methylidene}-2-indolinone and 2 equivalents of $PCl_5$ are heated in toluene for 1 hour at 100° C. The mixture is filtered, evaporated down in vacuo and petroleum ether is added to the oily evaporation residue.

Yield: 46% of theory; Melting point: 177–178° C.; $C_{17}H_{11}BrClN_{O2}$; Calc.: molar peak $M^+$=375/377/379 (1 Br, 1 Cl); Found: molar peak $M^+$=375/377/379 (1 Br, 1 Cl).

(c) 3-[Chloro-1-(4-bromo-phenyl)methylidene]-2-indolinone

Prepared from the compound obtained in (b) by reacting with 1 equivalent of piperidine in MeOH (5 hours, 40° C.)

Yield: 46% of theory; Melting point: 260–262° C.; $C_{15}H_9BrClNO$ Calc.: molar peak $M^+$=333/335/337 (Br, Cl); Found: molar peak $M^+$=333/3335/337 (Br, Cl).

(d) 3-{(Z)-1-[4-(1H-imidazol-4-yl)anilino]-1-(4-bromo-phenyl)methylidene}-2-indolinone Prepared by reacting the compound obtained in (c) with 1.2 equivalents of 4-(1H-imidazol-4-yl)anilinex2 HCl (melting point: 350° C.) and 6 equivalents of Hünig's base in DMF (80° C., 6 hours; 100° C., for 2 hours), pouring into water, extraction with EtOac, separation of the organic phase and purification thereof by column chromatography on silica gel with $CH_2Cl_2$/MeOH (10:1) as eluant.

Yield: 8.2% of theory; Melting point: 332–336° C.; $C_{24}H_{17}BrN_4O$; Calc.: molar peak $M^+$=456/458 (1 Br); Found: molar peak $M^+$=456/458 (1 Br).

11.2 3-{(Z)-1-[4-((2-oxo-pyrrolidin-1-yl)-methyl)anilino]-1-(4-bromo-phenyl)methylidene}-5-nitro-2-indolinone (a) 1-acetyl-3-[1-hydroxy-1-(4-bromo-phenyl)methylidene]-5-nitro-2-indolinone Prepared analogously to Example 10(a) from 1-acetyl-5-nitro-2-indolinone and 4-bromo-benzoic acid in dry DMF in the presence of TBTU, HOBT and Hünig's base (20° C., overnight) and evaporation in vacuo. A sample of the crude product obtained was purified by column chromatography on silica gel with $CH_2Cl_2$/MeOH (20:1) as eluant.

Melting point: 313° C.; Enol reaction (with $FeCl_3$ solution in EtOH): positive. $C_{17}H_{11}BrN_2O$; Calc.: molar peak $M^+$=402/404 (Br); Found: molar peak $M^+$=402/404 (Br).

(b) 1-acetyl-3-[1-chloro-1-(4-bromo-phenyl)methylidene]-5-nitro-2-indolinone

Prepared from the crude product obtained in (a) by heating with 2 equivalents of $PCl_5$ in dry toluene (3 hours, 80° C.), evaporation in vacuo and trituration with ether.

Yield: 59% of theory: Melting point: 202–205° C.; $C_{17}H10BrClN_2O_4$; Calc.: molar peak $M^+$=420/422/424 (Br, Cl); Found: molar peak $M^+$=420/422/424 (Br, Cl).

(c) 3-[1-Chloro-1-(4-bromo-phenyl)methylidene]-5-nitro-2-indolinone

Prepared from the compound obtained in (b) by dropwise addition of enough of a dilute solution of sodium methoxide in MeOH at ambient temperature, to ensure that no more starting compound can be detected by DC testing.

Yield: 88% of theory; Melting point: 263–265° C.; $C_{17}H_8BrClN_2O_3$; Calc.: molar peak $M^+$=378/380/382 (Br, Cl); Found: molar peak $M^+$=378/380/382 (Br, Cl).

(d) 3-{(Z)-1-(4-(2-oxo-pyrrolidin-1-yl)-methyl)anilino-1-(4-bromo-phenyl)methylidene}-5-nitro-2-indolinone Prepared by reacting the compound obtained in (c) with 1 equivalent of 4-((2-oxo-pyrrolidin-1-yl)-methyl)aniline and 2 equivalents of Hünig's base in DMF (120° C., 0.75 hours), pouring into water, extraction with EtOac, separation of the organic phase and purification thereof by column chromatography on silica gel with $CH_2Cl_2$/MeOH (15:1) as eluant.

Yield: 53% of theory; Melting point: 285–287° C.; $C_{26}H_{21}BrN_4O_4$; Calc.: molar peak $MH^+$=532/534 (Br); Found: molar peak $MH^+$=532/534 (Br).

11.3 3-{(Z)-1-[4-(pyrrolidin-1-yl-methyl)anilino]-1-(4-bromo-phenyl)methylidene}-5-nitro-indolinone Prepared by reacting 3-[1-chloro-1-(4-bromo-phenyl)methylidene]-5-nitro-2-indolinone with 1 equivalent of 4-(pyrrolidin-1-yl-methyl)aniline and 2 equivalents of Hünig's base in DMF (1 hours, 120° C.), pouring into water, extraction with EtOac, separation of the organic phase and purification thereof by column chromatography on $SiO_2$ with $CH_2Cl_2$/MeOH (15:1) as eluant.

Yield: 37.6% of theory; Melting point: 300–304° C.; $C_{26}H_{23}BrN_4O_3$; Calc.: molar peak $M^+$=518/520 (Br); Found: molar peak $M^+$=518/420 (Br).

11.4 3-{(Z)-1-[4-(Pyrrolidin-1-ylmethyl)anilino]-1-[4-(imidazol-1-yl-methyl)-phenylmethylidene}-5-nitro-2-indolinone (a) 1-Acetyl-3-{1-hydroxy-1-[4-(imidazol-1-yl-methyl)-phenyl]-methylidene}-5-nitro-2-indolinone Prepared analogously to Example 10(a) from 1-acetyl-5-nitro-indolinone and 4-(imidazol-1-ylmethyl)benzoic acid in dry DMF in the presence of TBTU, HOBT and Hünig's base.

Yield: 89% of theory; Melting point: 235–237° C.; $C_{21}H_{16}N_4O_5$ (404.39); Calc.: molar peak $(M-H)^-$=403; Found: molar peak $(M-H)^-$=403.

(b) 3-{(Z)-1-[4-(Pyrrolidin-1-yl-methyl)anilino]-1-[4-(imidazol-1-yl-methyl)phenyl]-methylidene}-5-nitro-2-indolinone Prepared by reacting the compound obtained in (a) with $PCl_5$ in toluene analogously to Example 11(b) and subsequently with 4-(pyrrolidin-1-yl-methyl)aniline and triethylamine in THF analogously to Example 11.1d.

Yield: 16% of theory; Melting point: 202–204° C.; $C_{30}N_{28}N_6O_3$ (520.60); Calc.: molar peak $(M+H)^+$=521; Found: molar peak $(M+H)^+$=521; DC-$R_f$=0.7 (silica gel; dichloromethane/methanol/$NH_4OH$ 5:1:0.01

11.5 3-{(Z)-1[4-(1H-Imidazol-4-yl)anilino]-1-[4-(imidazol-1-yl-methyl)phenyl]methylidene}-5-nitro-2-indolinone Prepared analogously to Example 11.4(b) by reacting 1-acetyl-3-{1-hydroxy-1-[4-(imidazol-1-yl-methyl)-phenyl]methylidene}-5-nitro-2-indolinone with $PCl_5$ in toluene and subsequently with 4-(1H-imidazol-4-yl)aniline and triethylamine in THF.

Yield: 25% of theory; melting point: 230–235° C.; $C_{28}N_{21}N_7O_3$ (503.53); Calc.: molar peak $(M+H)^+$=504 Found: molar peak $(M+H)^+$=504; $C_{27}N_{24}N_4O_5\times H_2O$ (521.54); Calc.: C, 64.45; N, 4.40; N, 18.57; Found: 64.30; 4.40; 18.57.

EXAMPLE 12

3-{(Z)-1-[3-(1H-imidazolin-2-yl)anilino]-1-phenylmethylidene}-2-indolinone×0.4 $H_2O$ 1-Benzoyl-3-{1-[3-cyano-anilino]-1-phenylmethylidene}-2-indolinone (melting point: 245–248° C.) are added to a cold (−10° C.) saturated solution of HCl gas in MeOH. After stirring overnight at ambient temperature the mixture is evaporated down at 30° C. in vacuo, the evaporation residue is mixed with ether and dried at 20° C. in vacuo. The crude imino-methylether-hydrochloride obtained (melting point: 233–237° C.) is stirred together with 5 equivalents of ethylenediamine overnight at ambient temperature. After evaporation in vacuo ether is added and the precipitate obtained is purified by column chromatography on silica gel with MeOH/EtOac/conc. ammonia (9:1:0.5) as eluant.

Yield: 25% of theory; Melting point: 262–267° C.; $C_{24}H_{20}N_4O\times0.4\ H_2O$; Calc.: C, 74.35; H, 5.41; N, 14.45; Found: 74.64; 5.55; 14.23; Calc.: molar peak $M^+$=380; Found: molar peak $M^+$=380.

The following compound was obtained analogously to Example 12:

12.1 3-{(Z)-1-[4-((imidazolin-2-yl)methyl)-anilino]-1-phenyl-methylidene}-5-nitro-2-indolinone Prepared from 3-{(Z)-1-[4-cyanomethyl-anilino]-1-phenylmethylidene}-5-nitro-2-indolinone (melting point: 329° C.) by treating first with saturated HCl/MeOH solution at −10° C. and then with ethylenediamine, separation of 3-{(Z)-1-[4-methoxycarbonylmethyl-anilino]-1-phenylmethylidene}-5-nitro-2-indolinone (43% of theory, melting point: 238–240° C.) by extraction from 2N acetic acid solution with methylene chloride and precipitation of the title compound by the addition of conc. ammonia to the aqueous solution.

Yield: 14.5% of theory; Melting point: 329–330° C. $C_{25}H_{21}N_5O_3$; Calc.: molar peak $M^+$=439; Found: molar peak $M^+$=439.

EXAMPLE 13

3-{(Z)-1-[4-(1H-imidazol-4-yl)anilino]-1-phenylmethylidene}-5-nitro-2-indolinone hydrochloride×0.5 $H_2O$×0.8 dioxane Prepared from 3-{(Z)-1-[4-(1H-imidazol-4-yl)anilino]-1-phenylmethylidene}-5-nitro-2-indolinone in dioxane with 1.09 equivalents of 1N hydrochloric acid and evaporation in vacuo.

Yield: 81% of theory; Melting point: >400° C.; $C_{24}H_{17}N_5O_2\times HCl\times 0.5\ H_2O\times 0.8$ dioxane; Calc.: C, 60.48; H, 4.75; N, 13.01; Found: 60.62; 4.72; 12.93; Calc.: molar peak $M^+$=423; Found: molar peak $M^+$=423.

EXAMPLE 14

3-{(Z)-1-[4-(1,2,3,4-tetrahydro-isoquinolin-(5)-yl)amino]-1-phenylmethylidene}-2-indolinone-hydrochloride×$H_2O$ Prepared from 3-{(Z)-1-[4-(2-Boc-1,2,3,4-tetrahydro-isoquinolin-(5)-yl)amino]-1-phenylmethylidene}-2-indolinone in $CH_2Cl_2$ with hydrochloric acid/EtOac (20° C., for 2 hours).

Yield: 83% of theory; Melting point: ~290° C.; $C_{24}H_{21}N_3O\times HCl\times H_2O$; Calc.: C, 68.32; H, 5.73; N, 9.96; Found: 68.71; 5.76; 10.13; Calc.: molar peak $M^+$=367; Found: molar peak $M^+$=367.

The following was obtained analogously to Example 14:

14.1 3-{(Z)-1-[(1,2,3,4-tetrahydro-isoquinolin-6-yl)amino]-1-phenylmethylidene}-5-nitro-2-indolinone× HCl×$H_2O$ Prepared from 3-{(Z)-1-[(2-Boc-1,2,3,4-tetrahydro-isoquinolin-6-yl)amino-1-phenylmethylidene}-5-nitro-2-indolinone by hydrogen chloride in EtOac.

Yield: 86% of theory; Melting point: 299–300° C.; $C_{24}H_{20}N_4O_3 \times HCl \times H_2O$; Calc.: C, 61.74; H, 4.96; N, 12.00; Found: 62.11; 4.70; 12.05; Calc.: molar peak $M^+=412$; Found: molar peak $M^+=412$.

14.2 Mixture of 3-{(Z)-1-[4-((imidazolin-2-yl)methyl)anilino]-1-phenylmethylidene}-5-nitro-2-indolinone×CF₃COOH (75%) and 3-{(Z)-1-[3-((imidazolin-2-yl)methyl)anilino]-1-phenylmethylidene}-5-nitro-2-indolinone× CF₃COOH (25%)

Prepared from the mixture of 3-{(Z)-1-[4-((1-Boc-imidazolin-2-yl)methyl)anilino]-1-phenylmethylidene}-5-nitro-2-indolinone (75%) and 3-{(Z)-1-[3-((1-Boc-imidazolin-2-yl)methyl)anilino]-1-phenylmethylidene}-5-nitro-2-indolinone (25%) with trifluoroacetic acid in methylene chloride.

Yield: 75% of theory; Melting point: 238–241° C.; $C_{25}H_{21}N_5O_3 \times CF_3COOH$; Calc.: C, 58.59; H, 4.01; N, 12.65; Found: 58.45; 3.99; 12.62; Calc.: molar peak $M^+=439$; Found: molar peak $M^+=439$.

EXAMPLE 15

3-{(Z)-1-[4-(1H-imidazol-4-yl)anilino]-1-(3-aminomethyl-phenyl)methylidene}-2-indolinone Prepared from 3-{(Z)-1-[4-(1H-imidazol-4-yl)anilino]-1-(3-cyano-phenyl)methylidene}-2-indolinone by catalytic hydrogenation on Raney nickel in saturated methanolic ammonia (20° C., 3.5 bar, 3 hours), evaporation in vacuo and trituration with ether.

Yield: 83% of theory; Melting point: from 101° C. (decomposition); DC-$R_f$=0.32 [silica gel; methylene chloride/methanol/conc. ammonia (100:10:1)]; $C_{25}H_{21}N_5O$; Calc.: molar peak $M^+=407$; Found: molar peak $M^+=407$.

EXAMPLE 16

3-{(Z)-1-[4-(2-amino-1H-imidazol-4-yl)anilino]-1-phenylmethylidene}-2-indolinone×H₂O Prepared from 3-{(Z)-1-[4-(imidazo[1,2-a]pyrimidin-2-yl)anilino]-1-phenylmethylidene}-2-indolinone×0.5 H₂O and 13 equivalents of hydrazine-hydrate in EtOH by refluxing (for 72 hours), evaporation in vacuo and purification by column chromatography on Al₂O₃ with CH₂Cl₂/MeOH (10:1) as eluant.

Yield: 21.8% of theory; Melting point: 250–255° C.; $C_{24}H_{19}N_5O \times H_2O$; Calc.: C, 70.06; H, 5.14; N, 17.02; Found: 70.11; 5.17; 17.17; Calc.: molar peak $M^+=393$; Found: molar peak $M^+=393$.

EXAMPLE 17

3-{(Z)-1-[4-(1H-imidazol-4-yl)anilino]-1-(4-aminomethyl-phenyl)methylidene}5-nitro-2-indolinone×H₂O (a) 1-acetyl-3-[1-hydroxy-1-(4-phthalimidomethyl-phenyl)methylidene}-5-nitro-2-indolinone Prepared analogously to Example 10 from 1-acetyl-5-nitro-2-indolinone and 4-phthalimidomethyl-benzoic acid (melting point: 260–262° C.; obtained from the corresponding tert.butyl ester, melting point 142–145° C. with TFA) in dry DMF in the presence of TBTU, HOBT and Hünig's base (20° C., for 2 hours), stirring in dilute hydrochloric acid, digesting the precipitate obtained in EtOac and drying the solid substance at 100° C. in vacuo.

Yield: 85% of theory; Melting point: 241–242° C.; Enol reaction (with FeCl₃ solution in EtOH): positive.

(b) 1-acetyl-3-[1-chloro-1-(4-phthalimidomethyl-phenyl)methylidene}-5-nitro-2-indolinone The enol obtained in (a) above is heated analogously to Example 11(b) with 2 equivalents of PCl₅ in toluene (90° C./6 hours and 110° C./6 hours), the precipitate formed on cooling was isolated, washed with toluene and dried at 75° C. in vacuo.

Yield: 65% of theory; Melting point: 234–236° C.; $C_{25}H_{20}N_6O_3 \times H_2O$; Calc.: C, 62.22; H, 3.21; N, 8.37; Cl, 7.06; Found: 62.25; 3.31; 8.27; 7.20; Calc.: molar peak $M^+=501/503$ (1 Cl); Found: molar peak $M^+=501/503$ (1 Cl).

(c) 1-acetyl-3-{(Z)-1-[4-(1H-imidazol-4-yl)anilino]-1-(4-phthalimidomethyl-phenyl)methylidene}-5-nitro-2-indolinone A solution of 0.50 g (1 mmol) of the chlorine compound obtained in (b) in 20 ml of CH₂Cl₂ is added to a cold ($T_i$=–60° C.) stirred suspension of 0.35 g (1.5 mmol) of 4-(1H-imidazol-4-yl)aniline×2 HCl (melting point: 350° C.) and 0.77 ml (4.5 mmol) of Hünig's base in 20 ml CH₂Cl₂ and stirred overnight at ambient temperature. After evaporation in vacuo and evaporation twice with toluene in vacuo the residue obtained is triturated with EtOH.

Yield (crude): 0.47 g (75% of theory); Melting point: 200° C.; $C_{35}H_{24}N_6O_6$; Calc.: molar peak $M^+=624$; Found: molar peak $M^+=624$.

(d) 3-{(Z)-1-[4-(1H-imidazol-4-yl)anilino]-1-(4-aminomethyl-phenyl)methylidene}-5-nitro-2-indolinone× H₂O 0.45 g (0.72 mmol) of the compound obtained in (c) is heated together with 0.1 ml of 80% hydrazine-hydrate (1.6 mmol) in 20 ml of CH₂Cl₂/EtOH (1:1) for 6 hours at 50° C. The mixture is evaporated down in vacuo and the evaporation residue is purified by column chromatography on silica gel with CH₂Cl₂/EtOH/conc. ammonia (5:2:0.05) as eluant.

Yield: 0.10 g (30.7% of theory); Melting point: 270–275° C.; $C_{25}H_{20}N_6O_2 \times H_2O$; Calc.: C, 63.82; H, 4.71; N, 17.86; Found: 64.26; 5.13; 17.20; Calc.: molar peak $M^+=452$; Found: molar peak $M^+=452$.

The following compound was obtained analogously to Example 17:

17.1 3-{(Z)-1-[4-(1H-imidazol-4-yl)anilino]-1-(4-aminomethyl-phenyl)methylidene}-2-indolinone (a) 1-acetyl-3-[1-hydroxy-1-(4-phthalimidomethyl-phenyl)methylidene}-2-indolinone Prepared analogously to Example 10(a) from 1-acetyl-2-indolinone and 4-phthalimidomethyl-benzoic acid (melting point: 260–262° C.) in dry DMF in the presence of TBTU, HOBT and Hrinig's base (20° C., 4 hours), stirring in dilute hydrochloric acid, extracting with CH₂Cl₂, evaporating the dried organic extract in vacuo, triturating the evaporation residue with EtOac and drying the solid substance.

Yield: 69% of theory; Melting point: 200–201° C.; Enol reaction (with FeCl₃ solution in EtoH): positive.

(b) 1-acetyl-3-[1-chloro-1-(4-phthalimidomethyl-phenyl)methylidene}-2-indolinone Prepared analogously to Example 11(b) from the enol obtained in (a) with 2 equivalents of PCl₅ in toluene (100° C./1 hour), evaporated down in vaczio until it starts to turn cloudy, petroleum ether is added, the precipitate formed is isolated, washed with petroleum ether and dried at 75° C. in vacuo.

Yield: 85% of theory; Melting point: 207–208° C.; $C_{26}H_{17}ClN_2O_4$; Calc.: molar peak $M^+=456/458$ (1 Cl); Found: molar peak $M^+=456/458$ (1 Cl).

(c) 1-acetyl-3-{(Z)-1-[4-(1H-imidazol-4-yl)anilino]-1-(4-phthalimidomethyl-phenyl)methylidene}-2-indolinone Prepared from the chlorine compound obtained in (b) and two equivalents of 4-(1H-imidazol-4-yl)aniline×2 HCl (melting point: 350° C.) and 3 equivalents of Hünig's base in DMF (80° C., 1 hour), by the addition of EtOac and washing with water, evaporation of the organic phase in vacuo and purification of the evaporation residue by column chromatography on silica gel with $CH_2Cl_2$/EtOH/conc. ammonia (15:1:0.1) as eluant.

Yield: 26% of theory (foam); Melting point: 200° C.; $C_{35}H_{25}N_6O_4$; Calc.: molar peak $M^+$=579; Found: molar peak $M^+$=579.

(d) 3-{(Z)-1-[4-(1H-imidazol-4-yl)anilino]-1-(4-aminomethyl-phenyl)methylidene}-2-indolinone Prepared from the compound obtained in (c) together with 3 equivalents of hydrazine-hydrate in EtOH (70° C./4 hours), evaporation in vacuo and final purification by column chromatography on silica gel with $CH_2Cl_2$/EtOH/conc. ammonia (4:1:0.1) as eluant.

Yield: 50% of theory; Melting point: 224–225° C.; $C_{25}H_{21}N_5O$; Calc.: molar peak $M^+$=407; Found: molar peak $M^+$=407.

EXAMPLE 18

3-{(Z)-1-[4-(1H-imidazol-4-yl)anilino]-1-(4-acetylaminomethyl-phenyl)methylidene}-5-nitro-2-indolinone 3-{(Z)-1-[4-(1H-imidazol-4-yl)anilino]-1-(4-aminomethyl-phenyl)methylidene}-5-nitro-2-indolinone×$H_2O$ is stirred into dry dioxane together with 1.2 equivalents of acetic anhydride and a few drops of glacial acetic acid overnight at ambient temperature. The mixture is evaporated down in vacuo and the evaporation residue is triturated with ether.

Yield: 83% of theory; Melting point: 170° C.; $C_{27}H_{22}N_6O_4$; Calc.: molar peak $M^+$=494; Found: molar peak $M^+$=494.

The following compounds were obtained analogously to Example 18:

18.1 3-{(Z)-1-[4-(1H-imidazol-4-yl)anilino]-1-(4-N-acetylaminomethyl-phenyl)methylidene}-2-indolinone Prepared from 3-{(Z)-1-[4-(1H-imidazol-4-yl)anilino]-1-(4-aminomethyl-phenyl)methylidene}-2-indolinone in dry dioxane with acetic anhydride and some glacial acetic acid (ambient temperature, 24 hours), evaporation in vacuo and trituration of the evaporation residue with ether.

Yield: 88% of theory; Melting point: 186–188° C.; $C_{27}H_{23}N_5O_2$; Calc.: molar peak $M^+$=449; Found: molar peak $M^+$=449.

18.2 3-{(Z)-1-[(2-acetyl-1,2,3,4-tetrahydro-isoquinolin-6-yl)-amino]-1-phenylmethylidene}-5-nitro-2-indolinone Prepared from 3-{(Z)-1-[(1,2,3,4-tetrahydro-isoquinolin-6-yl)-amino]-1-phenylmethylidene}-5-nitro-2-indolinone×HCl×$H_2O$ in glacial acetic acid with acetic anhydride in the presence of Hünig's base.

Yield: 83% of theory; Melting point: 285–286° C.; $C_{26}H_{22}N_4O_4$; Calc.: C, 68.69; H, 4.88; N, 12.32; Found: 68.34; 4.81; 12.27; Calc.: molar peak $M^+$=454; Found: molar peak $M^+$=454.

EXAMPLE 19

3-{(Z)-1-[4-(3-(rac-4-aminocarbonyl-2-oxo-pyrrolidin-1-yl)-(Z)-1-propen-1-yl)anilino]-1-phenylmethylidene}-5-nitro-2-indolinone (I) and 3-{(Z)-1-[4-(3-(rac-4-aminocarbonyl-2-oxo-pyrrolidin-1-yl)-(E)-1-propen-1-yl)anilino]-1-phenylmethylidene}-5-nitro-2-indolinone (II)

(a) 3-[(Z)-1-(4-bromo-anilino)-1-phenylmethylidene]-5-nitro-2-indolinone

Prepared by reacting 1-acetyl-3-(1-ethoxy-1-phenyl-methylidene)-5-nitro-2-indolinone with 1.5 equivalents of 4-bromo-aniline in DMF (110° C., for 2 hours), subsequent treatment with piperidine (20° C., 0.5 hours) and precipitation with water.

Yield: 92% of theory; Melting point: 300–305° C.; $C_{21}H_{14}BrN_3O_3$; Calc.: C, 57.82; H, 3.23; N, 9.63; Br, 18.32 Found: 57.81; 3.20; 9.65; 18.22; Calc.: molar peak $M^+$=435/437 1 (Br); Found: molar peak $M^+$=435/437 (1 Br).

(b) (I) and (II)

440 mg (1.0 mmol) of the 4-bromophenyl compound obtained in (a), 21 mg (0.069 mmol) of tri-o-tolyl-phosphine, 5 mg (0.023 mmol) of palladium diacetate, 185 mg (1.1 mmol) of rac-1-allyl-4-aminocarbonyl-2-oxo-pyrrolidine (melting point: 69–70° C.) and 0.35 ml (2.0 mmol) of Hünig's base are stirred in 20 ml of DMF for 15 hours at 100° C., filtered over kieselguhr, poured onto water, the precipitate is filtered off and purified by column chromatography on silica gel with $CH_2Cl_2$/MeOH (10:1) as eluant.

The (Z) isomer (I) is eluted first ($R_f$=0.50) and crystallised with ether: 3-{(Z)-1-[4-(3-(rac-4-aminocarbonyl-2-oxo-pyrrolidin-1-yl)-(Z)-1-propen-1-yl)anilino]-1-phenylmethylidene}-5-nitro-2-indolinone.

Yield: 131 mg (91% of theory); Melting point: 170° C. (foam); $C_{29}H_{25}N_5O_5$; Calc.: molar peak $M^+$=523; Found: molar peak $M^+$=523.

Then the (E) isomer (II) is eluted ($R_f$=0.43) and crystallised from MeOH (+ether).

3-{(Z)-1-[4-(3-(rac-4-aminocarbonyl-2-oxo-pyrrolidin-1-yl)-(E)-1-propen-1-yl)anilino]-1-phenylmethylidene}-5-nitro-2-indolinone.

Yield: 147 mg (14% of theory); Melting point: 220–225° C.; $C_{29}H_{25}N_5O_5$; Calc.: molar peak $M^+$=523; Found: molar peak $M^+$=523.

The following compounds were obtained analogously to Example 19:

19.1 3-{(Z)-1-[4-(3-(2-oxo-pyrrolidin-1-yl)-(Z)-1-propen-1-yl)-anilino]-1-phenylmethylidene}-5-nitro-2-indolinone (I) and 3-{(Z)-1-[4-(3-(2-oxo-pyrrolidin-1-yl)-(E)-1-propen-1-yl)anilino]-1-phenylmethylidene}-5-nitro-2-indolinone (II)

Prepared by reacting 3-[(Z)-1-(4-(4-bromo-anilino)-1-phenylmethylidene]-5-nitro-2-indolinone with 1.1 equivalents of N-allyl-pyrrolidin-2-one, 0.07 equivalents of tri-(o-tolyl)-phosphine, 0.02 equivalents of palladium diacetate and 2 equivalents of Hünig's base in DMF (3 hours, 100° C.; under nitrogen), filtering over kieselguhr, adding water and purifying the precipitate obtained by column chromatography on silica gel with EtOac/EtOH (10:1) as eluant.

The (Z) isomer (I) is eluted first ($R_f$=0.63): 3-{(Z)-1-[4-(3-(2-oxo-pyrrolidin-1-yl)-(Z)-1-propen-1-yl)anilino]-1-phenylmethylidene-}-5-nitro-2-indolinone.

Yield: 22% of theory; Melting point: 262–263° C.; $C_{28}H_{24}N_4O_4$; Calc.: C, 69.99; H, 5.03; N, 11.66; Found: 69.50; 5.30; 11.45; Calc.: molar peak $(M-H)^-$=479; Found: molar peak $(M-H)^-$=479.

Then the (E) isomer (II) is eluted ($R_f$=0.41):

3-{(Z)-1-[4-(3-(2-oxo-pyrrolidin-1-yl)-(E)-1-propen-1-yl)anilino]-1-phenylmethylidene}-5-nitro-2-indolinone.

Yield: 19% of theory; Melting point: 278–280° C.; $C_{28}H_{24}N_4O_4$; Calc.: C, 69.99; H, 5.03; N, 11.66; Found: 69.78; 5.24; 11.49; Calc.: molar peak $(M-H)^-$=479; Found: molar peak $(M-H)^-$=479.

19.2 Mixture of 3-{(Z)-1-[4-(2-(2-oxo-pyrrolidin-1-yl)-(Z)-ethen-1-yl)anilino]-1-phenylmethylidene}-5-nitro-2-indolinone (1) and 3-{(Z)-1-[4-(2-(2-oxo-pyrrolidin-1-yl)-(E)-ethen-1-yl)anilino]-1-phenylmethylidene}-5-nitro-2-indolinone (II)

Prepared by reacting 3-[(Z)-1-(4-(4-bromo-anilino)-1-phenylmethylidene]-5-nitro with 1.5 equivalents of N-vinylpyrrolidon-2-ine, 0.07 equivalents of tri-(o-tolyl)phosphine, 0.02 equivalents of palladium diacetate and 2 equivalents of Hünig's base in DMF (for 2 hours, 100° C.), filtering over kieselguhr, adding with water and purifying the resulting precipitate by column chromatography on silica gel with toluene/EtOac/EtOH (4:2:1) as eluant.

A mixture of (Z/E) isomers is obtained ($R_f$=0.48 and 0.40): Yield: 54.9% of theory; Melting point: 260–265° C.; $C_{27}H_{22}N_4O_4 \times 0.3\ H_2O$; Calc.: C, 68.71; H, 4.83; N, 11.87; Found: 68.72; 5.10; 11.68; Calc.: molar peak $M^+$=466; Found: molar peak $M^+$=466.

The following compounds may be prepared analogously to the preceding Examples:

(1) 3-{(Z)-1-[(indol-5-yl)amino]-1-phenylmethylidene}-5-nitro-2-indolinone, (2) 3-{(Z)-1-[(-methyl-benzimidazol-5-yl)amino]-1-phenylmethylidene}-5-nitro-2-indolinone, (3) 3-{(Z)-1-[(2-azaindol-5-yl)amino]-1-phenylmethylidene}-5-nitro-2-indolinone, (4) 3-{(Z)-1-[(2-indazol-6-yl)amino]-1-phenylmethylidene}-5-nitro-2-indolinone, (5) 3-{(Z)-1-[(2-oxo-indolin-5-yl)amino]-1-phenylmethylidene}-5-nitro-2-indolinone, (6) 3-{(Z)-1-[(1,2,3,4-tetrahydro-quinolin-6-yl)amino]-1-phenylmethylidene}-5-nitro-2-indolinone, (7) 3-{(Z)-1-[(benzimidazol-5-yl)amino]-1-phenylmethylidene}-5-nitro-2-indolinone, (8) 3-{(Z)-1-[(1-methyl-2-oxo-2,3-dihydro-1H-benzimidazol-5-yl)amino]-1-phenylmethylidene}-5-nitro-2-indolinone, (9) 3-{(Z)-1-[(quinolin-6-yl)amino]-1-phenylmethylidene}-5-nitro-2-indolinone,

(10) 3-{(Z)-1-[(2-oxo-1,2-dihydro-pyrazin-7-yl)amino]-1-phenylmethylidene}-5-nitro-2-indolinone,

(11) 3-{(Z)-1-[(isoquinolin-5-yl)amino]-1-phenylmethylidene}-5-nitro-2-indolinone,

(12) 3-{(Z)-1-[(2-Boc-1,2,3,4-tetrahydro-isoquinolin-5-yl)amino]-1-phenylmethylidene}-5-nitro-2-indolinone,

(13) 3-{(Z)-1-[(2-ethoxycarbonylmethyl-1,3-dioxo-isoindolin-5-yl)amino]-1-phenylmethylidene}-5-nitro-2-indolinone,

(14) 3-{(Z)-1-[(2-(3-ethoxycarbonyl-propyl)-1,3-dioxo-isoindolin-5-yl)amino]-1-phenylmethylidene}-5-nitro-2-indolinone

(15) 3-{(Z)-1-[4-(1H-imidazol-4-yl)anilino]-1-(3-cyano-phenyl)methylidene}-5-nitro-2-indolinone

(16) 3-{(Z)-1-[3-(1H-imidazolin-2-yl)anilino]-1-phenylmethylidene}-5-nitro-2-indolinone,

(17) 3-{(Z)-1-[4-(1,2,3,4-tetrahydro-isoquinolin-(5)-yl)amino]-1-phenylmethylidene}-5-nitro-2-indolinone-hydrochloride,

(18) 3-{(Z)-1-[4-(1H-imidazol-4-yl)anilino]-1-(3-aminomethyl-phenyl)methylidene}-5-nitro-2-indolinone,

(19) 3-{(Z)-1-[4-(2-amino-1H-imidazol-4-yl)anilino]-1-phenylmethylidene}-5-nitro-2-indolinone,

(20) 3-{(Z)-1-[4-((pyrrolidin-1-yl)methyl)anilino]-1-phenylmethylidene}-2-indolinone,

(21) 3-{(Z)-1-[4-(2-amino-5-methyl-1H-imidazol-4-yl)anilino]-1-phenylmethylidene}-2-indolinone,

(22) 3-{(Z)-1-[4-(2-amino-1H-thiazole-4-yl)anilino]-1-phenylmethylidene}-2-indolinone,

(23) 3-{(Z)-1-[4-((imidazol-1-yl)methyl)anilino]-1-phenylmethylidene}-2-indolinone,

(24) 3-{(Z)-1-[4-((2-oxo-pyrrolidin-1-yl)methyl)anilino]-1-phenylmethylidene}-2-indolinone,

(25) 3-{(Z)-1-[3-((2-oxo-pyrrolidin-1-yl)methyl)anilino]-1-phenylmethylidene}-2-indolinone,

(26) 3-{(Z)-1-[2-(1H-imidazol-4-yl)anilino]-1-phenylmethylidene}-2-indolinone,

(27) 3-{(Z)-1-[4-(2-amino-1H-imidazol-4-yl)anilino]-1-phenylmethylidene}-2-indolinone,

(28) 3-{(Z)-1-[4-((2,4-dioxo-imidazolidin-5-yl)methyl)anilino]-1-phenylmethylidene}-2-indolinone,

(29) 3-{(Z)-1-[4-((2,4-dioxo-imidazolidin-5-ylidene)methyl)anilino]-1-phenylmethylidene}-2-indolinone,

(30) 3-{(Z)-1-[4-(2-methyl-1H-imidazol-4-yl)anilino]-1-phenylmethylidene}-2-indolinone,

(31) 3-{(Z)-1-[4-(1-methyl-1H-imidazole-5-yl)anilino]-1-1-phenylmethylidene}-2-indolinone,

(32) 3-{(Z)-1-[4-(2-acetylamino-1H-imidazol-4-yl)anilino]-1-phenylmethylidene}-2-indolinone,

(33) 3-{(Z)-1-[4-(2-acetylamino-5-methyl-1H-imidazol-4-yl)anilino]-1-phenylmethyledene}-2-indolinone,

(34) 3-{(Z)-1-[4-(1H-tetrazol-5-yl)anilino]-1-phenylmethylidene}-2-indolinone,

(35) 3-{(Z)-1-[4-((imidazol-4-yl)methyl)anilino]-1-phenylmethylidene}-2-indolinone,

(36) 3-{(Z)-1-[4-(2-(imidazol-4-yl)ethyl)anilino]-1-phenylmethylidene}-2-indolinone,

(37) 3-{(Z)-1-[4-(2-(imidazol-4-yl)-(E)-ethenyl)anilino]-1-phenylmethylidene}-2-indolinone,

(38) 3-{(Z)-1-[4-((2,4-dioxo-thiazolidin-5-ylidene)methyl)anilino]-1-phenylmethylidene}-2-indolinone,

(39) 3-{(Z)-1-[4-((2,4-dioxo-thiazolidin-5-yl)-methyl)-anilino]-1-phenylmethylidene}-2-indolinone,

(40) 3-{(Z)-1-[4-(1H-imidazol-4-yl)anilino]-1-(4-trifluoromethyl-phenyl)methylidene}-2-indolinone,

(41) 3-{(Z)-1-[4-(1H-imidazol-4-yl)anilino]-1-(4-methyl-pheyl)phethylidene[sic]}-2-indolinone,

(42) 3-{(Z)-1-[4-(2-isobutyl-1H-imidazol-4-yl)anilino]-1-phenylmethylidene}-5-nitro-2-indolinone,

(43) 3-{(Z)-1-[4-[(1-Boc-imidazolin-2-yl)methyl]anilino]-1-phenylmethylidene}-5-nitro-2-indolinone

(44) 3-{(Z)-1-[4-[(imidazolin-2-yl)methyl]anilino]-1-phenylmethylidene}-5-nitro-2-indolinone,

(45) 3-{(Z)-1-[4-[(imidazolin-1-yl)methyl]anilino]-1-phenylmethylidene}-5-nitro-2-indolinone,

(46) 3-{(Z)-1-[4-[(5-methoxycarbonyl-2-oxo-pyrrolidin-1-yl)methyl]anilino]-1-phenylmethylidene}-5-nitro-2-indolinone,

(47) 3-{(Z)-1-[4-[(5-carboxy-2-oxo-pyrrolidin-1-yl)methyl]anilino]-1-phenylmethylidene}-5-nitro-2-indolinone,

(48) 3-{(Z)-1-[4-[(pyrrol-1-yl)methyl]anilino]-1-phenylmethylidene}-5-nitro-2-indolinone,

(49) 3-{(Z)-1-[4-[(2,5-dihydro-2,5-dioxo-pyrrol-1-yl)methyl]anilino]-1-phenylmethylidene}-5-nitro-2-indolinone,

(50) 3-{(Z)-1-[4-[(2,5-dioxo-pyrrolidin-1-yl)methyl]anilino]-1-phenylmethylidene}-5-nitro-2-indolinone,

(51) 3-{(Z)-1-[4-[(3-oxo-pyrrolidin-1-yl)methyl]anilino]-1-phenylmethylidene}-5-2-indolinone,

(52) 3-{(Z)-1-[4-(imidazol-1-yl)anilino]-1-phenylmethylidene}-5-nitro-2-indolinone,

(53) 3-{(Z)-1-[4-(3,5-dioxo-tetrahydro-1,2,4-triazol-4-yl)anilino]-1-phenylmethylidene}-5-nitro-2-indolinone,

(54) 3-{(Z)-1-[4-(2,4-dioxo-imidazolin-5-yl)anilino]-1-phenylmethylidene}-5-nitro-2-indolinone,

(55) 3-{(Z)-1-[4-[(3-methyl-2,4-dioxo-imidazolin-5-ylidene)methyl]anilino]-1-phenylmethylidene}-5-nitro-2-indolinone,

(56) 3-{(Z)-1-[4-[(1,3-dimethyl-2,4-dioxo-imidazolin-5-ylidene)methyl]anilino]-1-phenylmethylidene}-5-nitro-2-indolinone,

(57) 3-{(Z)-1-[4-[(1-methyl-2,4-dioxo-imidazolin-5-yl)methyl]anilino]-1-phenylmethylidene}-5-nitro-2-indolinone,

(58) 3-{(Z)-1-[4-[(3-methyl-2,4-dioxo-imidazolin-5-yl)methyl]anilino]-1-phenylmethylidene}-5-nitro-2-indolinone,
(59) 3-{(Z)-1-[4-[(1,3-dimethyl-2,4-dioxo-imidazolin-5-yl)methyl]anilino]-1-phenylmethylidene}-5-nitro-2-indolinone,
(60) 3-{(Z)-1-[4-[1-(imidazol-4-yl)ethen-1-yl]anilino]-1-phenylmethylidene}-5-nitro-2-indolinone,
(61) 3-{(Z)-1-[4-[1-(imidazol-4-yl)ethyl]anilino]-1-phenylmethylidene}-5-nitro-2-indolinone,
(62) 3-{(Z)-1-[3-[1-(imidazol-4-yl)-3-propen-1-yl]anilino]-1-phenylmethylidene}-5-nitro-2-indolinone,
(63) 3-{(Z)-1-[3-[1-(imidazol-4-yl)-1-propen-1-ylanilino]-1-phenylmethylidene}-5-nitro-2-indolinone,
(64) 3-{(Z)-1-[3-[1-(imidazol-4-yl)propyl]anilino]-1-phenylmethylidene}-5-nitro-2-indolinone,
(65) 3-{(Z)-1-[4-[3-(5-aminocarbonyl-2-oxo-pyrrolidin-1-yl)-1-propen-1-yl]anilino]-1-phenylmethylidene}-5-nitro-2-indolinone,
(66) 3-{(Z)-1-[4-[3-(5-aminocarbonyl-2-oxo-pyrrolidin-1-yl)-propyl]anilino]-1-phenylmethylidene}-5-nitro-2-indolinone,
(67) 3-{(Z)-1-[4-[3-(pyrrolidin-1-yl)-1-propen-1-yl]anilino]-1-phenylmethylidene}-5-nitro-2-indolinone,
(68) 3-{(Z)-1-[4-[3-(pyrrolidin-1-yl)-propyl]anilino]-1-phenylmethylidene}-5-nitro-2-indolinone,
(69) 3-{(Z)-1-[4-[(2-oxo-pyrrolidin-1-yl)-1-propen-1-yl]anilino]-1-phenylmethylidene}-5-nitro-2-indolinone,
(70) 3-{(Z)-1-[4-[(2-oxo-pyrrolidin-1-yl)-propyl]anilino]-1-phenylmethylidene}-5-nitro-2-indolinone,
(71) 3-{(Z)-1-[3-(1-methyl-1H-imidazol-4-yl)anilino]-1-phenylmethylidene}-2-indolinone,
(72) 3-{(Z)-1-[3-(1H-imidazol-4-yl)anilino]-1-(4-trifluoromethyl-phenyl)methylidene}-5-nitro-2-indolinone,
(73) 3-{(Z)-1-[3-(1H-imidazol-4-yl)anilino]-1-(4-methyl-phenyl)methylidene}-5-nitro-2-indolinone,
(74) 3-{(Z)-1-[3-(2-acetylamino-1H-imidazol-4-yl)anilino]-1-phenylmethylidene}-5-nitro-2-indolinone,
(75) 3-{(Z)-1-[3-(2-methyl-1H-imidazol-4-yl)anilino]-1-phenylmethylidene}-5-nitro-2-indolinone,
(76) 3-{(Z)-1-[3-((pyrrolidin-1-yl)methyl)anilino]-1-phenylmethylidene}-5-nitro-2-indolinone,
(77) 3-{(Z)-1-[3-(2-(imidazol-4-yl)-(E)-ethenyl)anilino]-1-phenylmethylidene}-5-nitro-2-indolinone,
(78) 3-{(Z)-1-[3-((-methyl-2,4-dioxo-imidazolidin-5-(E/Z)-ylidene)methyl)anilino]-1-phenylmethylidene}-5-nitro-2-indolinone,
(79) 3-{(Z)-1-[3-(2-ethyl-1H-imidazol-4-yl)anilino]-1-phenyl-methylidene}-5-nitro-2-indolinone,
(80) 3-{(Z)-1-[4-[2-(2-oxo-pyrrolidin-1-yl)ethen-1-yl]anilino]-1-phenylmethylidene}-5-nitro-2-indolinone,
(81) 3-{(Z)-1-[4-[2-(2-oxo-pyrrolidin-1-yl)ethyl]anilino]-1-phenylmethylidene}-5-nitro-2-indolinone,
(82) 3-{(Z)-1-[4-[1-(pyrrolidin-1-yl)ethyl]anilino]-1-phenylmethylidene}-5-nitro-2-indolinone,
(83) 3-{(Z)-1-[4-[1-(2-oxo-pyrrolidin-1-yl)ethyl]anilino]-1-phenylmethylidene}-5-nitro-2-indolinone,
(84) 3-{(Z)-1-[4-[(2-methyl-pyrrolidin-1-yl)methyl]anilino]-1-phenylmethylidene}-5-nitro-2-indolinone,
(85) 3-{(Z)-1-[4-[(3-methyl-pyrrolidin-1-yl)methyl]anilino]-1-phenylmethylidene}-5-2-indolinone,
(86) 3-{(Z)-1-[4-[(pyrrolidin-2-yl)methyl]anilino]-1-phenylmethylidene}-5-nitro-2-indolinone,
(87) 3-{(Z)-1-[4-[(1-methyl-pyrrolidin-2-yl)methyl]anilino]-1-phenylmethylidene}-5-nitro-2-indolinone,
(88) 3-{(Z)-1-[4-[(1-acetyl-pyrrolidin-2-yl)methyl]anilino]-1-phenylmethylidene}-5-nitro-2-indolinone,
(89) 3-{(Z)-1-[4-[(pyrrolidin-3-yl)methyl]anilino]-1-phenylmethylidene}-5-nitro-2-indolinone,
(90) 3-{(Z)-1-[4-[(1-methyl-pyrrolidin-3-yl)methyl]anilino]-1-phenylmethylidene}-5-nitro-2-indolinone,
(91) 3-{(Z)-1-[4-[(1-acetyl-pyrrolidin-3-yl)methyl]anilino]-1-phenylmethylidene}-5-nitro-2-indolinone,
(92) 3-{(Z)-1-[4-[(2-oxo-pyrrolidin-5-yl)methyl]anilino]-1-phenylmethylidene}-5-nitro-2-indolinone,
(93) 3-{(Z)-1-[4-[(2-oxo-pyrrolidin-3-yl)methyl]anilino]-1-phenylmethylidene}-5-nitro-2-indolinone,
(94) 3-{(Z)-1-[4-[(2-oxo-pyrrolidin-4-yl)methyl]anilino]-1-phenylmethylidene-5-nitro-2-indolinone,
(95) 3-{(Z)-1-[4-[(2,5-dioxo-pyrrolidin-3-yl)methyl]anilino]-1-phenylmethylidene}-5-nitro-2-indolinone,
(96) 3-{(Z)-1-[4-[(2,5-dioxo-2,5-dihydro-pyrrol-3-yl)methyl]anilino]-1-phenylmethylidene}-5-nitro-2-indolinone,
(97) 3-{(Z)-1-[4-[(2-hydroxymethyl-pyrrolidin-1-yl)methyl]anilino]-1-phenylmethylidene}-5-nitro-2-indolinone,
(98) 3-{(Z)-1-[4-[(2-methoxymethyl-pyrrolidin-1-yl)methyl]anilino]-1-phenylmethylidene}-5-nitro-2-indolinone,
(99) 3-{(Z)-1-[4-[(2-ethoxycarbonyl-pyrrolidin-1-yl)methyl]anilino]-1-phenylmethylidene}-5-nitro-2-indolinone,
(100) 3-{(Z)-1-[4-[(pyrazol-1-yl)methyl]anilino]-1-phenylmethylidene}-5-nitro-2-indolinone,
(101) 3-{(Z)-1-[4-[(3-oxo-2,3-dihydro-pyrazol-1-yl)methyl]anilino]-1-phenylmethylidene}-5-nitro-2-indolinone,
(102) 3-{(Z)-1-[4-[(2-oxo-imidazolidin-1-yl)methyl]anilino]-1-phenylmethylidene}-5-nitro-2-indolinone,
(103) 3-{(Z)-1-[4-[(2-oxo-2,3-dihydro-imidazol-1-yl)methyl]anilino]-1-phenylmethylidene}-5-nitro-2-indolinone,
(104) 3-{(Z)-1-[4-(1-methyl-1H-imidazol-2-yl)anilino]-1-(4-aminomethyl-phenyl)-methylidene}-5-nitro-2-indolinone,
(105) 3-{(Z)-1-[4-(1-methyl-1H-imidazol-4-yl)anilino]-1-(4-aminomethyl-phenyl)-methylidene}-5-nitro-2-indolinone,
(106) 3-{(Z)-1-[4-(1H-imidazol-4-yl)anilino]-1-(4-aminomethyl-phenyl)-methylidene}-2-indolinone,
(107) 3-{(Z)-1-[4-(1H-imidazol-4-yl)anilino]-1-(4-aminomethyl-phenyl)-methylidene}-5-nitro-2-indolinone,
(108) 3-{(Z)-1-[4-(2-acetylamino-1H-imidazol-4-yl)anilino]-1-(4-aminomethyl-phenyl)-methylidene}-5-nitro-2-indolinone,
(109) 3-{(Z)-1-[4-(2-methyl-1H-imidazol-4-yl)anilino]-1-(4-aminomethyl-phenyl)-methylidene}-5-nitro-2-indolinone,
(110) 3-{(Z)-1-[(1,2,3,4-tetrahydro-isoquinolin-6-yl)amino]-1-(4-aminomethyl-phenyl)-methylidene}-5-nitro-2-indolinone,
(111) 3-{(Z)-1-[(2-acetyl-1,2,3,4-tetrahydro-isoquinolin-6-yl)amino]-1-(4-aminomethyl-phenyl)-methylidene}-5-nitro-2-indolinone,
(112) 3-{(Z)-1-[4-((2,4-dioxo-imidazolidin-5-ylidene)methyl)anilino]-1-(4-aminomethyl-phenyl)-methylidene}-5-nitro-2-indolinone,
(113) 3-{(Z)-1-[4-((pyrrolidin-1-yl)methyl)anilino]-1-(4-aminomethyl-phenyl)-methylidene}-5-nitro-2-indolinone,
(114) 3-{(Z)-1-[4-(2-(imidazol-4-yl)-(E)-ethenyl)anilino]-1-(4-aminomethyl-phenyl)-methylidene}-5-nitro-2-indolinone, (115) 3-{(Z)-1-[4-((1-methyl-2,4-dioxo-imidazolidin-5-(E/Z)-ylidene)methyl)anilino]-1-(4-aminomethyl-phenyl)-methylidene}-5-nitro-2-indolinone,
(116) 3-{(Z)-1-[4-(2-ethyl-1H-imidazol-4-yl)anilino]-1-(4-aminomethyl-phenyl)-methylidene}-5-nitro-2-indolinone,
(117) 3-{(Z)-1-[4-(1-methyl-1H-imidazol-2-yl)anilino]-1-(4-acetylaminomethyl-phenyl)-methylidene}-5-nitro-2-indolinone,
(118) 3-{(Z)-1-[4-(1-methyl-1H-imidazol-4-yl)anilino]-1-(4-acetylaminomethyl-phenyl)-methylidene}-5-nitro-2-indolinone,
(119) 3-{(Z)-1-[4-(1H-imidazol-4-yl)anilino]-1-(4-acetylaminomethyl-phenyl)-methylidene}-2-indolinone,
(120) 3-{(Z)-1-[4-(1H-imidazol-4-yl)anilino]-1-(4-acetylaminomethyl-phenyl)-methylidene}-5-nitro-2-indolinone,
(121) 3-{(Z)-1-[4-(2-acetylamino-1H-imidazol-4-yl)anilino]-1-(4-acetylaminomethyl-phenyl)-methylidene}-5-nitro-2-indolinone,
(122) 3-{(Z)-1-[4-(2-methyl-1H-imidazol-4-yl)anilino]-1-(4-acetylaminomethyl-phenyl)-methylidene}-5-nitro-2-indolinone,
(123) 3-{(Z)-1-[(1,2,3,4-tetrahydro-isoquinolin-6-yl)amino]-1-(4-acetylaminomethyl-phenyl)-methylidene}-5-nitro-2-indolinone,
(124) 3-{(Z)-1-[(2-acetyl-1,2,3,4-tetrahydro-isoquinolin-6-yl)amino]-1-(4-acetylaminomethyl-phenyl)-methylidene}-5-nitro-2-indolinone,
(125) 3-{(Z)-1-[4-((2,4-dioxo-imidazolidin-5-ylidene)methyl)anilino]-1-(4-acetylaminomethyl-phenyl)-methylidene}-5-nitro-2-indolinone,
(126) 3-{(Z)-1-[4-((pyrrolidin-1-yl)methyl)anilino]-1-(4-acetylaminomethyl-phenyl)-methylidene}-5-nitro-2-indolinone,
(127) 3-{(Z)-1-[4-(2-(imidazol-4-yl)-(E)-ethenyl)anilino]-1-(4-acetylaminomethyl-phenyl)-methylidene}-5-nitro-2-indolinone,
(128) 3-{(Z)-1-[4-((1-methyl-2,4-dioxo-imidazolidin-5-(E/Z)-ylidene)methyl)anilino]-1-(4-acetylaminomethyl-phenyl)-methylidene}-5-nitro-2-indolinone,
(129) 3-{(Z)-1-[4-(2-ethyl-1H-imidazol-4-yl)anilino]-1-(4-acetylaminomethyl-phenyl)-methylidene}-5-nitro-2-indolinone,
(130) 3-{(Z)-1-[4-(1-methyl-1H-imidazol-2-yl)anilino]-1-(4-pyrrolidinomethyl-phenyl)-methylidene}-5-nitro-2-indolinone,
(131) 3-{(Z)-1-[4-(1-methyl-1H-imidazol-4-yl)anilino]-1-(4-pyrrolidinomethyl-phenyl)-methylidene}-5-nitro-2-indolinone,
(132) 3-{(Z)-1-[4-(1H-imidazol-4-yl)anilino]-1-(4-pyrrolidinomethyl-phenyl)-methylidene}-2-indolinone,
(133) 3-{(Z)-1-[4-(1H-imidazol-4-yl)anilino]-1-(4-pyrrolidinomethyl-phenyl)-methylidene}-5-nitro-2-indolinone,
(134) 3-{(Z)-1-[4-(2-pyrrolidino-1H-imidazol-4-yl)anilino]-1-(4-pyrrolidinomethyl-phenyl)-methylidene}-5-nitro-2-indolinone,
(135) 3-{(Z)-1-[4-(2-methyl-1H-imidazol-4-yl)anilino]-1-(4-pyrrolidinomethyl-phenyl)-methylidene}-5-nitro-2-indolinone,
(136) 3-{(Z)-1-[(1,2,3,4-tetrahydro-isoquinolin-6-yl)amino]-1-(4-pyrrolidinomethyl-phenyl)-methylidene}-5-nitro-2-indolinone,
(137) 3-{(Z)-1-[(2-acetyl-1,2,3,4-tetrahydro-isoquinolin-6-yl)amino]-1-(4-pyrrolidinomethyl-phenyl)-methylidene}-5-nitro-2-indolinone,
(138) 3-{(Z)-1-[4-((2,4-dioxo-imidazolidin-5-ylidene)methyl)anilino]-1-(4-pyrrolidinomethyl-phenyl)-methylidene}-5-nitro-2-indolinone,
(139) 3-{(Z)-1-[4-((pyrrolidin-1-yl)methyl)anilino]-1-(4-pyrrolidinomethyl-phenyl)-methylidene}-5-nitro-2-indolinone,
(140) 3-{(Z)-1-[4-(2-(imidazol-4-yl)-(E)-ethenyl)anilino]-1-(4-pyrrolidinomethyl-phenyl)-methylidene}-5-nitro-2-indolinone,
(141) 3-{(Z)-1-[4-((1-methyl-2,4-dioxo-imidazolidin-5-(E/Z)-ylidene)methyl)anilino]-1-(4-acetylaminomethyl-phenyl)-methylidene}-5-nitro-2-indolinone,
(142) 3-{(Z)-1-[4-(2-ethyl-1H-imidazol-4-yl)anilino]-1-(4-pyrrolidinomethyl-phenyl-5 methylidene}-5-nitro-2-indolinone,
(143) 3-{(Z)-1-[4-(1-methyl-1H-imidazol-2-yl)anilino]-1-(4-piperidinomethyl-phenyl)-methylidene}-5-nitro-2-indolinone,
(144) 3-{(Z)-1-[4-(1-methyl-1H-imidazol-4-yl)anilino]-1-(4-piperidinomethyl-phenyl)-methylidene}-5-nitro-2-indolinone,
(145) 3-{(Z)-1-[4-(1H-imidazol-4-yl)anilino]-1-(4-piperidinomethyl-phenyl)-methylidene}-2-indolinone,
(146) 3-{(Z)-1-[4-(1H-imidazol-4-yl)anilino]-1-(4-piperidinomethyl-phenyl)-methylidene}-5-nitro-2-indolinone,
(147) 3-{(Z)-1-[4-(2-pyrrolidino-1H-imidazol-4-yl)anilino]-1-(4-piperidinomethyl-phenyl)-methylidene}-5-nitro-2-indolinone,
(148) 3-{(Z)-1-[4-(2-methyl-1H-imidazol-4-yl)anilino]-1-(4-piperidinomethyl-phenyl)-methylidene}-5-nitro-2-indolinone,
(149) 3-{(Z)-1-[(1,2,3,4-tetrahydro-isoquinolin-6-yl)amino]-1-(4-piperidinomethyl-phenyl)-methylidene}-5-nitro-2-indolinone,
(150) 3-{(Z)-1-[(2-acetyl-1,2,3,4-tetrahydro-isoquinolin-6-yl)amino]-1-(4-piperidinomethyl-phenyl)-methylidene}-5-nitro-2-indolinone,
(151) 3-{(Z)-1-[4-((2,4-dioxo-imidazolidin-5-ylidene)methyl)anilino]-1-(4-piperidinomethyl-phenyl)-methylidene}-5-nitro-2-indolinone,
(152) 3-{(Z)-1-[4-((pyrrolidin-1-yl)methyl)anilino]-1-(4-piperidinomethyl-phenyl)-methylidene}-5-nitro-2-indolinone,
(153) 3-{(Z)-1-[4-(2-(imidazol-4-yl)-(E)-ethenyl)anilino]-1-(4-piperidinomethyl-phenyl)-methylidene}-5-nitro-2-indolinone,
(154) 3-{(Z)-1-[4-((1-methyl-2,4-dioxo-imidazolidin-5-(E/Z)-ylidene)methyl)anilino]-1-(4-piperidinomethyl-phenyl)-methylidene}-5-nitro-2-indolinone,
(155) 3-{(Z)-1-[4-(2-ethyl-1H-imidazol-4-yl)anilino]-1-(4-piperidinomethyl-phenyl)-methylidene}-5-nitro-2-indolinone,
(156) 3-{(Z)-1-[4-(1-methyl-1H-imidazol-2-yl)anilino]-1-(4-(2-oxo-pyrrolidino-methyl)-phenyl)-methylidene}-5-nitro-2-indolinone,
(157) 3-{(Z)-1-[4-(1-methyl-1H-imidazol-4-yl)anilino]-1-(4-(2-oxo-pyrrolidino-methyl)-phenyl)-methylidene}-5-nitro-2-indolinone,
(158) 3-{(Z)-1-[4-(1H-imidazol-4-yl)anilino]-1-(4-(2-oxo-pyrrolidino-methyl)-phenyl)-methylidene}-2-indolinone,
(159) 3-{(Z)-1-[4-(1H-imidazol-4-yl)anilino]-1-(4-(2-oxo-pyrrolidino-methyl)-phenyl)-methylidene}-5-nitro-2-indolinone,
(160) 3-{(Z)-1-[4-(2-pyrrolidino-1H-imidazol-4-yl)anilino]-1-(4-(2-oxo-pyrrolidino-methyl)-phenyl)-methylidene}-5-nitro-2-indolinone, (161) 3-{(Z)-1-[4-(2-methyl-1H-imidazol-4-yl)anilino]-1-(4-(2-oxo-pyrrolidino-methyl)-phenyl)-methylidene}-5-nitro-2-indolinone,
(162) 3-{(Z)-1-[(1,2,3,4-tetrahydro-isoquinolin-6-yl)amino]-1-(4-(2-oxo-pyrrolidino-methyl)-phenyl)-methylidene}-5-nitro-2-indolinone,
(163) 3-{(Z)-1-[(2-acetyl-1,2,3,4-tetrahydro-isoquinolin-6-yl)amino]-1-(4-(2-oxo-pyrrolidino-methyl)-phenyl)-methylidene}-5-nitro-2-indolinone,
(164) 3-{(Z)-1-[4-((2,4-dioxo-imidazolidin-5-ylidene)methyl)anilino]-1-(4-(2-oxo-pyrrolidino-methyl)-phenyl)-methylidene}-5-nitro-2-indolinone,
(165) 3-{(Z)-1-[4-((pyrrolidin-1-yl)methyl)anilino]-1-(4-(2-oxo-pyrrolidino-methyl)-phenyl)-methylidene}-5-nitro-2-indolinone,
(166) 3-{(Z)-1-[4-(2-(imidazol-4-yl)-(E)-ethenyl)anilino]-1-(4-(2-oxo-pyrrolidino-methyl)-phenyl)-methylidene}-5-nitro-2-indolinone,
(167) 3-{(Z)-1-[4-((1-methyl-2,4-dioxo-imidazolidin-5-(E/Z)-ylidene)methyl)anilino]-1-(4-(2-oxo-pyrrolidino-methyl)-phenyl)-methylidene}-5-nitro-2-indolinone,
(168) 3-{(Z)-1-[4-(2-ethyl-1H-imidazol-4-yl)anilino]-1-(4-(2-oxo-pyrrolidino-methyl)-phenyl)-methylidene}-5-nitro-2-indolinone,
(169) 3-{(Z)-1-[4-(1-methyl-1H-imidazol-2-yl)anilino]-1-(4-(2-oxo-piperidino-methyl)-phenyl)-methylidene}-5-nitro-2-indolinone,
(170) 3-{(Z)-1-[4-(1-methyl-1H-imidazol-4-yl)anilino]-1-(4-(2-oxo-piperidino-methyl)-phenyl)-methylidene}-5-nitro-2-indolinone,
(171) 3-{(Z)-1-[4-(1H-imidazol-4-yl)anilino]-1-(4-(2-oxo-piperidino-methyl)-phenyl)-methylidene}-2-indolinone,
(172) 3-{(Z)-1-[4-(1H-imidazol-4-yl)anilino]-1-(4-(2-oxo-piperidino-methyl)-phenyl)-methylidene}-5-nitro-2-indolinone,
(173) 3-{(Z)-1-[4-(2-piperidino-1H-imidazol-4-yl)anilino]-1-(4-(2-oxo-piperidino-methyl)-phenyl)-methylidene}-5-nitro-2-indolinone,
(174) 3-{(Z)-1-[4-(2-methyl-1H-imidazol-4-yl)anilino]-1-(4-(2-oxo-piperidino-methyl)-phenyl)-methylidene}-5-nitro-2-indolinone,
(175) 3-{(Z)-1-[(1,2,3,4-tetrahydro-isoquinolin-6-yl)amino]-1-(4-(2-oxo-piperidino-methyl)-phenyl)-methylidene}-5-nitro-2-indolinone,
(176) 3-{(Z)-1-[(2-acetyl-1,2,3,4-tetrahydro-isoquinolin-6-yl)amino]-1-(4-(2-oxo-piperydino-methyl)-phenyl)-methylidene}-5-nitro-2-indolinone,
(177) 3-{(Z)-1-[4-((2,4-dioxo-imidazolidin-5-ylidene)methyl)anilino]-1-(4-(2-oxo-piperidino-methyl)-phenyl)-methylidene}-5-nitro-2-indolinone,
(178) 3-{(Z)-1-[4-((pyrrolidin-1-yl)methyl)anilino]-1-(4-(2-oxo-piperidino-methyl)-phenyl)-methylidene}-5-nitro-2-indolinone,
(179) 3-{(Z)-1-[4-(2-(imidazol-4-yl)-(E)-ethenyl)anilino]-1-(4-(2-oxo-piperidino-methyl)-phenyl)-methylidene}-5-nitro-2-indolinone,
(180) 3-{(Z)-1-[4-((1-methyl-2,4-dioxo-imidazolidin-5-(E/Z)-ylidene)methyl)anilino]-1-(4-(2-oxo-piperidino-methyl)-phenyl)-methylidene}-5-nitro-2-indolinone,
(181) 3-{(Z)-1-[4-(2-ethyl-1H-imidazol-4-yl)anilino]-1-(4-(2-oxo-piperidino-methyl)-phenyl)-methylidene}-5-nitro-2-indolinone,
(182) 3-{(Z)-1-[4-(1-methyl-1H-imidazol-2-yl)anilino]-1-(4-(2-amino-ethyl)-phenyl)-methylidene}-5-nitro-2-indolinone,
(183) 3-{(Z)-1-[4-(1-methyl-1H-imidazol-4-yl)anilino]-1-(4-(2-amino-ethyl)-phenyl)-methylidene}-5-nitro-2-indolinone,
(184) 3-{(Z)-1-[4-(1H-imidazol-4-yl)anilino]-1-(4-(2-amino-ethyl)-phenyl)-methylidene}-2-indolinone,
(185) 3-{(Z)-1-[4-(1H-imidazol-4-yl)anilino]-1-(4-(2-amino-ethyl)-phenyl)-methylidene}-5-nitro-2-indolinone,
(186) 3-{(Z)-1-[4-(2-piperidino-1H-imidazol-4-yl)anilino]-1-(4-(2-amino-ethyl)-phenyl)-methylidene}-5-nitro-2-indolinone,
(187) 3-{(Z)-1-[4-(2-methyl-1H-imidazol-4-yl)anilino]-1-(4-(2-amino-ethyl)-phenyl)-methylidene}-5-nitro-2-indolinone,
(188) 3-{(Z)-1-[(1,2,3,4-tetrahydro-isoquinolin-6-yl)amino]-1-(4-(2-amino-ethyl)-methylidene}-5-nitro-2-indolinone,
(189) 3-{(Z)-1-[(2-acetyl-1,2,3,4-tetrahydro-isoquinolin-6-yl)amino]-1-(4-(2-amino-ethyl)-phenyl)-methylidene}-5-nitro-2-indolinone,
(190) 3-{(Z)-1-[4-((2,4-dioxo-imidazolidin-5-ylidene)methyl)anilino]-1-(4-(2-amino-ethyl)-phenyl)-methylidene}-5-nitro-2-indolinone,
(191) 3-{(Z)-1-[4-((pyrrolidin-1-yl)methyl)anilino]-1-(4-(2-amino-ethyl)-phenyl)-methylidene}-5-nitro-2-indolinone,
(192) 3-{(Z)-1-[4-(2-(imidazol-4-yl)-(E)-ethenyl)anilino]-1-(4-(2-amino-ethyl)-phenyl)-methylidene}-5-nitro-2-indolinone,
(193) 3-{(Z)-1-[4-((-methyl-2,4-dioxo-imidazolidin-5-(E/Z)-ylidene)methyl)anilino]-1-(4-(2-amino-ethyl)-phenyl)-methylidene}-5-nitro-2-indolinone,
(194) 3-{(Z)-1-[4-(2-ethyl-1H-imidazol-4-yl)anilino]-1-(4-(2-amino-ethyl)-phenyl)-methylidene}-5-nitro-2-indolinone,
(195) 3-{(Z)-1-[4-(1-methyl-1H-imidazol-2-yl)anilino]-1-(4-(2-acetylamino-ethyl)-phenyl)-methylidene}-5-nitro-2-indolinone,
(196) 3-{(Z)-1-[4-(1-methyl-1H-imidazol-4-yl)anilino]-1-(4-(2-acetylamino-ethyl)-phenyl)-methylidene}-5-nitro-2-indolinone,
(197) 3-{(Z)-1-[4-(1H-imidazol-4-yl)anilino]-1-(4-(2-acetylamino-ethyl)-phenyl)-methylidene}-2-indolinone,
(198) 3-{(Z)-1-[4-(1H-imidazol-4-yl)anilino]-1-(4-(2-acetylamino-ethyl)-phenyl)-methylidene}-5-nitro-2-indolinone,
(199) 3-{(Z)-1-[4-(2-piperidino-1H-imidazol-4-yl)anilino]-1-(4-(2-acetylamino-ethyl)-phenyl)-methylidene}-5-nitro-2-indolinone,
(200) 3-{(Z)-1-[4-(2-methyl-1H-imidazol-4-yl)anilino]-1-(4-(2-acetylamino-ethyl)-phenyl)-methylidene}-5-nitro-2-indolinone,
(201) 3-{(Z)-1-[(1,2,3,4-tetrahydro-isoquinolin-6-yl)amino]-1-(4-(2-acetylamino-ethyl)-phenyl)-methylidene}-5-nitro-2-indolinone,
(202) 3-{(Z)-1-[(2-acetyl-1,2,3,4-tetrahydro-isoquinolin-6-yl)amino]-1-(4-(2-acetylamino-ethyl)-phenyl)-methylidene}-5-nitro-2-indolinone,
(203) 3-{(Z)-1-[4-((2,4-dioxo-imidazolidin-5-ylidene)methyl)anilino]-1-(4-(2-acetylamino-ethyl)-phenyl)-methylidene}-5-nitro-2-indolinone,
(204) 3-{(Z)-1-[4-((pyrrolidin-1-yl)methyl)anilino]-1-(4-(2-acetylamino-ethyl)-phenyl)-methylidene}-5-nitro-2-indolinone,
(205) 3-{(Z)-1-[4-(2-(imidazol-4-yl)-(E)-ethenyl)anilino]-1-(4-(2-acetylamino-ethyl)-phenyl)-methylidene}-5-nitro-2-indolinone,
(206) 3-{(Z)-1-[4-((1-methyl-2,4-dioxo-imidazolidin-5-(E/Z)-ylidene)methyl)anilino]-1-(4-(2-acetylamino-ethyl)-phenyl)-methylidene}-5-nitro-2-indolinone, (207) 3-{(Z)-1-[4-(2-ethyl-1H-imidazol-4-yl)anilino]-1-(4-(2-acetylamino-ethyl)-phenyl)-methylidene}-5-nitro-2-indolinone,
(208) 3-{(Z)-1-[4-(1-methyl-1H-imidazol-2-yl)anilino]-1-(4-(2-pyrrolidino-ethyl)-phenyl)-methylidene}-5-nitro-2-indolinone,
(209) 3-{(Z)-1-[4-(1-methyl-1H-imidazol-4-yl)anilino]-1-(4-(2-pyrrolidino-ethyl)-phenyl)-methylidene}-5-nitro-2-indolinone,
(210) 3-{(Z)-1-[4-(1H-imidazol-4-yl)anilino]-1-(4-(2-pyrrolidino-ethyl)-phenyl)-methylidene}-2-indolinone,
(211) 3-{(Z)-1-[4-(1H-imidazol-4-yl)anilino]-1-(4-(2-pyrrolidino-ethyl)-methylidene}-5-nitro-2-indolinone,
(212) 3-{(Z)-1-[4-(2-piperidino-1H-imidazol-4-yl)anilino]-1-(4-(2-pyrrolidino-ethyl)-phenyl)-methylidene}-5-nitro-2-indolinone,
(213) 3-{(Z)-1-[4-(2-methyl-1H-imidazol-4-yl)anilino]-1-(4-(2-pyrrolidino-ethyl)-phenyl)-methylidene}-5-nitro-2-indolinone,
(214) 3-{(Z)-1-[(1,2,3,4-tetrahydro-isoquinolin-6-yl)amino]-1-(4-(2-pyrrolidino-ethyl)-phenyl)-methylidene}-5-nitro-2-indolinone,
(215) 3-{(Z)-1-[(2-acetyl-1,2,3,4-tetrahydro-isoquinolin-6-yl)amino]-1-(4-(2-pyrrolidino-ethyl)-phenyl)-methylidene}-5-nitro-2-indolinone,
(216) 3-{(Z)-1-[4-((2,4-dioxo-imidazolidin-5-ylidene)methyl)anilino]-1(4-(2-pyrrolidino-ethyl)-phenyl)-methylidene}-5-nitro-2-indolinone,
(217) 3-{(Z)-1-[4-((pyrrolidin-1-yl)methyl)anilino]-1-(4-(2-pyrrolidino-ethyl)-phenyl)-methylidene}-5-nitro-2-indolinone,
(218) 3-{(Z)-1-[4-(2-(imidazol-4-yl)-(E)-ethenyl)anilino]-1-(4-(2-pyrrolidino-ethyl)-phenyl)-methylidene}-5-nitro-2-indolinone,
(219) 3-{(Z)-1-[4-((1-methyl-2,4-dioxo-imidazolidin-5-(E/Z)-ylidene)methyl)anilino]-1-(4-(2-pyrrolidino-ethyl)-phenyl)-methylidene}-5-nitro-2-indolinone,
(220) 3-{(Z)-1-[4-(2-ethyl-1H-imidazol-4-yl)anilino]-1-(4-(2-pyrrolidino-ethyl)-phenyl)-methylidene}-5-nitro-2-indolinone,
(221) 3-{(Z)-1-[4-(1-methyl-1H-imidazol-2-yl)anilino]-1-(4-(2-piperidino-ethyl)-phenyl)-methylidene}-5-nitro-2-indolinone,
(222) 3-{(Z)-1-[4-(1-methyl-1H-imidazol-4-yl)anilino]-1-(4-(2-piperidino-ethyl)-methylidene}-5-nitro-2-indolinone,
(223) 3-{(Z)-1-[4-(1H-imidazol-4-yl)anilino]-1-(4-(2-piperidino-ethyl)-phenyl)-methylidene}-2-indolinone,
(224) 3-{(Z)-1-[4-(1H-imidazol-4-yl)anilino]-1-(4-(2-piperidino-ethyl)-phenyl)-methylidene}-5-nitro-2-indolinone,
(225) 3-{(Z)-1-[4-(2-acetylamino-1H-imidazol-4-yl)anilino]-1-(4-(2-piperidino-ethyl)-phenyl)-methylidene}-5-nitro-2-indolinone,
(226) 3-{(Z)-1-[4-(2-methyl-1H-imidazol-4-yl)anilino]-1-(4-(2-piperidino-ethyl)-phenyl)-methylidene}-5-nitro-2-indolinone,
(227) 3-{(Z)-1-[(1,2,3,4-tetrahydro-isoquinolin-6-yl)amino]-1-(4-(2-piperidino-ethyl)-phenyl)-methylidene}-5-nitro-2-indolinone,
(228) 3-{(Z)-1-[(2-acetyl-1,2,3,4-tetrahydro-isoquinolin-6-yl)amino]-1-(4-(2-piperidino-ethyl)-phenyl)-methylidene}-5-nitro-2-indolinone,
(229) 3-{(Z)-1-[4-((2,4-dioxo-imidazolidin-5-ylidene)methyl)anilino]-1-(4-(2-piperidino-ethyl)-phenyl)-methylidene}-5-nitro-2-indolinone,
(230) 3-{(Z)-1-[4-((pyrrolidin-1-yl)methyl)anilino]-1-(4-(2-piperidino-ethyl)-phenyl)-methylidene}-5-nitro-2-indolinone,
(231) 3-{(Z)-1-[4-(2-(imidazol-4-yl)-(E)-ethenyl)anilino]-1-(4-(2-piperidino-ethyl)-methylidene}-5-nitro-2-indolinone,
(232) 3-{(Z)-1-[4-((1-methyl-2,4-dioxo-imidazolidin-5-(E/Z)-ylidene)methy)anilino]-1-(4-(2-piperidino-ethyl)-phenyl)-methylidene}-5-nitro-2-indolinone,
(233) 3-{(Z)-1-[4-(2-ethyl-1H-imidazol-4-yl)anilino]-1-(4-(2-piperidino-ethyl)-phenyl)-methylidene}-5-nitro-2-indolinone,
(234) 3-{(Z)-1-[4-(1-methyl-1H-imidazol-2-yl)anilino]-1-(4-(2-(2-oxo-pyrrolidino)ethyl)-phenyl)-methylidene}-5-nitro-2-indolinone,
(235) 3-{(Z)-1-[4-(1-methyl-1H-imidazol-4-yl)anilino]-1-(4-(2-(2-oxo-pyrrolidino)-ethyl)-phenyl)-methylidene}-5-nitro-2-indolinone,
(236) 3-{(Z)-1-[4-(1H-imidazol-4-yl)anilino]-1-(4-(2-(2-oxo-pyrrolidino)-ethyl)-phenyl)-methylidene}-2-indolinone,
(237) 3-{(Z)-1-[4-(1H-imidazol-4-yl)anilino]-1-(4-(2-(2-oxo-pyrrolidino)-ethyl)-phenyl)-methylidene}-5-nitro-2-indolinone,
(238) 3-{(Z)-1-[4-(2-acetylamino-1H-imidazol-4-yl)anilino]-1-(4-(2-(2-oxo-pyrrolidino)-ethyl)-phenyl)-methylidene}-5-nitro-2-indolinone,
(239) 3-{(Z)-1-[4-(2-methyl-1H-imidazol-4-yl)anilino]-1-(4-(2-(2-oxo-pyrrolidino)-ethyl)-phenyl)-methylidene}-5-nitro-2-indolinone,
(240) 3-{(Z)-1-[(1,2,3,4-tetrahydro-isoquinolin-6-yl)amino]-1-(4-(2-(2-oxo-pyrrolidino)-ethyl)-phenyl)-methylidene}-5-nitro-2-indolinone,
(241) 3-{(Z)-1-[(2-acetyl-1,2,3,4-tetrahydro-isoquinolin-6-yl)amino]-1-(4-(2-(2-oxo-pyrrolidino)-ethyl)-phenyl)-methylidene}-5-nitro-2-indolinone,
(242) 3-{(Z)-1-[4-((2,4-dioxo-imidazolidin-5-ylidene)methyl)anilino]-1-(4-(2-(2-oxo-pyrrolidino)-ethyl)-phenyl)-methylidene}-5-nitro-2-indolinone,
(243) 3-{(Z)-1-[4-((pyrrolidin-1-yl)methyl)anilino]-1-(4-(2-(2-oxo-pyrrolidino)-ethyl)-phenyl)-methylidene}-5-nitro-2-indolinone,
(244) 3-{(Z)-1-[4-(2-(imidazol-4-yl)-(E)-ethenyl)anilino]-1-(4-(2-(2-oxo-pyrrolidino)-ethyl)-phenyl)-methylidene}-5-nitro-2-indolinone,
(245) 3-{(Z)-1-[4-((1-methyl-2,4-dioxo-imidazolidin-5-(E/Z)-ylidene)methyl)anilino]-1-(4-(2-(2-oxo-pyrrolidino)-ethyl)-phenyl)-methylidene}-5-nitro-2-indolinone,
(246) 3-{(Z)-1-[4-(2-ethyl-1H-imidazol-4-yl)anilino]-1-(4-(2-(2-oxo-pyrrolidino)-ethyl)-phenyl)-methylidene}-5-nitro-2-indolinone,
(247) 3-{(Z)-1-[4-(1-methyl-1H-imidazol-2-yl)anilino-1-(4-(2-(2-oxo-piperidino)-ethyl)-phenyl)-methylidene}-5-nitro-2-indolinone,
(248) 3-{(Z)-1-[4-(1-methyl-1H-imidazol-4-yl)anilino]-1-(4-(2-(2-oxo-piperidino)-ethyl)-phenyl)-methylidene}-5-nitro-2-indolinone,
(249) 3-{(Z)-1-[4-(1H-imidazol-4-yl)anilino]-1-(4-(2-(2-oxo-piperidino)-ethyl)-phenyl)-methylidene}-2-indolinone,
(250) 3-{(Z)-1-[4-(1H-imidazol-4-yl)anilino]-1-(4-(2-(2-oxo-piperidino)-ethyl)-phenyl)-methylidene}-5-nitro-2-indolinone,
(251) 3-{(Z)-1-[4-(2-acetylamino-1H-imidazol-4-yl)anilino]-1-(4-(2-(2-oxo-piperidino)-ethyl)-phenyl)-methylidene}-5-nitro-2-indolinone,
(252) 3-{(Z)-1-[4-(2-methyl-1H-imidazol-4-yl)anilino]-1-(4-(2-(2-oxo-piperidino)-ethyl)-phenyl)-methylidene}-5-nitro-2-indolinone,
(253) 3-{(Z)-1-[(1,2,3,4-tetrahydro-isoquinolin-6-yl)amino]-1-(4-(2-(2-oxo-piperidino)-ethyl)-phenyl)-methylidene}-5-nitro-2-indolinone, (254) 3-{(Z)-1-[(2-acetyl-1,2,3,4-tetrahydro-isoquinolin-6-yl)amino]-1-(4-(2-(2-oxo-piperidino)-ethyl)-phenyl)-methylidene}-5-nitro-2-indolinone, (255) 3-{(Z)-1-[4-((2,4-dioxo-imidazolidin-5-ylidene)methyl)anilino]-1-(4-(2-(2-oxo-piperidino)-ethyl)-phenyl)-methylidene}-5-nitro-2-indolinone, (256) 3-{(Z)-1-[4-((pyrrolidin-1-yl)methyl)anilino]-1-(4-(2-(2-oxo-piperidino)-ethyl)-phenyl)-methylidene}-5-nitro-2-indolinone, (257) 3-{(Z)-1-[4-(2-(imidazol-4-yl)-(E)-ethenyl)anilino]-1-(4-(2-(2-oxo-piperidino)-ethyl)-phenyl)-methylidene}-5-nitro-2-indolinone, (258) 3-{(Z)-1-[4-((1-methyl-2,4-dioxo-imidazolidin-5-(E/Z)-ylidene)methyl)anilino]-1-(4-(2-(2-oxo-piperidino)-ethyl)-phenyl)-methylidene}-5-nitro-2-indolinone, (259) 3-{(Z)-1-[4-(2-ethyl-1H-imidazol-4-yl)anilino]-1-(4-(2-(2-oxo-pipridino)-ethyl)-phenyl)-methylidene}-5-nitro-2-indolinone, (260) 3-{(Z)-1-[4-(1-methyl-1H-imidazol-2-yl)anilino]-1-(4-(3-amino-propyl)-phenyl)-methylidene}-5-nitro-2-indolinone, (261) 3-{(Z)-1-[4-(1-methyl-1H-imidazol-4-yl)anilino]-1-(4-(3-amino-propyl)-phenyl)-methylidene}-5-nitro-2-indolinone, (262) 3-{(Z)-1-[4-(1H-imidazol-4-yl)anilino]-1-(4-(3-amino-propyl)-phenyl)-methylidene}-2-indolinone, (263) 3-{(Z)-1-[4-(1H-imidazol-4-yl)anilino]-1-(4-(3-amino-propyl)-phenyl)-methylidene}-5-nitro-2-indolinone, (264) 3-{(Z)-1-[4-(2-piperidino-1H-imidazol-4-yl)anilino]-1-(4-(3-amino-propyl)-phenyl)-methylidene}-5-nitro-2-indolinone, (265) 3-{(Z)-1-[4-(2-methyl-1H-imidazol-4-yl)anilino]-1-(4-(3-amino-propyl)-phenyl)-methylidene}-5-nitro-2-indolinone, (266) 3-{(Z)-1-[(1,2,3,4-tetrahydro-isoquinolin-6-yl)amino]-1-(4-(3-amino-propyl)-phenyl)-methylidene}-5-nitro-2-indolinone, (267) 3-{(Z)-1-[(2-acetyl-1,2,3,4-tetrahydro-isoquinolin-6-yl)amino]-1-(4-(3-amino-propyl)-phenyl)-methylidene}-5-nitro-2-indolinone, (268) 3-{(Z)-1-[4-((2,4-dioxo-imidazolidin-5-ylidene)methyl)anilino]-1-(4-(3-amino-propyl)-phenyl)-methylidene}-5-nitro-2-indolinone, (269) 3-{(Z)-1-[4-((pyrrolidin-1-yl)methyl)anilino]-1-(4-(3-amino-propyl)-phenyl)-methylidene}-5-nitro-2-indolinone, (270) 3-{(Z)-1-[4-(2-(imidazol-4-yl)-(E)-ethenyl)anilino]-1-(4-(3-amino-propyl)-phenyl)-methylidene}-5-nitro-2-indolinone, (271) 3-{(Z)-1-[4-((1-methyl-2,4-dioxo-imidazolidin-5-(E/Z)-ylidene)methyl)anilino]-1-(4-(3-amino-propyl)-phenyl)-methylidene}-5-nitro-2-indolinone, (272) 3-{(Z)-1-[4-(2-ethyl-1H-imidazol-4-yl)anilino]-1-(4-(3-amino-propyl)-phenyl)-methylidene}-5-nitro-2-indolinone, (273) 3-{(Z)-1-[4-(1-methyl-1H-imidazol-2-yl)anilino]-1-(4-(3-acetylamino-propyl)-phenyl)-methylidene}-5-nitro-2-indolinone, (274) 3-{(Z)-1-[4-(1-methyl-1H-imidazol-4-yl)anilino-]1-(4-(3-acetylamino-propyl)-phenyl)-methylidene}-5-nitro-2-indolinone, (275) 3-{(Z)-1-[4-(1H-imidazol-4-yl)anilino]-1-(4-(3-acetylamino-propyl)-phenyl)-methylidene}-2-indolinone, (276) 3-{(Z)-1-[4-(1H-imidazol-4-yl)anilino]-1-(4-(3-acetylamino-propyl)-phenyl)-methylidene}-5-nitro-2-indolinone, (277) 3-{(Z)-1-[4-(2-piperidino-1H-imidazol-4-yl)anilino]-1-(4-(3-acetylamino-propyl)-phenyl)-methylidene}-5-nitro-2-indolinone, (278) 3-{(Z)-1-[4-(2-methyl-1H-imidazol-4-yl)anilino]-1-(4-(3-acetylamino-propyl)-phenyl)-methylidene}-5-nitro-2-indolinone, (279) 3-{(Z)-1-[(1,2,3,4-tetrahydro-isoquinolin-6-yl)amino]-1-(4-(3-acetylamino-propyl)-phenyl)-methylidene}-5-nitro-2-indolinone, (280) 3-{(Z)-1-[(2-acetyl-1,2,3,4-tetrahydro-isoquinolin-6-yl)amino]-1-(4-(3-acetylamino-propyl)-phenyl)-methylidene}-5-nitro-2-indolinone, (281) 3-{(Z)-1-[4-((2,4-dioxo-imidazolidin-5-ylidene)methyl)anilino]-1-(4-(3-acetylamino-propyl)-phenyl)-methylidene}-5-nitro-2-indolinone, (282) 3-{(Z)-1-[4-((pyrrolidin-1-yl)methyl)anilino]-1-(4-(3-acetylamino-propyl)-phenyl)-methylidene}-5-nitro-2-indolinone, (283) 3-{(Z)-1-[4-(2-(imidazol-4-yl)-(E)-ethenyl)anilino]-1-(4-(3-acetylamino-propyl)-phenyl)-methylidene}-5-nitro-2-indolinone, (284) 3-{(Z)-1-[4-((-methyl-2,4-dioxo-imidazolidin-5-(E/Z)-ylidene)methyl)anilino]-1-(4-(3-acetylamino-propyl)-phenyl)-methylidene-}5-nitro-2-indolinone, (285) 3-{(Z)-1-[4-(2-ethyl-1H-imidazol-4-yl)anilino]-1-(4-(3-acetylamino-propyl)-phenyl)-methylidene}-5-nitro-2-indolinone, (286) 3-{(Z)-1-[4-(1-methyl-1H-imidazol-2-yl)anilino]-1-(4-(3-pyrrolidino-propyl)-phenyl)-methylidene}-5-nitro-2-indolinone, (287) 3-{(Z)-1-[4-(1-methyl-1H-imidazol-4-yl)anilino]-1-(4-(3-pyrrolidino)-propyl)-phenyl)-methylidene}-5-nitro-2-indolinone, (288) 3-{(Z)-1-[4-(1H-imidazol-4-yl)anilino]-1-(4-(3-pyrrolidino-propyl)-phenyl)-methylidene}-2-indolinone, (289) 3-{(Z)-1-[4-(1H-imidazol-4-yl)anilino]-1-(4-(-pyrrolidino-propyl)-phenyl)-methylidene}-5-nitro-2-indolinone, (290) 3-{(Z)-1-[4-(2-piperidino-1H-imidazol-4-yl)anilino]-1-(4-(3-pyrrolidino-propyl)-phenyl)-methylidene}-5-nitro-2-indolinone, (291) 3-{(Z)-1-[4-(2-methyl-1H-imidazol-4-yl)anilino]-1-(4-(3-pyrrolidino-propyl)-phenyl)-methylidene}-5-nitro-2-indolinone, (292) 3-{(Z)-1-[(1,2,3,4-tetrahydro-isoquinolin-6-yl)amino]-1-(4-(3-pyrrolidino-propyl)-phenyl)-methylidene}-5-nitro-2-indolinone, (293) 3-{(Z)-1-[(2-acetyl-1,2,3,4-tetrahydro-isoquinolin-6-yl)amino]-1-(4-(3-pyrrolidino-propyl)-phenyl)-methylidene}-5-nitro-2-indolinone, (294) 3-{(Z)-1-4-((2,4-dioxo-imidazolidin-5-ylidene)methyl)anilino]-1-(4-(3-pyrrolidino-propyl)-phenyl)-methylidene}-5-nitro-2-indolinone, (295) 3-{(Z)-1-[4-((pyrrolidin-1-yl)methyl)anilino]-1-(4-(3-pyrrolidino-propyl)-phenyl)-methylidene}-5-nitro-2-indolinone, (296) 3-{(Z)-1-[4-(2-(imidazol-4-yl)-(E)-ethenyl)anilino]-1-(4-(3-pyrrolidino-propyl)-phenyl)-methylidene}-5-nitro-2-indolinone, (297) 3-{(Z)-1-[4-((-methyl-2,4-dioxo-imidazolidin-5-(E/Z)-ylidene)methyl)anilino]-1-(4-(3-pyrrolidino-propyl)-phenyl)-methylidene}-5-nitro-2-indolinone, (298) 3-{(Z)-1-[4-(2-ethyl-1H-imidazol-4-yl)anilino]-1-(4-(3-pyrrolidino-propyl)-phenyl)-methylidene}-5-nitro-2-indolinone, (299) 3-{(Z)-1-[4-(1-methyl-1H-imidazol-2-yl)anilino]-1-(4-(3-piperidino-propyl)-phenyl)-methylidene}-5-nitro-2-indolinone, (300) 3-{(Z)-1-[4-(1-methyl-1H-imidazol-4-yl)anilino]-1-(4-(3-piperidino-propyl)-phenyl)-methylidene}-5-nitro-2-indolinone,
(301) 3-{(Z)-1-[4-(1H-imidazol-4-yl)anilino]-1-(4-(3-piperidino-propyl)-phenyl)-methylidene}-2-indolinone,
(302) 3-{(Z)-1-[4-(1H-imidazol-4-yl)anilino]-1-(4-(3-piperidino-propyl)-phenyl)-methylidene}-5-nitro-2-indolinone,
(303) 3-{(Z)-1-[4-(2-acetylamino-1H-imidazol-4-yl)anilino]-1-(4-(3-piperidino-propyl)-phenyl)-methylidene}-5-nitro-2-indolinone,
(304) 3-{(Z)-1-[4-(2-methyl-1H-imidazol-4-yl)anilino]-1-(4-(3-piperidino-propyl)-phenyl)-methylidene}-5-nitro-2-indolinone,
(305) 3-{(Z)-1-[(1,2,3,4-tetrahydro-isoquinolin-6-yl)amino]-1-(4-(3-piperidino-propyl)-phenyl)-methylidene}-5-nitro-2-indolinone,
(306) 3-{(Z)-1-[(2-acetyl-1,2,3,4-tetrahydro-isoquinolin-6-yl)-amino]-1-(4-(3-piperidino)-propyl)-phenyl)-methylidene}-5-nitro-2-indolinone,
(307) 3-{(Z)-1-[4-((2,4-dioxo-imidazolidin-5-ylidene)methyl)anilino]-1-(4-(3-piperidino-propyl)-phenyl)-methylidene}-5-nitro-2-indolinone,
(308) 3-{(Z)-1-[4-((pyrrolidin-1-yl)methyl)anilino]-1-(4-(3-piperidino-propyl)-phenyl)-methylidene}-5-nitro-2-indolinone,
(309) 3-{(Z)-1-[4-(2-(imidazol4-yl)-(E)-ethenyl)anilino]-1-(4-(3-piperidino-propyl)-phenyl)-methylidene}-5-nitro-2-indolinone,
(310) 3-{(Z)-1-[4-((1-methyl-2,4-dioxo-imidazolidin-5-(E/Z)-ylidene)methy)anilino]-1-(4-(3-piperidino-propyl)-phenyl)-methylidene}-5-nitro-2-indolinone,
(311) 3-{(Z)-1-[4-(2-ethyl-1H-imidazol-4-yl)anilino]-1-(4-(3-piperidino-propyl)-phenyl)-methylidene}-5-nitro-2-indolinone,
(312) 3-{(Z)-1-[4-(1-methyl-1H-imidazol-2-yl)anilino]-1-(4-(3-(2-oxo-pyrrolidino)-propyl)-phenyl)-methylidene}-5-nitro-2-indolinone,
(313) 3-{(Z)-1-[4-(1-methyl-1H-imidazol-4-yl)anilino]-1-(4-(3-(2-oxo-pyrrolidino)-propyl)-phenyl)-methylidene}-5-nitro-2-indolinone,
(314) 3-{(Z)-1-[4-(1H-imidazol-4-yl)anilino]-1-(4-(3-(2-oxo-pyrrolidino)-propyl)-phenyl)-methylidene}-2-indolinone,
(315) 3-{(Z)-1-[4-(1H-imidazol-4-yl)anilino]-1-(4-(3-(2-oxo-pyrrolidino)-propyl)-phenyl)-methylidene}-5-nitro-2-indolinone,
(316) 3-{(Z)-1-[4-(2-acetylamino-1H-imidazol-4-yl)anilino]-1-(4-(3-(2-oxo-pyrrolidino)-propyl)-phenyl)-methylidene}-5-nitro-2-indolinone,
(317) 3-{(Z)-1-[4-(2-methyl-1H-imidazol-4-yl)anilino]-1-(4-(3-(2-oxo-pyrrilidino)-propyl)-phenyl)-methylidene}-5-nitro-2-indolinone,
(318) 3-{(Z)-1-[(1,2,3,4-tetrahydro-isoquinolin-6-yl)amino]-1-(4-(3-(2-oxo-pyrrolidino)-propyl)-phenyl)-methylidene}-5-nitro-2-indolinone,
(319) 3-{(Z)-1-[(2-acetyl-1,2,3,4-tetrahydro-isoquinolin-6-yl)amino]-1-(4-(3-(2-oxo-pyrrolidino)-propyl)-phenyl)-methylidene}-5-nitro-2-indolinone,
(320) 3-{(Z)-1-[4-((2,4-dioxo-imidazolidin-5-ylidene)methyl)anilino]1-(4-(3-(2-oxo-pyrrolidino)-propyl)-phenyl)-methylidene}-5-nitro-2-indolinone,
(321) 3-{(Z)-1-[4-((pyrrolidin-1-yl)methyl)anilino]-1-(4-(3-(2-oxo-pyrrolidino)-propyl)-phenyl)-methylidene}-5-nitro-2-indolinone,
(322) 3-{(Z)-1-[4-(2-(imidazol-4-yl)-(E)-ethenyl)anilino]-1-(4-(3-(2-oxo-pyrrolidino)-propyl)-phenyl)-methylidene}-5-nitro-2-indolinone,
(323) 3-{(Z)-1-[4-((1-methyl-2,4-dioxo-imidazolidin-5-(E/Z)-ylidene)methyl)anilino]-1-(4-(3-(2-oxo-pyrrolidino)-propyl)-phenyl)-methylidene}-5-nitro-2-indolinone,
(324) 3-{(Z)-1-[4-(2-ethyl-1H-imidazol-4-yl)anilino]-1-(4-(3-(2-oxo-pyrrolidino)-propyl)-phenyl)-methylidene}-5-nitro-2-indolinone,
(325) 3-{(Z)-1-[4-(1-methyl-1H-imidazol-2-yl)anilino]-1-(4-(3-(2-oxo-piperidino)-propyl)-phenyl)-methylidene}-5-nitro-2-indolinone,
(326) 3-{(Z)-1-[4-(1-methyl-1H-imidazol-4-yl)anilino]-1-(4-(3-(2-oxo-piperidino)-propyl)-phenyl)-methylidene}-5-nitro-2-indolinone,
(327) 3-{(Z)-1-[4-(1H-imidazol-4-yl)anilino]-1-(4-(3-(2-oxo-piperidino)-propyl)-phenyl)-methylidene}-2-indolinone,
(328) 3-{(Z)-1-[4-(1H-imidazol-4-yl)anilino]-1-(4-(3-(2-oxo-piperidino)-propyl)-phenyl)-methylidene}-5-nitro-2-indolinone,
(329) 3-{(Z)-1-[4-(2-acetylamino-1H-imidazol-4-yl)anilino]-1-(4-(3-(2-oxo-piperidino)-propyl)-phenyl)-methylidene}-5-nitro-2-indolinone,
(330) 3-{(Z)-1-[4-(2-methyl-1H-imidazol-4-yl)anilino]-1-(4-(3-(2-oxo-piperidino)-propyl)-phenyl)-methylidene}-5-nitro-2-indolinone,
(331) 3-{(Z)-1-[(1,2,3,4-tetrahydro-isoquinolin-6-yl)amino]-1-(4-(3-(2-oxo-piperidino)-propyl)-phenyl)-methylidene}-5-nitro-2-indolinone,
(332) 3-{(Z)-1-(2-acetyl-1,2,3,4-tetrahydro-isoquinolin-6-yl)amino]-1-(4-(3-(2-oxo-piperidino)-propyl)-phenyl)-methylidene}5-nitro-2-indolinone,
(333) 3-{(Z)-1-[4-((2,4-dioxo-imidazoldin-5-ylidene)methyl)anilino]-1-(4-(3-(2-oxo-piperidino)-propyl)-phenyl)-methylidene}-5-nitro-2-indolinone,
(334) 3-{(Z)-1-[4-((pyrrolidin-1-yl)methyl)anilino]-1-(4-(3-(2-oxo-piperidino)-propyl)-phenyl)-methylidene}-5-nitro-2-indolinone,
(335) 3-{(Z)-1-[4-(2-(imidazol-4-yl)-(E)-ethenyl)anilino]-1-(4-(3-(2-oxo-piperidino)-propyl)-phenyl)-methylidene}-5-nitro-2-indolinone,
(336) 3-{(Z)-1-[4-((1-methyl-2,4-dioxo-imidazolidin-5-(E/Z)-yldene)methyl)anilino]-1-(4-(3-(2-oxo-piperidino)-propyl)-phenyl)-methylidene}-5-nitro-2-indolinone,
(337) 3-{(Z)-1-[4-(2-ethyl-1H-imidazol-4-yl)anilino]-1-(4-(3-(2-oxo-piperidino)-propyl)-phenyl)-methylidene}-5-nitro-2-indolinone,
(338) 3-{(Z)-1-[4-(1-methyl-1H-imidazol-2-yl)anilino]-1-(4-((3-amino-1-propen-1-yl)phenyl)-methylidene}-5-nitro-2-indolinone,
(339) 3-{(Z)-1-[4-(1-methyl-1H-imidazol-4-yl)anilino]-1-(4-((3-amino-1-propen-1-yl)phenyl)-methylidene}-5-nitro-2-indolinone,
(340) 3-{(Z)-1-[4-(1H-imidazol-4-yl)anilino]-1-(4-((3-amino-1-propen-1-yl)phenyl)-methylidene}-2-indolinone,
(341) 3-{(Z)-1-[4-(1H-imidazol-4-yl)anilino]-1-(4-((3-amino-1-propen-1-methylidene}-5-nitro-2-indolinone,
(342) 3-{(Z)-1-[4-(2-piperidino-1H-imidazol-4-yl)anilino]-1-(4-((3-amino-1-yl)phenyl)-methylidene}-5-nitro-2-indolinone,
(343) 3-{(Z)-1-[4-(2-methyl-1H-imidazol-4-yl)anilino]-1-(4-((3-amino-1-propen-1-yl)phenyl)-methylidene}-5-nitro-2-indolinone,
(344) 3-{(Z)-1-[(1,2,3,4-tetrahydro-isoquinolin-6-yl)amino]-1-(4-((3-amino-1-propen-1-yl)phenyl)-methylidene}-5-nitro-2-indolinone,
(345) 3-{(Z)-1-[(2-acetyl-1,2,3,4-tetrahydro-isoquinolin-6-yl)amino]-1-(4-((3-amino-1-propen-1-yl)phenyl)-methylidene}-5-nitro-2-indolinone, (346) 3-{(Z)-1-[4-((2,4-dioxo-imidazolidin-5-ylidene) methyl)anilino]-1-(4-((3-amino-1-propen-1-yl)phenyl)-methylidene}-5-nitro-2-indolinone,
(347) 3-{(Z)-1-[4-((pyrrolidin-1-yl)methyl)anilino]-1-(4-((3-amino-1-propen-1-yl)phenyl)-methylidene}-5-nitro-2-indolinone,
(348) 3-{(Z)-1-[4-(2-(imidazol-4-yl)-(E)-ethenyl)anilino]-1-(4-((3-amino-1-propen-1-yl)phenyl)-methylidene}-5-nitro-2-indolinone,
(349) 3-{(Z)-1-[4-((-methyl-2,4-dioxo-imidazolidin-5-(E/Z)-ylidene)methyl)anilino]-1-(4-((3-amino-1-propen-1-yl)phenyl)-methylidene}-5-nitro-2-indolinone,
(350) 3-{(Z)-1-[4-(2-ethyl-1H-imidazol-4-yl)anilino]-1-(4-((3-amino-1-propen-1-yl)phenyl)-methylidene}-5-nitro-2-indolinone,
(351) 3-{(Z)-1-[4-(1-methyl-1H-imidazol-2-yl)anilino]-1-(4-((3-acetylamino-1-propen-1-yl)phenyl)-methylidene}-5-nitro-2-indolinone,
(352) 3-{(Z)-1-[4-(1-methyl-1H-imidazol-4-yl)anilino]-1-(4-((3-acetylamino-1-propen-1-yl)phenyl)-methylidene}-5-nitro-2-indolinone,
(353) 3-{(Z)-1-[4-(1H-imidazol-4-yl)anilino]-1-(4-((3-acetylamino-1-propen-1-yl)-phenyl)-methylidene}-2-indolinone,
(354) 3-{(Z)-1-[4-(1H-imidazol-4-yl)anilino]-1-(4-((3-acetylamino-1-propen-1-yl)-phenyl)-methylidene}-5-nitro-2-indolinone,
(355) 3-{(Z)-1-[4-(2-piperidino-1H-imidazol-4-yl)anilino]-1-(4-((3-acetylamino-1-propen-1-yl)phenyl)-methylidene}-5-nitro-2-indolinone,
(356) 3-{(Z)-1-[4-(2-methyl-1H-imidazol-4-yl)anilino]-1-(4-((3-acetylamino-1--propen-1-yl)phenyl)-methylidene}-5-nitro-2-indolinone,
(357) 3-{(Z)-1-[(1,2,3,4-tetrahydro-isoquinolin-6-yl)amino]-1-(4-((3-acetylamino-1-propen-1-yl)phenyl)-methylidene}-5-nitro-2-indolinone,
(358) 3-{(Z)-1-[(2-acetyl-1,2,3,4-tetrahydro-isoquinolin-6-yl)amino]-1-(4-((3-acetylamino-1-propen-1-yl)phenyl)-methylidene}-5-nitro-2-indolinone,
(359) 3-{(Z)-1-[4-((2,4-di oxo-imidazolidin-5-ylidene) methyl)anilino]-1-(4-((3-acetylamino-1-propen-1-yl) phenyl)-methylidene}-5-nitro-2-indolinone,
(360) 3-{(Z)-1-[4-((pyrrolidin-1-yl)methyl)anilino]-1-(4-((3-acetylamino-1-propen-1-yl)phenyl)-methylidene}-5-nitro-2-indolinone,
(361) 3-{(Z)-1-[4-(2-(imidazol-4-yl)-(E)-ethenyl)anilino]-1-(4-((3-acetylamino-1-propen-1-yl)phenyl)-methylidene}-5-nitro-2-indolinone,
(362) 3-{(Z)-1-[4-((1-methyl-2,4-dioxo-imidazolidin-5-(E/Z)-ylidene)methyl)anilino]-1-(4-((3-acetylamino-1-propen-1-yl)phenyl)-methylidene}-5-nitro-2-indolinone,
(363) 3-{(Z)-1-[4-(2-ethyl-1H-imidazol-4-yl)anilino]-1-(4-((3-acetylamino-1-propin-1-yl)phenyl)-methylidene}-5-nitro-2-indolinone,
(364) 3-{(Z)-1-[4-(1-methyl-1H-imidazol-2-yl)anilino]-1-(4-((3-pyrrolidino-1-propen-1-yl)phenyl)-methylidene}-5-nitro-2-indolinone,
(365) 3-{(Z)-1-[4-(1-methyl-1H-imidazol-4-yl)anilino]-1-(4-((3-pyrrolidino-1-propen-1-yl)phenyl)-methylidene}-5-nitro-2-indolinone,
(366) 3-{(Z)-1-[4-(1H-imidazol-4-yl)anilino]-1-(4-((3-pyrrolidino-1-propen-1-yl)phenyl)-methylidene}-2-indolinone,
(367) 3-{(Z)-1-[4-(1H-imidazol-4-yl)anilino]-1-(4-((3-pyrrolidino-1-propen-1-yl)-phenyl)-methylidene}-5-nitro-2-indolinone,
(368) 3-{(Z)-1-[4-(2-piperidino-1H-imidazol-4-yl)anilino]-1-(4-((3-pyrrolidino-1-propen-1-yl)phenyl)-methylidene}-5-nitro-2-indolinone,
(369) 3-{(Z)-1-[4-(2-methyl-1H-imidazol-4-yl)anilino]-1-(4-((3-pyrrolidino-1-propen-1-yl)phenyl)-methylidene}-5-nitro-2-indolinone,
(370) 3-{(Z)-1-[(1,2,3,4-tetrahydro-isoquinolin-6-yl)amino]-1-(4-((3-pyrrolidino-1-propen-1-yl)phenyl)-methylidene}-5-nitro-2-indolinone,
(371) 3-{(Z)-1-[(2-acetyl-1,2,3,4-tetrahydro-isoquinolin-6-yl)amino]-1-(4-((3-pyrrolidino-1-propen-1-yl)phenyl)-methylidene}-5-nitro-2-indolinone,
(372) 3-{(Z)-1-[4-((2,4-dioxo-imidazolidin-5-ylidene) methyl)anilino]-1-(4-((3-pyrrolidine-1-propen-1-yl) phenyl)-methylidene}-5-nitro-2-indolinone,
(373) 3-{(Z)-1-[4-((pyrrolidin-1-yl)methyl)anilino]-1-(4-((3-pyrrolidino-1-propen-1-yl)phenyl)-methylidene}-5-nitro-2-indolinone,
(374) 3-{(Z)-1-[4-(2-(imidazol-4-yl)-(E)-ethenyl)anilino]-1-(4-((3-pyrrolidino-1-propen-1-yl)phenyl)-methylidene}-5-nitro-2-indolinone,
(375) 3-{(Z)-1-[4-((-methyl-2,4-dioxo-imidazolidin-5-(E/Z)-ylidene)methyl)anilino]-1-(4-((3-pyrrolidino-1-propen-1-yl)phenyl)-methylidene}-5-nitro-2-indolinone,
(376) 3-{(Z)-1-[4-(2-ethyl-1H-imidazol-4-yl)anilino]-1-(4-((3-pyrrolidino-1-propen-1-yl)phenyl)-methylidene}-5-nitro-2-indolinone,
(377) 3-{(Z)-1-[4-(1-methyl-1H-imidazol-2-yl)anilino]-1-(4-((3-piperidino-1-propen-1-yl)phenyl)-methylidene}-5-nitro-2-indolinone,
(378) 3-{(Z)-1-[4-(1-methyl-1H-imidazol-4-yl)anilino]-1-(4-((3-piperidino-1-propen-1-yl)phenyl)-methylidene}-5-nitro-2-indolinone,
(379) 3-{(Z)-1-[4-(1H-imidazol-4-yl)anilino]-1-(4-((3-piperidino-1-propen-1-yl)phenyl)-methylidene}-2-indolinone,
(380) 3-{(Z)-1-[4-(1H-imidazol-4-yl)anilino]-1-(4-((3-piperidino-1-propen-1-yl)phenyl)-methylidene}-5-nitro-2-indolinone,
(381) 3-{(Z)-1-[4-(2-acetylamino-1H-imidazol-4-yl) anilino]-1-(4-((3-piperidino-1-propen-1-yl)phenyl)-methylidene}-5-nitro-2-indolinone,
(382) 3-{(Z)-1-[4-(2-methyl-1H-imidazol-4-yl)anilino]-1-(4-((3-piperidino-1-propen-1-yl)phenyl)-methylidene}-5-nitro-2-indolinone,
(383) 3-{(Z)-1-[(1,2,3,4-tetrahydro-isoquinolin-6-yl)amino]-1-(4-((3-piperidino-1-propen-1-yl)phenyl)-methylidene}-5-nitro-2-indolinone,
(384) 3-{(Z)-1-[(2-acetyl-1,2,3,4-tetrahydro-isoquinolin-6-yl)amino]-1-(4-((3-piperidino-1-propen-1-yl)phenyl)-methylidene}-5-nitro-2-indolinone,
(385) 3-{(Z)-1-[4-((2,4-dioxo-imidazolidin-5-ylidene) methyl)anilino]-1-(4-((3-piperidino-1-propen-1-yl) phenyl)-methylidene}-5-nitro-2-indolinone,
(386) 3-{(Z)-1-[4-((pyrrolidin-1-yl)methyl)anilino]-1-(4-((3-piperidino-1-propen-1-yl)phenyl)-methylidene}-5-nitro-2-indolinone,
(387) 3-{(Z)-1-[4-(2-(imidazol-4-yl)-(E)-ethenyl)anilino]-1-(4-((3-piperidino-1-propen-1-yl)phenyl)-methylidene}-5-nitro-2-indolinone,
(388) 3-{(Z)-1-[4-((1-methyl-2,4-dioxo-imidazolidin-5-(E/Z)-ylidene)methyl)anilino]-1-(4-((3-piperidino-1-propen-1-yl)phenyl)-methylidene}-5-nitro-2-indolinone,
(389) 3-{(Z)-1-[4-(2-ethyl-1H-imidazol-4-yl)anilino]-1-(4-((3-piperidino-1-propen-1-yl)phenyl)-methylidene}-5-nitro-2-indolinone,
(390) 3-{(Z)-1-[4-(1-methyl-1H-imidazol-2-yl)anilino]-1-(4-((3-(2-oxo-pyrrolidino)-1-propen-1-yl)phenyl)-methylidene}-5-nitro-2-indolinone,
(391) 3-{(Z)-1-[4-(1-methyl-1H-imidazol-4-yl)anilino]-1-(4-((3-(2-oxo-pyrrolidino-1-propen-1-yl)phenyl)-methylidene}-5-nitro-2-indolinone, (392) 3-{(Z)-1-[4-(1H-imidazol-4-yl)anilino]-1-1-(4-((3-(2-oxo-pyrrolidino)-1-propen-1-yl)phenyl)-methylidene}-2-indolinone,
(393) 3-{(Z)-1-[4-(1H-imidazol-4-yl)anilino]-1-(4-((3-(2-oxo-pyrrolidino)-1-propen-1-yl)phenyl)-methylidene}-5-nitro-2-indolinone,
(394) 3-{(Z)-1-[4-(2-acetylamino-1H-imidazol-4-yl)anilino]-1-(4-((3-(2-oxo-pyrrolidino)-1-propen-1-yl)phenyl)-methylidene}-5-nitro-2-indolinone,
(395) 3-{(Z)-1-[4-(2-methyl-1H-imidazol-4-yl)anilino]-1-(4-((3-(2-oxo-pyrrolidino)-1-propen-1-yl)phenyl)-methylidene}-5-nitro-2-indolinone,
(396) 3-{(Z)-1-[(1,2,3,4-tetrahydro-isoquinolin-6-yl)amino]-1-(4-((3-(2-oxo-pyrrolidino)-1-propen-1-yl)phenyl)-methylidene}-5-nitro-2-indolinone,
(397) 3-{(Z)-1-[(2-acetyl-1,2,3,4-tetrahydro-isoquinolin-6-yl)-amino]-1-(4-((3-(2-oxo-pyrrolidino)-1-propen-1-yl)phenyl)-methylidene}-5-nitro-2-indolinone,
(398) 3-{(Z)-1-[4-((2,4-dioxo-imidazolidin-5-ylidene)methyl)anilino]-1-(4-((3-(2-oxo-pyrrolidino)-1-propen-1-yl)phenyl)-methylidene}-5-nitro-2-indolinone,
(399) 3-{(Z)-1-[4-((pyrrolidin-1-yl)methyl)anilino]-1-(4-((3-(2-oxo-pyrrolidino)-1-propen-1-yl)phenyl)-methylidene}-5-nitro-2-indolinone,
(400) 3-{(Z)-1-[4-(2-(imidazol-4-yl)-(E)-ethenyl)anilino]-1-(4-((3-(2-oxo-pyrrolidino)-1-propen-1-yl)phenyl)-methylidene}-5-nitro-2-indolinone,
(401) 3-{(Z)-1-[4-((1-methyl-2,4-dioxo-imidazolidin-5-(E/Z)-ylidene)methyl)anilino]-1-1-(4-((3-(2-oxo-pyrrolidino)-1-propen-1-yl)phenyl)-methylidene}-5-nitro-2-indolinone,
(402) 3-{(Z)-1-[4-(2-ethyl-1H-imidazol-4-yl)anilino]-1-(4-((3-(2-oxo-pyrrolidino)-1-propen-1-yl)-phenyl)-methylidene}-5-nitro-2-indolinone,
(403) 3-{(Z)-1-[4-(1-methyl-1H-imidazol-2-yl)anilino]-1-(4-(3-(2-oxo-piperidino)-propyl)-phenyl)-methylidene}-5-nitro-2-indolinone,
(404) 3-{(Z)-1-[4-(1-methyl-1H-imidazol-4-yl)anilino]-1-(4-((3-(2-oxo-piperidino)-1-propen-1-yl)phenyl)-methylidene}-5-nitro-2-indolinone,
(405) 3-{(Z)-1-[4-(1H-imidazol-4-yl)anilino]-1-(4-((3-(2-oxo-piperidino)-1-propen-1-yl)phenyl)-methylidene}-2-indolinone,
(406) 3-{(Z)-1-[4-(1H-imidazol-4-yl)anilino]-1-(4-((3-(2-oxo-piperidino)-1-propen-1-yl)phenyl)-methylidene}-5-nitro-2-indolinone,
(407) 3-{(Z)-1-[4-(2-acetylamino-1H-imidazol-4-yl)anilino]-1-(4-((3-(2-oxo-piperidino)-1-propen-1-yl)phenyl)-methylidene}-5-nitro-2-indolinone,
(408) 3-{(Z)-1-[4-(2-methyl-1H-imidazol-4-yl)anilino]-1-(4-((3-(2-oxo-piperidino)-1-propen-1-yl)phenyl)-methylidene}-5-nitro-2-indolinone,
(409) 3-{(Z)-1-[(1,2,3,4-tetrahydro-isoquinolin-6-yl)amino]-1-(4-((3-(2-oxo-piperidino)-1-propen-1-yl)phenyl)-methylidene}-5-nitro-2-indolinone,
(410) 3-{(Z)-1-[(2-acetyl-1,2,3,4-tetrahydro-isoquinolin-6-yl)-amino]-1-(4-((3-(2-oxo-piperidino)-1-propen-1-yl)phenyl)-methylidene}-5-nitro-2-indolinone,
(411) 3-{(Z)-1-[4-((2,4-dioxo-imidazolidin-5-ylidene)methyl)anilino]-1-(4-((3-(2-oxo-piperidino)-1-propen-1-yl)phenyl)-methylidene}-5-nitro-2-indolinone,
(412) 3-{(Z)-1-[4-((pyrrolidin-1-yl)methyl)anilino]-1-(4-((3-(2-oxo-piperidino)-1-propen-1-yl)phenyl)-methylidene}-5-nitro-2-indolinone,
(413) 3-{(Z)-1-[4-(2-(imidazol-4-yl)-(E)-ethenyl)anilino]-1-(4-((3-(2-oxo-piperidino)-1-propen-1-yl)phenyl)-methylidene}-5-nitro-2-indolinone,
(414) 3-{(Z)-1-[4-((1-methyl-2,4-dioxo-imidazolidin-5-(E/Z)-ylidene)methyl)anlino]-1-(4-((3-(2-oxo-piperidino)-1-propen-1-yl)phenyl)-methylidene}-5-nitro-2-indolinone,
(415) 3-{(Z)-1-[4-(2-ethyl-1H-imidazol-4-yl)anilino]-1-(4-(2-(2-oxo-piperidino)-ethyl)-phenyl)-methylidene}-5-nitro-2-indolinone,
(416) 3-{(Z)-1-[4-((pyrrolidin-1-yl)methyl)anilino]-1-(4-methyl-phenyl)methylidene}-5-nitro-2-indolinone,
(417) 3-{(Z)-1-[4-((pyrrolidin-1-yl)methyl)anilino]-1-(4-methoxy-phenyl)methylidene}-5-nitro-2-indolinone,
(418) 3-{(Z)-1-[4-((pyrrolidin-1-yl)methyl)anilino]-1-(4-fluoro-phenyl)methylidene}-5-nitro-2-indolinone,
(419) 3-{(Z)-1-[4-((pyrrolidin-1-yl)methyl)anilino]-1-(4-chloro-phenyl)methylidene}-5-nitro-2-indolinone,
(420) 3-{(Z)-1-[4-((pyrrolidin-1-yl)methyl)anilino]-1-(4-bromo-phenyl)methylidene}-5-nitro-2-indolinone,
(421) 3-{(Z)-1-[4-(imidazol-4-yl)anilino]-1-(4-methyl-phenyl)methylidene}-5-nitro-2-indolinone,
(422) 3-{(Z)-1-[4-(imidazol-4-yl)anilino]-1-(4-methoxy-phenyl)methylidene}-5-nitro-2-indolinone,
(423) 3-{(Z)-1-[4-(imidazol-4-yl)anilino]-1-(4-fluor-phenyl)methylidene}-5-nitro-2-indolinone,
(424) 3-{(Z)-1-[4-(imidazol-4-yl)anilino]-1-(4-chloro-phenyl)methylidene}-5-nitro-2-indolinone,
(425) 3-{(Z)-1-[4-(imidazol-4-yl)anilino]-1-(4-bromo-phenyl)methylidene}-5-nitro-2-indolinone,
(426) 3-{(Z)-1-[(4,4-dimethyl-1,3-dioxo-1,2,3,4-tetrahydro-isoquinolin-6-yl)-amino]-1-phenylmethylidene-5-nitro-2-indolinone,
(427) 3-{(Z)-1-[(4,4-dimethyl-1,3-dioxo-1,2,3,4-tetrahydro-isoquinolin-7-yl)-amino]-1-phenylmethylidene-5-nitro-2-indolinone.

EXAMPLE 20

Dry ampoule containing 75 mg of active substance per 10 ml
Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 21

Dry ampoule containing 35 mg of active substance per 2 ml
Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 22

Tablet containing 50 mg of active substance

Composition:

| | | | |
|---|---|---|---|
| (1) | Active substance | 50.0 | mg |
| (2) | Lactose | 98.0 | mg |
| (3) | Maize starch | 50.0 | mg |
| (4) | Polyvinylpyrrolidone | 15.0 | mg |
| (5) | Magnesium stearate | 2.0 | mg |
| | | 215.0 | mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 23

Tablet containing 350 mg of active substance

Preparation:

| | | | |
|---|---|---|---|
| (1) | Active substance | 350.0 | mg |
| (2) | Lactose | 136.0 | mg |
| (3) | Maize starch | 80.0 | mg |
| (4) | Polyvinylpyrrolidone | 30.0 | mg |
| (5) | Magnesium stearate | 4.0 | mg |
| | | 600.0 | mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 24

Capsules containing 50 mg of active substance

Composition:

| | | | |
|---|---|---|---|
| (1) | Active substance | 50.0 | mg |
| (2) | Dried maize starch | 58.0 | mg |
| (3) | Powdered lactose | 50.0 | mg |
| (4) | Magnesium stearate | 2.0 | mg |
| | | 160.0 | mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 25

Capsules containing 350 mg of active substance
Composition:

| | | | |
|---|---|---|---|
| (1) | Active substance | 350.0 | mg |
| (2) | Dried maize starch | 46.0 | mg |
| (3) | Powdered lactose | 30.0 | mg |
| (4) | Magnesium stearate | 4.0 | mg |
| | | 430.0 | mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 26

Suppositories containing 100 mg of active substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula

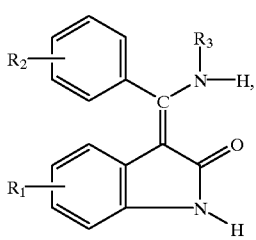

(I)

wherein $R_1$ denotes a hydrogen, fluorine, chlorine, bromine or iodine atom, a nitro, amino, $C_{1-4}$-alkanoylamino, $(C_{1-5}$-alkoxy)carbonylamino or benzyloxycarbonylamino group, $R_2$ denotes a hydrogen, fluorine, chlorine, bromine or iodine atom, a $C_{1-5}$-alkyl, trifluoromethyl, cyano, aminocarbonyl, nitro or amino group, a $C_{1-5}$-alkyl group, which is substituted by an amino, phthalimido, $C_{1-5}$-alkylamino, $C_{3-7}$-cycloalkylamino, $C_{3-4}$-alkenylamino, benzylamino, di-($C_{1-5}$-alkyl)-amino, $C_{2-6}$-alkyleneimino, di-($C_{3-4}$-alkenyl)-amino, N-($C_{1-5}$-alkyl)-N-($C_{3-4}$-alkenyl)-amino, N-($C_{1-5}$-alkyl)-N-benzylamino, $C_{1-4}$-alkanoylamino, ($C_{1-5}$-alkoxy)carbonylamino, benzyloxycarbonylamino, N-($C_{1-4}$-alkanoyl)-N-($C_{1-5}$-alkyl)-amino, α-oxo-$C_{3-6}$-alkyleneimino, N-(($C_{1-5}$-alkoxy)carbonyl)-N-($C_{1-5}$-alkyl)-amino, N-benzyloxycarbonyl-N-($C_{1-5}$-alkyl)-amino, N-($C_{1-4}$-alkanoyl)-N-($C_{2-4}$-alkenyl)-amino, N-(($C_{1-5}$-alkoxy)carbonyl)-N-($C_{2-4}$-alkenyl)-amino, N-benzyloxycarbonyl-N-($C_{2-4}$-alkenyl)-amino, N-($C_{1-4}$-alkanoyl)-N-benzylamino, N-(($C_{1-5}$-alkoxy)carbonyl)-N-benzylamino, N-benzyloxycarbonyl-N-benzylamino, ($C_{1-5}$-alkoxy)carbonyl, benzyloxycarbonyl, carboxy, cyano, amidinocarbonyl or imidazolyl group, a $C_{2-5}$-alkenyl group, which is substituted by a phthalimido, $C_{1-4}$-alkanoylamino, ($C_{1-5}$-alkoxy)carbonylamino, benzyloxycarbonylamino, N-($C_{1-4}$-alkanoyl)-N-($C_{1-5}$-alkyl)-amino, α-oxo-$C_{3-6}$-alkyleneimino, N-(($C_{1-5}$-alkoxy)carbonyl)-N-($C_{1-5}$-alkyl)-amino, N-benzyloxycarbonyl-N-($C_{1-5}$-alkyl)-amino, N-($C_{1-4}$-alkanoyl)-N-($C_{2-4}$-alkenyl)-amino, N-(($C_{1-5}$-alkoxy)carbonyl)-N-($C_{2-4}$-alkenyl)-amino, N-benzyloxycarbonyl-N-($C_{2-4}$-alkenyl)-amino, N-($C_{1-4}$-alkanoyl)-N-benzylamino, N-(($C_{1-5}$-alkoxy)carbonyl)-N-benzylamino, N-benzyloxycarbonyl-N-benzylamino, ($C_{1-5}$-alkoxy)carbonyl, benzyloxycarbonyl, carboxy, cyano or aminocarbonyl group, or an allyl group which is substituted in the 3-position by an amino, $C_{1-5}$-alkylamino, $C_{3-7}$-cycloalkylamino, $C_{3-4}$-alkenylamino, benzylamino, di-($C_{1-5}$-alkyl)-amino, $C_{2-6}$-alkyleneimino, di-($C_{3-4}$-alkenyl)-amino, N-($C_{1-5}$-alkyl)-N-($C_{3-4}$-alkenyl)-amino or N-($C_{1-5}$-alkyl)-N-benzylamino group, and $R_3$ denotes a group of the formulae

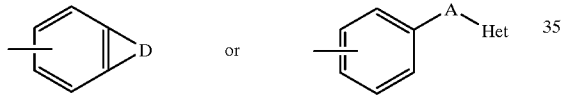

wherein

A denotes a bond, a $C_{1-4}$-alkylene, $C_{1-4}$-alkylidene, $C_{2-4}$-alkenylene or $C_{2-4}$-alkenylidene group, whilst a hydrogen atom which is bound to the carbon atom of the binding site in the group Het, together with a hydrogen atom of the group A in the α-position, may also be replaced by another carbon-carbon bond, D denotes a —CH=CH—$NR_a$, —CH=N—$NR_a$, —N=CH—$NR_a$, —$NR_a$—CO—$NR_b$, —$CH_2$—CO—$NR_a$, —CO—$NR_c$—CO, —$CH_2$—$NR_a$—$CH_2$, —$CH_2$—$CH_2$—$NR_a$, —CH=CH—CH=N, —$CH_2$—$CH_2$—$CH_2$—$NR_d$, —CH=CH—N=CH, —$CH_2$—$CH_2$—$NR_d$—$CH_2$, —$CH_2$—$CH_2$—CO—NH, —CH=CH—CO—NH, —$NR_a$—CO—CH=N or —($R_aCR_b$)—CO—$NR_a$—CO bridge, whilst $R_a$ and $R_b$, which may be identical or different, each denote a hydrogen atom or a methyl group, $R_c$ denotes a hydrogen atom, a ($C_{1-5}$-alkoxy)carbonyl-$C_{1-5}$-alkyl or benzyloxycarbonyl-$C_{1-5}$-alkyl group, $R_d$ denotes a hydrogen atom, a $C_{1-5}$-alkyl, $C_{1-4}$-alkanoyl, ($C_{1-5}$-alkoxy)carbonyl or benzyloxycarbonyl group, and Het denotes a 5-membered heteroaromatic ring which contains a nitrogen atom or a nitrogen atom and an oxygen, sulphur or nitrogen atom, whilst the abovementioned ring may also be substituted by a $C_{1-5}$-alkyl, $C_{5-7}$-cycloalkyl, phenyl, phenyl-$C_{1-3}$-alkyl, amino, $C_{1-4}$-alkanoylamino, ($C_{1-5}$-alkoxy)carbonylamino or benzyloxycarbonylamino group and also by a further $C_{1-5}$-alkyl group, a 5-membered dihydrogenated heteroaromatic ring which contains a nitrogen atom or a nitrogen atom and an oxygen, sulphur or nitrogen atom, whilst the abovementioned ring may also be substituted by one or two $C_{1-5}$-alkyl groups and may contain a carbonyl group and additionally may be substituted at a cyclic nitrogen atom by a ($C_{1-5}$-alkoxy)carbonyl or benzyloxycarbonyl group, a 5-membered tetrahydrogenated heteroaromatic ring, which contains a nitrogen atom, whilst the abovementioned ring may additionally be substituted by one or two $C_{1-5}$-alkyl groups, by a hydroxy, carboxy, ($C_{1-5}$-alkoxy)carbonyl or aminocarbonyl group and may also contain one or two carbonyl groups, a 5-membered tetrahydrogenated heteroaromatic ring which contains a nitrogen atom and an oxygen, sulphur or nitrogen atom, whilst the abovementioned ring may additionally be substituted by one or two $C_{1-5}$-alkyl groups and may contain one or two carbonyl groups, or a tetrazolyl or imidazo[1,2-a]pyrimidin-2-yl group, or a pharmaceutically acceptable salt thereof.

2. A compound of the formula I according to claim 1, wherein $R_1$ denotes a hydrogen, fluorine, chlorine or bromine atom, a nitro, amino, $C_{1-4}$-alkanoylamino, ($C_{1-5}$-alkoxy)carbonylamino or benzyloxycarbonylamino group, $R_2$ denotes a hydrogen, fluorine, chlorine or bromine atom, a methyl, trifluoromethyl, cyano, aminocarbonyl, nitro or amino group, a $C_{1-2}$-alkyl group, which is substituted by an amino, phthalimido, $C_{1-2}$-alkylamino, di-($C_{1-2}$-alkyl)-amino, $C_{2-6}$-alkyleneamino, $C_{1-2}$-alkanoylamino, ($C_{1-5}$-alkoxy)carbonylamino, benzyloxycarbonylamino, N-($C_{1-2}$-alkanoyl)-N-($C_{1-2}$-alkyl)-amino, N-(($C_{1-5}$-alkoxy)carbonyl)-N-($C_{1-2}$-alkyl)-amino, α-oxo-$C_{3-6}$-alkyleneimino, N-benzyloxycarbonyl-N-($C_{1-2}$-alkyl)-amino, ($C_{1-5}$-alkoxy)carbonyl, benzyloxycarbonyl, carboxy, cyano, aminocarbonyl or imidazolyl group, or an allyl group which is substituted in the 3-position by a $C_{2-6}$-alkylene or α-oxo-$C_{3-6}$-alkyleneimino group, $R_3$ denotes a group of the formulae

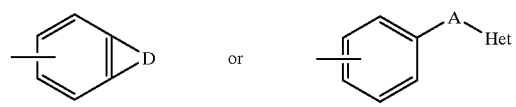

wherein D and Het are as hereinbefore defined and A denotes a bond, a $C_{1-3}$-alkylene, $C_{1-3}$-alkylidene, $C_{2-3}$-alkenylene or $C_{2-3}$-alkenylidene group, whilst a hydrogen atom which is bound to the carbon atom of the binding site in the group Het, together with a hydrogen atom of the group A in the α-position, may also be replaced by another carbon-carbon bond, or a pharmaceutically acceptable salt thereof.

3. A compound of the formula I according to claim 1, wherein $R_1$ denotes a hydrogen atom or a nitro group, $R_2$ denotes a hydrogen or chlorine atom, a methyl, trifluoromethyl, cyano, aminomethyl, aminoethyl or phthalimido group, a methyl or ethyl group each of which is substituted by a methylamino, dimethylamino, ethylamino, diethylamino, pyrrolidino, piperidino, α-oxo-pyrrolidino, α-oxo-piperidino, acetylamino, methoxycarbonylamino, ethoxycarbonylamino, benzyloxycarbonylamino, N-acetyl-N-methylamino, N-methoxycarbonyl-N-methyl-amino, N-ethoxycarbonyl-N-methyl-amino, N-benzyloxycarbonyl-N-methyl-aminomethyl, 2-(N-benzyloxy-carbonyl-N-methyl-amino)-ethyl or imidazolyl group, $R_3$ denotes a 1-methyl-2-oxo-2,3-dihydro-1H-benzimidazol-5-yl, 1,2,3,4-tetrahydro-isoquinolin-6-yl, 2-acetyl-1,2,3,4-tetrahydro-isoquinolin-6-yl, 2-acetyl-1,2,3,4-tetrahydro-isoquinolin-7-yl, 2-ethyl-1,2,3,4-tetrahydro-isoquinolin-6-yl, 2-ethyl-1,2,3,4-tetrahydro-isoquinolin-7-yl, 4-(imidazol-2-yl)-phenyl, 4-(1-methyl-imidazol-2-yl)-phenyl, 4-(imidazol-4-yl)-phenyl, 4-(1-methyl-imidazol-4-yl)-phenyl, 4-(1-methyl-imidazol-5-yl)-phenyl, 4-(5-methyl-imidazol-4-yl)-phenyl, 4-(4-methyl-imidazol-5-yl)-phenyl, 4-(2-methyl-imidazol-4-yl)-phenyl, 4-(2-ethyl-imidazol-4-yl)-phenyl, 4-(2-acetylamino-imidazol-4-yl)-phenyl, 4-(2-acetylamino-5-methyl-imidazol-4-yl)-phenyl, imidazo[1,2-a]pyrimidin-2-yl, 4-[(2,4-dioxo-imidazolidin-5-yl)methyl]-phenyl, 4-[(2,4-dioxo-imidazolidin-5-ylidene)methyl]-phenyl, 4-[(imidazol-4-yl)methyl]-phenyl, 4-[(imidazol-5-yl)methyl]-phenyl, 4-[(1-pyrrolidinyl)methyl]-phenyl, 4-[2-(imidazol-4(5)-yl)ethyl]-phenyl, 4-[2-(imidazol-4-yl)ethenyl]-phenyl or 4-[2-(imidazol-5-yl)ethenyl]-phenyl group, or a pharmaceutically acceptable salt thereof.

4. A compound of the formula I according to claim 1, wherein $R_1$ denotes a hydrogen atom or in the 5-position a nitro group, $R_2$ denotes a hydrogen atom, a methyl or trifluoromethyl group, $R_3$ denotes a 4-(1-methyl-imidazol-2-yl)-phenyl, 4-(imidazol-4-yl)-phenyl, 4-(imidazol-5-yl)-phenyl, 4-(1-methyl-imidazol-4-yl)-phenyl, 4-(1-methyl-imidazol-5-yl)-phenyl, 4-(2-methyl-imidazol-4-yl)-phenyl, 4-(2-acetylamino-imidazol-4-yl)-phenyl, 4-[(2,4-dioxo-imidazolidin-5-ylidene)methyl]-phenyl, 4-[(1-pyrrolidinyl)-methyl]-phenyl, 4-[2-(imidazol-4-yl) ethenyl]-phenyl or 1,2,3,4-tetrahydro-isoquinolin-6-yl group, or a pharmaceutically acceptable salt thereof.

5. A compound selected from the group consisting of:

(a) 3-{(Z)-1-[4-(1H-imidazol-4-yl)anilino]-1-phenylmethylidene}-2-indolinone, (b) 3-{(Z)-1-[4-(1H-imidazol-4-yl)anilino]-1-phenylmethylidene}-5-nitro-2-indolinone, (c) 3-{(Z)-1-[4-(1H-imidazol-4-yl)anilino]-1-(4-trifluoromethyl-phenyl)methylidene}-5-nitro-2-indolinone, (d) 3-{(Z)-1-[4-(1H-imidazol-4-yl)anilino]-1-(4-methyl-phenyl)methylidene}-5-nitro-2-indolinone, (e) 3-{(Z)-1-[4-((2,4-dioxo-imidazolidin-5-yl)methyl) anilino]-1-phenylmethylidene}-5-nitro-2-indolinone, (f) 3-{(Z)-1-[4-(2-methyl-1H-imidazol-4-yl)anilino]-1-phenylmethylidene}-5-nitro-2-indolinone, (g) 3-{(Z)-1-[4-((pyrrolidin-1-yl)methyl)anilino]-1-phenylmethylidene}-5-nitro-2-indolinone, and (h) 3-{(Z)-1-[(1,2,3,4-tetrahydro-isoquinolin-6-yl) amino]-1-phenylmethylidene}-5-nitro-2-indolinone or a pharmaceutically acceptable salt thereof.

6. A pharmaceutical composition containing an anti-cell proliferative amount of a compound of the formula I according to claim 1, 2, 3, 4 or 5.

7. A method for treating excessive or abnormal cell proliferation which comprises administering to a host in need of such treatment an anti-cell proliferative amount of a compound of the formula I according to claim 1, 2, 3, 4 or 5.

* * * * *